(12) United States Patent
Song et al.

(10) Patent No.: US 11,839,657 B2
(45) Date of Patent: Dec. 12, 2023

(54) IONIZABLE LIPIDS AND COMPOSITIONS FOR NUCLEIC ACID DELIVERY

(71) Applicant: WESTGENE BIOPHARMA CO., LTD, Chengdu (CN)

(72) Inventors: Xiangrong Song, Chengdu (CN); Xiawei Wei, Chengdu Tianfu International Bio-Town (CN); Yuquan Wei, Chengdu Tianfu International Bio-Town (CN)

(73) Assignee: WESTGENE BIOPHARMA CO., LTD, Chengdu (CN)

( * ) Notice: Subject to any disclaimer, the term of this patent is extended or adjusted under 35 U.S.C. 154(b) by 0 days.

(21) Appl. No.: 18/117,049

(22) Filed: Mar. 3, 2023

(65) Prior Publication Data

US 2023/0226192 A1   Jul. 20, 2023

Related U.S. Application Data

(63) Continuation of application No. PCT/CN2022/086310, filed on Apr. 12, 2022.

(30) Foreign Application Priority Data

Apr. 13, 2021  (CN) .......................... 202110396368.4

(51) Int. Cl.
| | |
|---|---|
| A61K 47/54 | (2017.01) |
| A61K 47/60 | (2017.01) |
| A61K 9/51 | (2006.01) |
| A61K 39/215 | (2006.01) |
| A61K 47/24 | (2006.01) |
| A61K 47/28 | (2006.01) |
| C07C 229/12 | (2006.01) |
| C07C 237/06 | (2006.01) |
| C07C 271/20 | (2006.01) |
| C07C 323/25 | (2006.01) |
| A61K 39/00 | (2006.01) |

(52) U.S. Cl.
CPC .......... *A61K 47/543* (2017.08); *A61K 9/5123* (2013.01); *A61K 39/215* (2013.01); *A61K 47/24* (2013.01); *A61K 47/28* (2013.01); *A61K 47/60* (2017.08); *C07C 229/12* (2013.01); *C07C 237/06* (2013.01); *C07C 271/20* (2013.01); *C07C 323/25* (2013.01); *A61K 2039/6018* (2013.01)

(58) Field of Classification Search
None
See application file for complete search history.

(56) References Cited

FOREIGN PATENT DOCUMENTS

| WO | 2019/246203 A1 | 12/2019 |
|---|---|---|
| WO | 2022/218295 A1 | 10/2022 |

OTHER PUBLICATIONS

International Search Report and Written Opinion for Application No. PCT/CN2022/086310, dated Feb. 8, 2023, 18 pages.

*Primary Examiner* — Celeste A Roney

(74) *Attorney, Agent, or Firm* — McCarter & English, LLP

(57) ABSTRACT

The present disclosure relates to a compound of Formula (I)

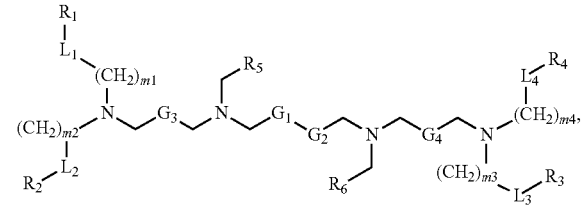

or a pharmaceutically acceptable salt thereof, which can be incorporated into a lipid particle for delivering an active agent, such as a nucleic acid.

24 Claims, 7 Drawing Sheets

IONIZABLE LIPIDS AND COMPOSITIONS FOR NUCLEIC ACID DELIVERY

CROSS-REFERENCE TO RELATED APPLICATIONS

This application is a continuation of International Application No.: PCT/CN2022/086310, filed on Apr. 12, 2022, which claims priority to Chinese Patent Application No. 202110396368.4, filed Apr. 13, 2021. The entire contents of the aforementioned application are incorporated herein by reference.

TECHNICAL FIELD

The present disclosure relates to ionizable lipids and its compositions for nucleic acid delivery, belonging to the field of medicinal chemistry.

BACKGROUND

Nucleic acid drugs include DNA, antisense oligonucleotides (ASOs), small interfering RNAs (siRNAs), microRNAs (miRNAs), miRNA mimics, antimiRs, ribozymes, mRNAs, aptamers, plasmids, and CRISPR RNAs. The application of nucleic acid drugs is limited by its chemical properties, which are easily degraded into a single nucleotide by nucleases in vitro and in vivo, resulting loss of activity.

Therefore, the application of nucleic acid drugs commonly requires special delivery vectors, including viral vectors and non-viral vectors. Viral vectors (including retroviruses, lentiviruses, adeno-associated viruses, etc.) have potent transfection efficiency. However, unfavorable immunogenicity, restricted loading capacity, complex production process and other factors limit its clinical application. Currently, non-viral vectors are a class of gene delivery vectors with good application prospects, which load mRNA by adsorption of cations formed by delivery materials with mRNA phosphate ions to form liposomes or nanoparticles, which protect them from nuclease degradation. Collectively, non-viral vectors is relatively easy to obtain, low immunogenicity, and high safety.

Traditionally, non-viral nucleic acid delivery materials are easily adsorbed by plasma proteins in vivo and then taken up by the reticuloendothelial system, resulting the loaded nucleic acid drugs are destroyed duo to its strong positive electrical properties. Ionizable lipid-based nanoparticles were prepared by ionizable lipid-based materials, which realize the loading of nucleic acid drugs by electrostatic adsorption of nucleic acids and show positive electricity in acidic environment in vitro. Importantly, they show electroneutrality to avoid the adsorption of plasma proteins and the capture of reticuloendothelial system after entering the neutral environment in vivo. Overall, ionizable nanoparticles have a very broad prospect in the field of nucleic acid delivery.

However, there are still relatively few clinical applications of ionizable nanoparticles. Therefore, the development of ionizable nucleic acid delivery materials with high efficiency and safety is of great significance for the wide application of nucleic acid drug gene therapy.

SUMMARY

Described herein are compounds of Formula (I) and pharmaceutically acceptable salts thereof that can be used as ionizable lipids for forming nucleic acid-lipid particles. It is unexpected to find that the ionizable lipids disclosed herein and the corresponding and nanoparticles have good encapsulation efficiency for mRNA. They also have stronger transfection ability, in vivo mRNA expression, immune anti-tumor effects.

In one aspect, the present disclosure provides a compound of Formula (I):

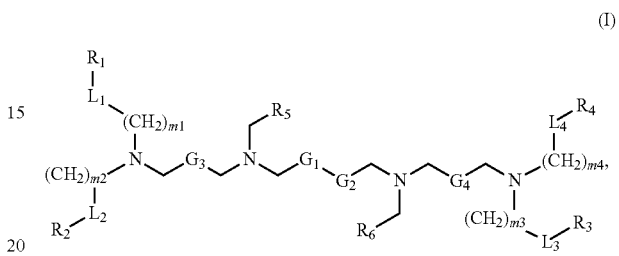

or a pharmaceutically acceptable salt thereof, wherein the variables shown in the formula are defined herein.

Also provided are pharmaceutical compositions comprising a compound of Formula (I), a pharmaceutically acceptable salt thereof and a nucleic acid drug.

DETAILED DESCRIPTION

Figure 1:
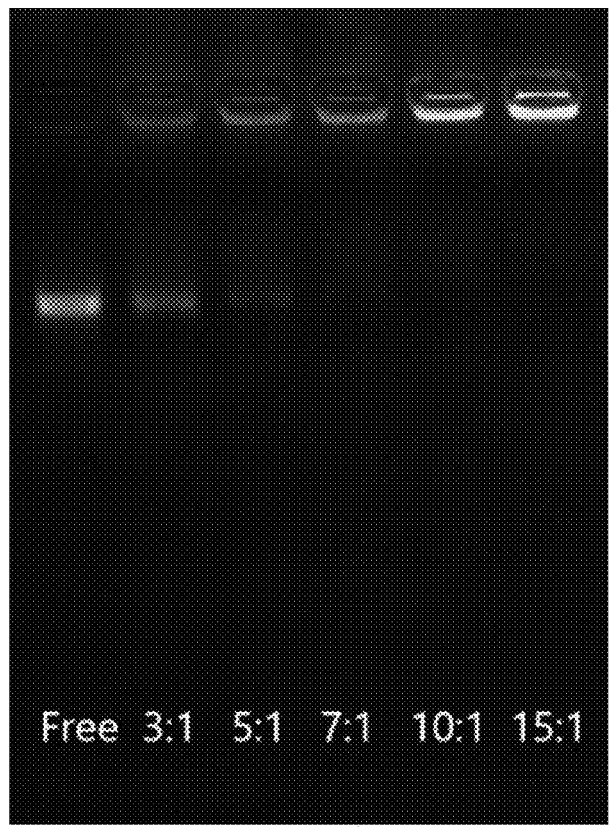
FIG. 1 II-1. Gel block results of LNP@mRNA.

The present disclosure aims to solve at least one of the existing technical problems and providing ionizable lipids for nucleic acid delivery.

In the first embodiment, the present disclosure provides a compound of Formula (I):

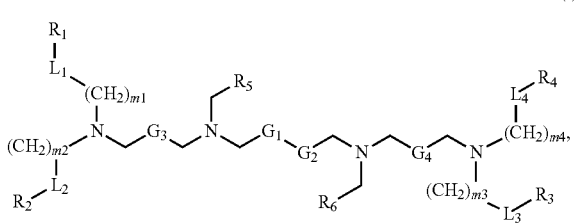

(I)

or a pharmaceutically acceptable salt thereof, wherein
m1, m2, m3, and m4 are each independently selected from 1, 2, 3, 4, or 5;

$L_1$, $L_2$, $L_3$, and $L_4$ are each independently selected from —CH(OH)—, —C(=O)—, —C(=O)O—, —OC(=O)—, —C(=O)S—, —SC(=O)—, —C(=O)NR$_a$—, —NR$_a$C(=O)—, —NR$_a$C(=O)O—, —OC(=O)NR$_a$—, —O—, —O—O—, —S—, —S—S—, —S—S—S—, —CH(OH)CH$_2$O—, —CH(OH)CH$_2$S—, or absent, wherein
each R$_a$ is independently —H or optionally substituted $C_1$-$C_6$ alkyl;

$R_1$, $R_2$, $R_3$, and $R_4$ are each independently selected from optionally substituted $C_6$-$C_{30}$ alkyl, optionally substituted $C_6$-$C_{30}$ alkenyl, or optionally substituted $C_6$-$C_{30}$ alkynyl;

$G_1$, $G_2$, $G_3$ and $G_4$ are each independently selected from —R$_c$—, —R$_c$CH(OH)R$_d$—, —R$_c$C(=O)R$_d$—, —R$_c$C(=O)OR$_d$—, —R$_c$OC(=O)R$_d$—, —R$_c$C(=O)SR$_d$—, —R$_c$SC(=O)R$_d$—, —R$_c$C(=O)N(R$_b$)R$_d$—, —R$_c$N(R$_b$)C(=O)R$_d$—, —R$_c$N(R$_b$)C(=O)OR$_d$—, —R$_c$OC(=O)N(R$_b$)R$_d$—, —R$_c$OR$_d$—, —R$_c$—O—O—R$_d$—, —R$_c$SR$_d$—, —R$_c$—S—S—R$_d$—, —R$_c$—S—S—S—R$_d$—, or absent; wherein
each R$_b$ is independently —H or optionally substituted $C_1$-$C_6$ alkyl;
each R$_c$ and R$_d$ are independently —(CH$_2$)$_n$—, and n is 0, 1, 2, 3, or 4;

$R_5$ and $R_6$ are each independently selected from —H, —OH, or optionally substituted $C_1$-$C_6$ alkyl.

In a second embodiment, the present disclosure provides a compound according to Formula (I), or a pharmaceutically acceptable salt thereof, wherein
$G_1$ and $G_2$ are each independently —R$_c$—, $G_3$ and $G_4$ are each independently selected from —R$_c$—, —R$_c$C(=O)R$_d$—, —R$_c$C(=O)OR$_d$—, —R$_c$OC(=O)R$_d$—, —R$_c$C(=O)N(R$_b$)R$_d$—, —R$_c$N(R$_b$)C(=O)R$_d$—, —R$_c$N(R$_b$)C(=O)OR$_d$—, —R$_c$OC(=O)N(R$_b$)R$_d$—, or absent;
each R$_b$ is independently —H or $C_1$-$C_6$ alkyl;
each R$_c$ and R$_d$ are independently —(CH$_2$)$_n$—, and n is 0, 1, 2, 3, or 4. The definitions of the remaining variables are provided in the first embodiment.

In a third embodiment, the present disclosure provides a compound according to the second embodiment, or a pharmaceutically acceptable salt thereof, wherein
$G_1$ and $G_2$ are each independently —R$_c$—, $G_3$ and $G_4$ are each independently selected from —R$_c$—, —R$_c$C(=O)OR$_d$—, —R$_c$OC(=O)R$_d$—, —R$_c$C(=O)N(R$_b$)R$_d$—, —R$_c$N(R$_b$)C(=O)R$_d$—, or absent;
each R$_b$ is independently —H or $C_1$-$C_2$ alkyl;
each R$_c$ and R$_d$ are independently —(CH$_2$)$_n$— or absent, and n is 0, 1 or 2. The definitions of the remaining variables are provided in the first or third embodiment.

In a fourth embodiment, the present disclosure provides a compound according to the third embodiment, or a pharmaceutically acceptable salt thereof, wherein $G_1$ and $G_2$ are absent, $G_3$ and $G_4$ are each independently selected from —CH$_2$—, —CH$_2$C(=O)OCH$_2$—, —CH$_2$OC(=O)CH$_2$—, —CH$_2$C(=O)NHCH$_2$—, —CH$_2$NHC(=O)CH$_2$—, or absent. The definitions of the remaining variables are provided in the first embodiment.

In a fifth embodiment, the present disclosure provides a compound according to the first embodiment, or a pharmaceutically acceptable salt thereof, wherein
$G_3$ and $G_4$ are each independently —R$_c$—, $G_1$ and $G_2$ are each independently selected from —R$_c$—, —R$_c$C(=O)R$_a$—, —R$_c$C(=O)OR$_a$—, —R$_c$OC(=O)R$_a$—, —R$_c$C(=O)N(R$_b$)R$_d$—, —R$_c$N(R$_b$)C(=O)R$_a$—, —R$_c$N(R$_b$)C(=O)OR$_a$—, —R$_c$OC(=O)N(R$_b$)R$_d$—, or absent;
each R$_b$ is independently —H or $C_1$-$C_6$ alkyl;
each R$_c$ and R$_d$ are independently —(CH$_2$)$_n$—, and n is 0, 1, 2, 3, or 4. The definitions of the remaining variables are provided in the first embodiment.

In a sixth embodiment, the present disclosure provides a compound according to the fifth embodiment, or a pharmaceutically acceptable salt thereof, wherein
$G_3$ and $G_4$ are each independently —R$_c$—, $G_1$ and $G_2$ are each independently selected from —R$_c$—, —R$_c$C(=O)OR$_a$—, —R$_c$OC(=O)R$_a$—, —R$_c$C(=O)N(R$_b$)R$_d$—, —R$_c$N(R$_b$)C(=O)R$_a$—, or absent;
each R$_b$ is independently —H or $C_1$-$C_2$ alkyl;
each R$_c$ and R$_d$ are independently —(CH$_2$)$_n$— or absent, and n is 0, 1 or 2. The definitions of the remaining variables are provided in the first embodiment.

In a seventh embodiment, the present disclosure provides a compound according to the sixth embodiment, or a pharmaceutically acceptable salt thereof, wherein
$G_3$ and $G_4$ are absent, $G_1$ and $G_2$ are each independently selected from —CH$_2$—, —CH$_2$C(=O)O(CH$_2$)$_{1\text{ or }2}$—, —(CH$_2$)$_{1\text{ or }2}$OC(=O)CH$_2$—, —CH$_2$C(=O)N(R$_b$)CH$_2$—, —CH$_2$N(R$_b$)C(=O)CH$_2$—, or absent;
each R$_b$ is independently —H or $C_1$-$C_2$ alkyl. The definitions of the remaining variables are provided in the first embodiment.

In an eighth embodiment, the present disclosure provides a compound according to any one of the first through seventh embodiments, or a pharmaceutically acceptable salt thereof, wherein $L_1$, $L_2$, $L_3$, and $L_4$ are each independently selected from —CH(OH)—, —C(=O)—, —C(=O)O—, —OC(=O)—, —C(=O)NR$_a$—, —NR$_a$C(=O)—, —NR$_a$C(=O)O—, —OC(=O)NR$_a$—, —O—, —S—, —CH(OH)CH$_2$O—, —CH(OH)CH$_2$S—, or absent. The definitions of the remaining variables are provided in any one of the first through seventh embodiments.

In a ninth embodiment, the present disclosure provides a compound according to any one of the first through seventh embodiments, or a pharmaceutically acceptable salt thereof, wherein $L_1$, $L_2$, $L_3$, and $L_4$ are each independently selected from —CH(OH)—, —C(=O)—, —C(=O)O—, —OC(=O)—, —C(=O)NR$_a$—, —NR$_a$C(=O)—, —O—, —S—, or absent; each R$_a$ is independently —H or $C_1$-$C_2$ alkyl. The definitions of the remaining variables are provided in any one of the first through seventh embodiments.

In a tenth embodiment, the present disclosure provides a compound according to any one of the first through ninth embodiments, or a pharmaceutically acceptable salt thereof, wherein m1, m2, m3, and m4 are each independently selected from 1 or 2. The definitions of the remaining variables are provided in any one of the first through ninth embodiments.

In an eleventh embodiment, the present disclosure provides a compound according to any one of the first through tenth embodiments, or a pharmaceutically acceptable salt thereof, wherein $R_1$, $R_2$, $R_3$, and $R_4$ are each independently selected from $C_6$-$C_{15}$ alkyl, $C_6$-$C_{15}$ alkenyl, or $C_6$-$C_{18}$ alkynyl, wherein said $C_6$-$C_{18}$ alkyl, $C_6$-$C_{18}$ alkenyl, or $C_6$-$C_{18}$ alkynyl is optionally substituted one to three groups selected from halogen, OH, or =O. The definitions of the remaining variables are provided in any one of the first through tenth embodiments.

In a twelfth embodiment, the present disclosure provides a compound according to any one of the first through tenth embodiments, or a pharmaceutically acceptable salt thereof, wherein $R_1$, $R_2$, $R_3$, and $R_4$ are each independently selected from $C_6$-$C_{18}$ alkyl. The definitions of the remaining variables are provided in any one of the first through tenth embodiments.

In a thirteenth embodiment, the present disclosure provides a compound according to any one of the first through twelfth embodiments, or a pharmaceutically acceptable salt thereof, wherein $R_5$ and $R_6$ are each independently selected from —H, —OH, or $C_1$-$C_4$ alkyl optionally substituted with —OH. The definitions of the remaining variables are provided in any one of the first through twelfth embodiments.

In a fourteenth embodiment, the present disclosure provides a compound of Formula (I-1):

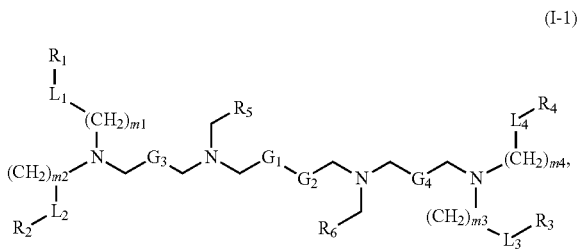

(I-1)

or a pharmaceutically acceptable salt thereof, wherein
m1, m2, m3, and m4 are the same, all of which are 1, 2, 3, 4, or 5;
$L_1$, $L_2$, $L_3$, and $L_4$ are the same, all of which are selected from —CH(OH)—, —C(=O)—, ^—C(=O)O-^^, ^—OC(=O)—^^, ^—C(=O)S—^^, ^—SC(=O)—^^, ^—C(=O)NR_a-^^, ^—NR_aC(=O)—^^, ^—NR_aC(=O)O-^^, ^—OC(=O)NR_a-^^, —O—, —O—O—, —S—, —S—S—, —S—S—S—, ^—CH(OH)CH_2O—^^, ^—CH(OH)CH_2S—^^ or absent, wherein
^- represents the point which attaches to $R_{1-4}$; -^^ represents the point which attaches to —$(CH_2)_{m1-m4}$—; and
each $R_a$ is independently —H or optionally substituted $C_1$-$C_6$ alkyl;
$R_1$, $R_2$, $R_3$, and $R_4$ are the same, all of which are selected from optionally substituted $C_6$-$C_{30}$ alkyl, optionally substituted $C_6$-$C_{30}$ alkenyl, or optionally substituted $C_6$-$C_{30}$ alkynyl;
$G_1$ and $G_2$ are the same, and $G_3$ and $G_4$ are the same, when $G_1$ and $G_2$ are —$R_c$—, $G_3$ and $G_4$ are selected from —$R_c$—, *—$R_cCH(OH)R_d$—**, *—$R_cC(=O)R_d$—**, *—$R_cC(=O)OR_d$—**, *—$R_cOC(=O)R_d$—**, *—$R_cC(=O)SR_d$—**, *—$R_cSC(=O)R_d$—**, *—$R_cC(=O)N(R_b)R_d$—**, *—$R_cN(R_b)C(=O)R_d$—**, *—$R_cN(R_b)C(=O)OR_d$—**, *—$R_cOC(=O)N(R_b)R_d$—**, *—$R_cOR_d$—**, *—$R_cOR$—$R_d$—**, *—$R_cSR_d$—**, *—$R_c$—S—S—$R_d$—**, *—$R_c$—S—S—S—$R_d$—**, or absent; wherein

*- represents the point which attaches to the —$CH_2$— group next to the terminal tertiary amine atom as shown in Formula (I); -** represents the point which attaches to the —$CH_2$— group next to the middle tertiary amine atom as shown in Formula (I);
when $G_3$ and $G_4$ are —$R_c$—, $G_1$ and $G_2$ are selected from —$R_c$—, #—$R_cCH(OH)R_d$—##, #—$R_cC(=O)R_d$—##, #—$R_cC(=O)OR_d$—##, #—$R_cOC(=O)R_d$—##, #—$R_cC(=O)SR_d$—##, #—$R_cSC(=O)R_d$—##, #—$R_cC(=O)N(R_b)R_d$—##, #—$R_cN(R_b)C(=O)R_d$—##, #—$R_cN(R_b)C(=O)OR$—##, #—$R_cOC(=O)N(R_b)R_d$—##, #—$R_cOR_d$—##, #—$R_c$—O—O—$R_d$—##, #—$R_cSR_d$—##, #—$R_c$—S—S—$R_d$—##, #—$R_c$—S—S—S—$R_d$—##, or absent;
wherein
- represents the point which attaches to the —$CH_2$— group next to the middle tertiary amine atom as shown in Formula (I); -## represents the point connecting $G_1$ and $G_2$; and
each $R_b$ is independently —H or optionally substituted $C_1$-$C_6$ alkyl;
each $R_c$ and $R_d$ are independently —$(CH_2)_n$—, and n is 0, 1, 2, 3, or 4;
$R_5$ and $R_6$ are the same, both of which are selected from —H, —OH, or optionally substituted $C_1$-$C_6$ alkyl.
The terminal tertiary amine atom described herein refers to the two nitrogen atoms which are connected with —$(CH_2)_{m1-m4}$-$L_{1-4}$-$R_{1-4}$ moieties. The middle tertiary amine atom described herein refers to the two nitrogen atoms which are connected with —$CH_2R_5$ or —$CH_2R_6$.

In a fifteenth embodiment, the present disclosure provides a compound according to the fourteenth embodiment, or a pharmaceutically acceptable salt thereof, wherein
$G_1$ and $G_2$ are —$R_c$—, $G_3$ and $G_4$ are selected from —$R_c$—, *—$R_cC(=O)R_d$—**, *—$R_cC(=O)OR_d$—**, *—$R_cOC(=O)R_d$—**, *—$R_cC(=O)N(R_b)R_d$—**, *—$R_cN(R_b)C(=O)R_d$—**, *—$R_cN(R_b)C(=O)OR_d$—**, *—$R_cOC(=O)N(R_b)R_d$—**, or absent;
each $R_b$ is independently —H or $C_1$-$C_6$ alkyl;
each $R_c$ and $R_d$ are independently —$(CH_2)_n$—, and n is 0, 1, 2, 3, or 4. The definitions of the remaining variables are provided in the fourteenth embodiment.

In a sixteenth embodiment, the present disclosure provides a compound according to the fifteenth embodiment, or a pharmaceutically acceptable salt thereof, wherein
$G_1$ and $G_2$ are —$R_c$—, $G_3$ and $G_4$ are selected from *—$R_cC(=O)OR_d$—**, *—$R_cOC(=O)R_d$—**, *—$R_cC(=O)N(R_b)R_d$—**, *—$R_cN(R_b)C(=O)R_d$—**, or absent;
each $R_b$ is independently —H or $C_1$-$C_2$ alkyl;
each $R_c$ and $R_d$ are independently —$(CH_2)_n$— or absent, and n is 0, 1 or 2. The definitions of the remaining variables are provided in the fourteenth embodiment.

In a seventeenth embodiment, the present disclosure provides a compound according to the sixteenth embodiment, or a pharmaceutically acceptable salt thereof, wherein $G_1$ and $G_2$ are absent, $G_3$ and $G_4$ are selected from —$CH_2$—, *—$CH_2C(=O)OCH_2$—**, *—$CH_2OC(=O)CH_2$—**, *—$CH_2C(=O)NHCH_2$—**, *—$CH_2NHC(=O)CH_2$—**, or absent. The definitions of the remaining variables are provided in the fourteenth or sixteenth embodiment.

In an eighteenth embodiment, the present disclosure provides a compound according to the fourteenth embodiment, or a pharmaceutically acceptable salt thereof, wherein
$G_3$ and $G_4$ are —$R_c$—, $G_1$ and $G_2$ are selected from —$R_c$—, #—$R_cC(=O)R_d$—##, #—$R_cC(=O)OR_d$—##, #—$R_cOC(=O)R_d$—##, #—$R_cC(=O)N(R_b)R_d$—##, $^{\#}$—R$_c$N(R$_b$)C(=O)R$_d$—$^{\#\#}$, $^{\#}$—R$_c$N(R$_b$)C(=O)OR$_d$—$^{\#\#}$, $^{\#}$—R$_c$OC(=O)N(R$_b$)R$_d$—$^{\#\#}$, or absent;

each R$_b$ is independently —H or C$_1$-C$_6$ alkyl;

each R$_c$ and R$_d$ are independently —(CH$_2$)$_n$—, and n is 0, 1, 2, 3, or 4. The definitions of the remaining variables are provided in the fourteenth embodiment.

In an nineteenth embodiment, the present disclosure provides a compound according to the eighteenth embodiment, or a pharmaceutically acceptable salt thereof, wherein G$_3$ and G$_4$ are —R$_c$—, G$_1$ and G$_2$ are selected from —R$_c$—, $^{\#}$—R$_c$C(=O)OR$_d$—$^{\#\#}$, $^{\#}$—R$_c$OC(=O)R$_d$—$^{\#\#}$, $^{\#}$—R$_c$C(=O)N(R$_b$)R$_d$—$^{\#\#}$, $^{\#}$—R$_c$N(R$_b$)C(=O)R$_d$—$^{\#\#}$, or absent;

each R$_b$ is independently —H or C$_1$-C$_2$ alkyl;

each R$_c$ and R$_d$ are independently —(CH$_2$)$_n$— or absent, and n is 0, 1 or 2. The definitions of the remaining variables are provided in the fourteenth embodiment.

In an twentieth embodiment, the present disclosure provides a compound according to the nineteenth embodiment, or a pharmaceutically acceptable salt thereof, wherein G$_3$ and G$_4$ are absent, G$_1$ and G$_2$ are selected from —CH$_2$—, $^{\#}$—CH$_2$C(=O)O(CH$_2$)$_{1\ or\ 2}$—$^{\#\#}$, $^{\#}$—(CH$_2$)$_{1\ or\ 2}$OC(=O)CH$_2$—$^{\#\#}$, $^{\#}$—CH$_2$C(=O)N(R$_b$)CH$_2$—$^{\#\#}$, $^{\#}$—CH$_2$N(R$_b$)C(=O)CH$_2$—$^{\#\#}$, or absent; each R$_b$ is independently —H or C$_1$-C$_2$ alkyl. The definitions of the remaining variables are provided in the fourteenth embodiment.

In a twenty-first embodiment, the present disclosure provides a compound according to any one of the fourteenth through twentieth embodiments, or a pharmaceutically acceptable salt thereof, wherein L$_1$, L$_2$, L$_3$, and L$_4$ are the same, all of which are selected from —CH(OH)—, —C(=O)—, ^—C(=O)O-^^, ^—OC(=O)—^^, ^—C(=O)NR$_a$-^^, ^—NR$_a$C(=O)—^^, ^—NR$_a$C(=O)O-^^, ^—OC(=O)NR$_a$-^^, —O—, —S—, ^—CH(OH)CH$_2$O-^^, ^—CH(OH)CH$_2$S—^^, or absent. The definitions of the remaining variables are provided in any one of the fourteenth through twentieth embodiments.

In a twenty-second embodiment, the present disclosure provides a compound according to any one of the fourteenth through twentieth embodiments, or a pharmaceutically acceptable salt thereof, wherein L$_1$, L$_2$, L$_3$, and L$_4$ are the same, all of which are selected from —CH(OH)—, —C(=O)—, ^—C(=O)O-^^, ^—OC(=O)—^^, ^—C(=O)NR$_a$-^^, ^—NR$_a$C(=O)—^^, —O—, —S—, or absent; each R$_a$ is independently —H or C$_1$-C$_2$ alkyl. The definitions of the remaining variables are provided in any one of the fourteenth through twentieth embodiments.

In a twenty-third embodiment, the present disclosure provides a compound according to any one of the fourteenth through twenty-second embodiments, or a pharmaceutically acceptable salt thereof, wherein m1, m2, m3, and m4 are the same, all of which are 1 or 2. The definitions of the remaining variables are provided in any one of the fourteenth through twenty-second embodiments.

In a twenty-fourth embodiment, the present disclosure provides a compound according to any one of the fourteenth through twenty-third embodiments, or a pharmaceutically acceptable salt thereof, wherein R$_1$, R$_2$, R$_3$, and R$_4$ are the same, all of which are selected from C$_6$-C$_{18}$ alkyl, C$_6$-C$_{18}$ alkenyl, or C$_6$-C$_{18}$ alkynyl, wherein said C$_6$-C$_{18}$ alkyl, C$_6$-C$_{18}$ alkenyl, or C$_6$-C$_{18}$ alkynyl is optionally substituted one to three groups selected from halogen, OH, or =O. The definitions of the remaining variables are provided in any one of the fourteenth through twenty-third embodiments.

In a twenty-fifth embodiment, the present disclosure provides a compound according to any one of the fourteenth through twenty-third embodiments, or a pharmaceutically acceptable salt thereof, wherein R$_1$, R$_2$, R$_3$, and R$_4$ are the same, all of which are selected from C$_6$-C$_{18}$ alkyl. The definitions of the remaining variables are provided in any one of the fourteenth through twenty-third embodiments.

In a twenty-sixth embodiment, the present disclosure provides a compound according to any one of the fourteenth through twenty-fifth embodiments, or a pharmaceutically acceptable salt thereof, wherein R$_5$ and R$_6$ are the same, both of which are selected from —H, —OH, or C$_1$-C$_4$ alkyl optionally substituted with —OH. The definitions of the remaining variables are provided in any one of the fourteenth through twenty-fifth embodiments.

In one embodiment, the present disclosure provides a compound selected from the compounds disclosed in examples and Table 1, or a pharmaceutically acceptable salt thereof.

TABLE 1

| Number | Code | Chemical formula |
|---|---|---|
| 1 | II-1 | |
| 2 | III-1 | |

TABLE 1-continued
| Number | Code | Chemical formula |
|---|---|---|
| 3 | II-2 | 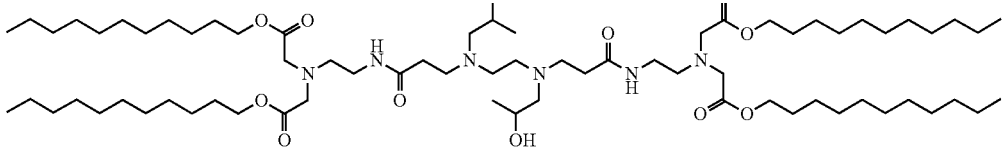 |
| 4 | II-3 | 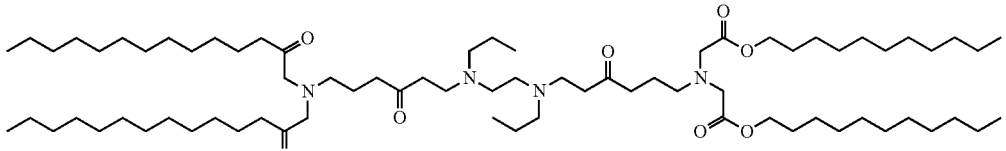 |
| 5 | II-4 | 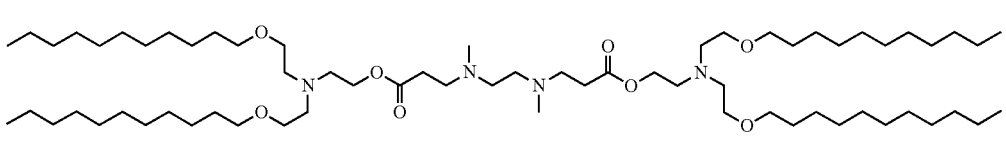 [SMILES: CCCCCCCCCCCOCCN(CCOCCCCCCCCCCC)CCOC(=O)CCN(C)CCN(C)CCC(=O)OCCN(CCOCCCCCCCCCCC)CCOCCCCCCCCCCC] |
| 6 | III-2 | 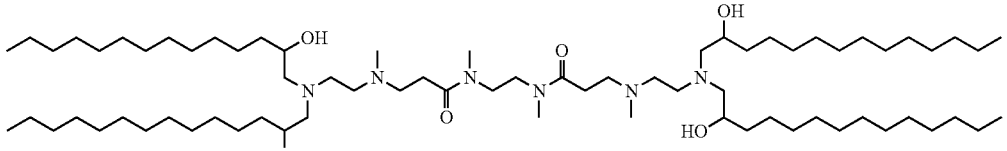 |
| 7 | V-1 | 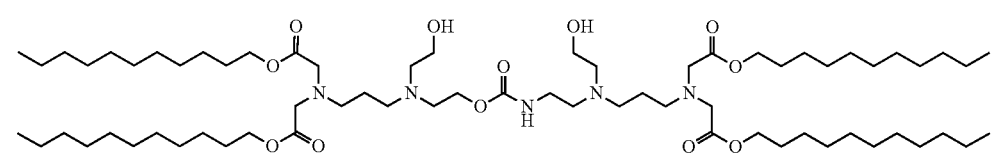 [SMILES: CCCCCCCCCCCOC(=O)CN(CCCN(CCO)CCNC(=O)OCCN(CCO)CCCN(CC(=O)OCCCCCCCCCCC)CC(=O)OCCCCCCCCCCC)CC(=O)OCCCCCCCCCCC] |
| 8 | II-5 | 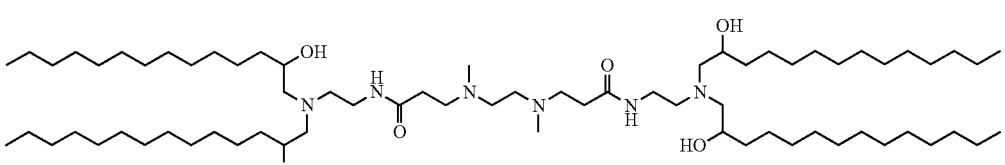 |
| 9 | III-3 | 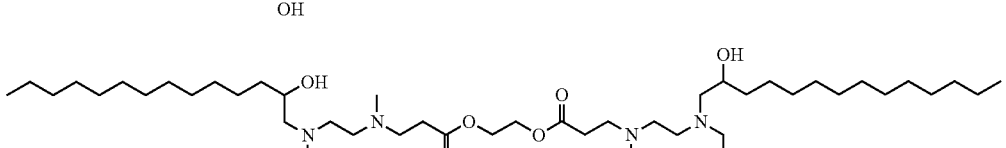 |
| 10 | IV-1 | 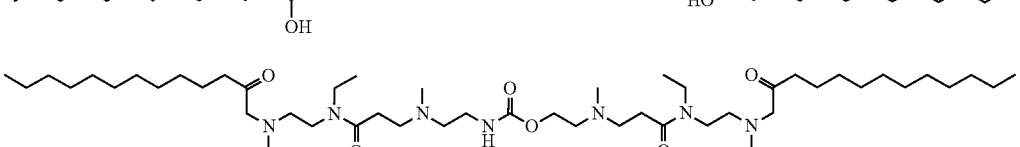 |
| 11 | VI-1 | 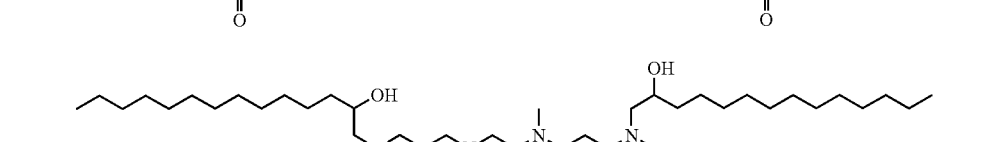 |

TABLE 1-continued

| Number | Code | Chemical formula |
|---|---|---|
| 12 | II-6 | |
| 13 | IV-2 | |
| 14 | II-7 | |
| 15 | VI-2 | |
| 16 | II-8 | |
| 17 | II-9 | |
| 18 | II-10 | |
| 19 | III-4 | |
| 20 | VI-3 | |

TABLE 1-continued

| Number | Code | Chemical formula |
|---|---|---|
| 21 | III-5 | |
| 22 | II-11 | |
| 23 | II-12 | |
| 24 | III-6 | |
| 25 | II-13 | |
| 26 | IV-3 | |
| 27 | II-14 | |
| 28 | II-15 | |
| 29 | II-16 | |

TABLE 1-continued

| Number | Code | Chemical formula |
|---|---|---|
| 30 | II-17 | |
| 31 | II-18 | |
| 32 | II-19 | |
| 33 | V-2 | |
| 34 | III-7 | |
| 35 | II-20 | |
| 36 | III-8 | |
| 37 | II-21 | |
| 38 | V-3 | |

TABLE 1-continued

| Number | Code | Chemical formula |
|---|---|---|
| 39 | IV-4 | |
| 40 | II-22 | |
| 41 | III-9 | |
| 42 | II-23 | |
| 43 | III-10 | |
| 44 | V-4 | |
| 45 | VI-4 | |
| 46 | II-24 | |
| 47 | II-25 | |

TABLE 1-continued

| Number | Code | Chemical formula |
|---|---|---|
| 48 | II-26 | |
| 49 | III-11 | |
| 50 | III-12 | |
| 51 | II-27 | |
| 52 | II-28 | |
| 53 | III-13 | |
| 54 | III-14 | |
| 55 | II-29 | |
| 56 | II-30 | |

TABLE 1-continued

| Number | Code | Chemical formula |
|---|---|---|
| 57 | II-31 | |
| 58 | II-32 | |
| 59 | III-15 | |
| 60 | II-33 | |
| 61 | II-34 | |
| 62 | II-35 | |
| 63 | II-36 | |
| 64 | III-16 | |
| 65 | II-37 | |

TABLE 1-continued

| Number | Code | Chemical formula |
|---|---|---|
| 66 | II-38 | |
| 67 | VII-1 | |
| 68 | VII-2 | |
| 69 | VII-3 | |
| 70 | VII-4 | |
| 71 | VII-5 | |
| 72 | VII-6 | |
| 73 | VII-7 | |
| 74 | VII-8 | |

TABLE 1-continued

| Number | Code | Chemical formula |
|---|---|---|
| 75 | VII-9 | |
| 76 | VII-10 | |
| 77 | VII-11 | |
| 78 | VII-12 | |
| 79 | VII-13 | |

The present disclosure also provides compounds as shown in Formula (I-0), or pharmaceutically acceptable salts, isomers, deuterated substitutes or prodrugs thereof;

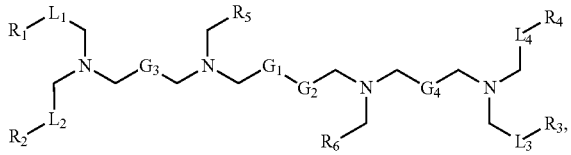

(I-0)

wherein $L_1$, $L_2$, $L_3$, $L_4$ are independently selected from —$R_k$CH(OH)—, —$R_k$C(=O)—, —$R_k$C(=O)O—, —$R_k$OC(=O)—, —$R_k$C(=O)S—, —$R_k$SC(=O)—, —$R_k$C(=O)$NR_a$—, —$R_k$$NR_a$C(=O)—, —$R_k$$NR_a$C(=O)O—, —$R_k$OC(=O)$NR_a$—, —$R_k$O—, —$R_k$—O—O—, —$R_k$S—, —$R_k$—S—S—, —$R_k$—S—S—S—, —$R_k$CH(OH)CH$_2$O—, —$R_k$CH(OH)CH$_2$S— or missing, $R_k$ is —(CH$_2$)$_k$— or missing, k is an integer above 1, and $R_a$ is a —H, substituted or unsubstituted alkyl group;

$R_1$, $R_2$, $R_3$, $R_4$ are independently selected from $C_1$-$C_{30}$ linear alkyl, $C_1$-$C_{30}$ branched alkyl, $C_2$-$C_{30}$ linear alkenyl, $C_2$-$C_{30}$ branched enyl, $C_2$-$C_{30}$ linear ethinyl, or $C_2$-$C_{30}$ branched ethinyl;

$G_1$, $G_2$, $G_3$, $G_4$ are independently selected from —$R_c$—, —$R_c$CH(OH)$R_d$—, —$R_c$C(=O)$R_d$—, —$R_c$C(=O)OR$_d$—, —$R_c$OC(=O)$R_d$—, —$R_c$C(=O)SR$_d$—, —$R_c$SC(=O)$R_d$—, —$R_c$C(=O)N($R_b$)$R_d$—, —$R_c$N($R_b$)C(=O)$R_d$—, —$R_c$N($R_b$)C(=O)OR$_d$—, —$R_c$OC(=O)N($R_b$)$R_d$—, —$R_c$OR$_d$—, —$R_c$—O—O—$R_d$—, —$R_c$SR$_d$—, —$R_c$—S—S—$R_d$—, —$R_c$—S—S—S—$R_d$— or absent, $R_b$ is —H, substituted or unsubstituted alkyl groups, $R_c$, $R_d$ are independently selected from —(CH$_2$)$_n$— or do not exist, and n is an integer above 1;

$R_5$, $R_6$ are independently selected from —OH, —H, substituted or unsubstituted alkyl group.

Further, k is an integer of 1~10.

Further, k is 1.

Further, $L_1$, $L_2$, $L_3$, $L_4$ are independently selected from —CH(OH)—, —C(=O)—, —CH$_2$C(=O)O—, —C(=O)O—, —OC(=O)—, —C(=O)S—, —SC(=O)—, —CH$_2$C(=O)NR$_a$—, —C(=O)NR$_a$—, —NR$_a$C(=O)—, —NR$_a$C(=O)O—, —OC(=O)NR$_a$—, —CH$_2$O—, —O—, —CH$_2$—O—O—, —CH$_2$S—, —S—, —CH$_2$—S—S—, —CH(OH)CH$_2$O—, —CH(OH)CH$_2$S— or absent, $R_a$ is a —H, substituted or unsubstituted alkyl group.

Further, $L_1$, $L_2$, $L_3$, $L_4$ are independently selected from —C(=O)—, —C(=O)NR$_a$—, —CH$_2$C(=O)NR$_a$—, —NR$_a$C(=O)—, —C(=O)O—, —CH$_2$C(=O)O—, —OC(=O)—, —CH$_2$O—, —O—, —CH$_2$S—, —CH(OH)—, —CH(OH)CH$_2$O—, —CH(OH)CH$_2$S— or absent, and R$_a$ is a —H or an unsubstituted alkyl group.

Further, R$_a$ is a —H or an unsubstituted C$_1$-C$_6$ alkyl group.

Further, R$_a$ is a —H.

Further, L$_1$, L$_2$, L$_3$, L$_4$ are independently selected from —C(=O)—, —C(=O)NH—, —CH$_2$C(=O)NH—, —C(=O)O—, —CH$_2$C(=O)O—, —CH$_2$O—, —CH$_2$S—, —CH(OH)—, —CH(OH)CH$_2$O— or absent; preferably, L$_1$, L$_2$, L$_3$, L$_4$ are independently selected from —C(=O)NH—, —C(=O)O—, —CH(OH)—, —CH(OH)CH$_2$O— or absent.

Further, L$_1$ and L$_2$ are selected from the same group, and L$_3$ and L$_4$ are selected from the same group.

Further, L$_1$, L$_2$, L$_3$ and L$_4$ are selected from the same group.

Further, R$_1$, R$_2$, R$_3$, R$_4$ are independently selected from C$_1$-C$_{30}$ linear alkyl, C$_2$-C$_{30}$ linear alkenyl, C$_2$—C$_{30}$ linear ethinyl.

Further, R$_1$, R$_2$, R$_3$, R$_4$ are independently selected from unsubstituted C$_1$-C$_{30}$ linear alkyl groups.

Further, R$_1$, R$_2$, R$_3$ and R$_4$ are independently selected from self-unsubstituted C$_8$~C$_{18}$ linear alkyl groups.

Further, R$_1$, R$_2$, R$_3$ and R$_4$ are independently selected from unsubstituted C$_{10}$~C$_{14}$ linear alkyl groups.

Further, R$_1$, R$_2$, R$_3$ and R$_4$ are selected from the same group.

Further, G$_3$ is selected from

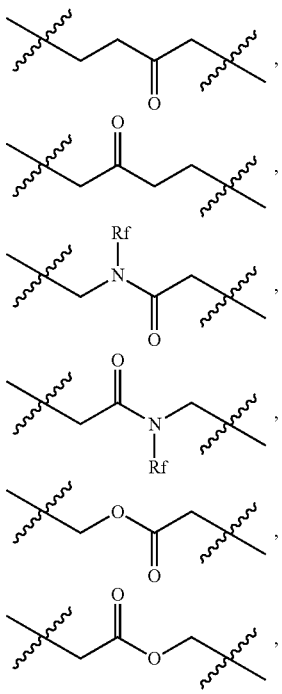

—(CH$_2$)$_{n3}$— or absent, R$_f$ is a —H or an unsubstituted alkyl, and n3 is an integer from 1~10.

Preferably, G$_3$ is selected from

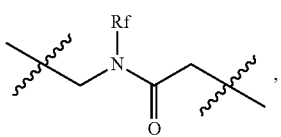

—(CH$_2$)$_{n3}$— or absent, R$_f$ is a —H or unsubstituted alkyl, and n3 is an integer from 1~10.

Further, R$_f$ is either a —H or an unsubstituted C$_1$~C$_6$ alkyl group.

Further, R$_f$ is a —H, methyl, ethyl, or propyl.

Further, n3 is 1 or 2.

Preferably, n3 is 1.

Further, G1-G2 or G2-G1 is selected from

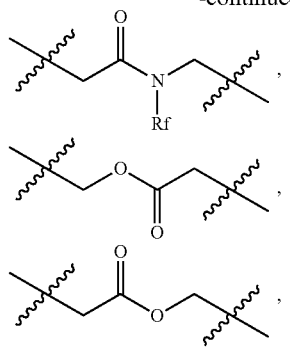

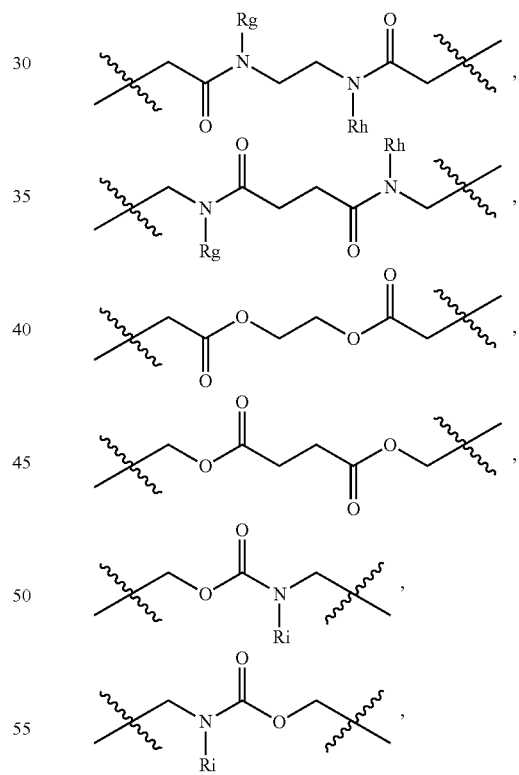

—(CH$_2$)$_{n2}$— or does not exist, R$_g$, R$_h$, R$_i$ are independently selected from —H or unsubstituted alkyl groups, and n2 is an integer of 1~10.

Further, R$_g$, R$_h$, and R$_i$ are independently selected from —H or unsubstituted C$_1$-C$_6$ alkyl groups.

Further, R$_g$, R$_h$, and R$_i$ are independently selected from —H, methyl or ethyl groups.

Further, n2 is 1 or 2.

Further, G4 is selected from

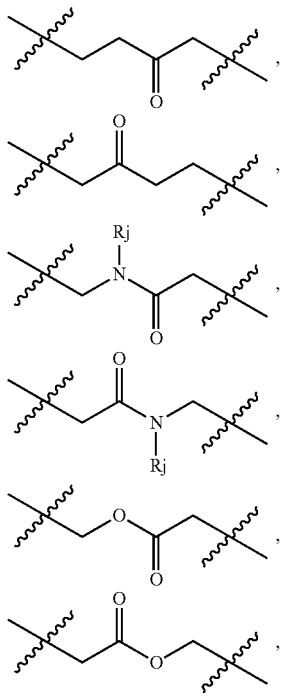

—(CH$_2$)$_{n4}$— or absent, R$_j$ is a —H or an unsubstituted alkyl, and n4 is an integer from 1~10.

Further, R$_j$ is a —H or an unsubstituted C$_1$~C$_6$ alkyl group.

Further, R$_j$ is —H, methyl, ethyl, or propyl.

Further, n4 is 1 or 2.

Further, R$_5$, R$_6$ are independently selected from —OH, —H, unsubstituted C$_1$-C$_6$ alkyl, —OH substituted C$_1$~C$_6$ alkyl.

Further, R$_5$ and R$_6$ are independently selected from —OH, —H, methyl, ethyl, propyl, hydroxymethyl, hydroxyethyl, and hydroxypropyl.

Further, R$_5$, R$_6$ are selected from the same group.

Among then, the writing order of the above-defined L1, L2, L3, and L4 linkages corresponds to the proximal nitrogen end to the far nitrogen end from left to right.

The writing order of the above-defined connecting keys of G1, G2, G3, and G4 is from left to right corresponding to the direction of the main chain of formula I from left to right.

The present disclosure provides the compound, or its pharmaceutically acceptable salts, isomers, deuterium substitutes or prodrugs, as nucleic acid delivery carriers.

The present disclosure provides a pharmaceutical composition containing the compound described herein, or its pharmaceutically acceptable salts, isomers, deuterium substitutes or prodrugs, and nucleic acid drugs.

Further, the pharmaceutical composition also contains at least one excipient of neutral phospholipids, steroids, and polyethylene glycol lipids.

In some embodiments, the neutral phospholipids are selected from at least one of 1,2-dioleoyl-sn-glycero-3-phosphoethanolamine (DOPE), distearoylphosphatidylcholine (DSPC), dipalmitoylphosphatidylcholine (DOPC), 1,2-distearoyl-sn-glycero-3-phosphorylethanolamine (DSPE), dimyristoylphosphatidylcholine (DMPC), 1,2-bis(dimethylphosphino)ethane (DMPE), dipalmitoylphosphatidylcholine (DPPC), 1,2-bis(diphenylphosphino)ethane (DPPE), 1,2-dierucoyl-sn-glycero-3-phophocholine (DEPC), L-α-phosphatidylcholine, hydrogenated (Soy) (HSPC) and 1-palmitoyl-2-oleoyl-sn-glycero-3-phosphocholine (POPC).

In one embodiment, the neutral phospholipid is DOPE.

In some embodiments, the mole ratio of the compound described herein: neutral phospholipid is 1:1~5:1.

In some embodiments, the steroids are selected from at least one of cholesterol, sitosterol, soybean sterol, wool sterol and ergosterol.

In one embodiment, the steroid is cholesterol.

In some embodiments, the mole ratio of the compound: steroid is 1:2~2:1.

In some embodiments, the pegylated lipids are selected from at least one of DMG-PEG and DSPE-PEG.

Preferably, the pegylated lipid is DMG-PEG2000.

In some embodiments, the mole ratio of the compound: pegylated lipids is 5:1~100:1.

Preferably, the mole ratio of the compound: polyethylene glycol lipid is 10:1~20:1.

In some embodiments, the nucleic acid drug is selected from at least one of DNA, ASO, siRNA, miRNA, mRNA, ribozyme and aptamer.

Further, the nucleic acid drug is mRNA.

Further, the drug composition is prepared into lipid nanoparticles LNP.

The above-mentioned lipid nanoparticles can be used for in vivo delivery of nucleic acid drugs such as mRNA to achieve up-regulation or down-regulation of corresponding genes, or delivery of antigen mRNA to express antigen in vivo to achieve immunotherapy, or delivery of mRNA encoding antibody to express antibody in vivo and other purposes.

The compounds and derivatives provided herein may be named according to the nomenclature system of IUPAC (International union of pure and applied chemistry) or CAS (Chemical abstracts service, Columbus, OH).

The term "alkyl" is a straight or branched saturated hydrocarbon radical of formula —C$_n$H$_{(2n+1)}$. C$_1$-C$_6$ alkyl groups include but are not limited to methyl (C$_1$), ethyl (C$_2$), n-propyl (C$_3$), isopropyl (C$_3$), n-butyl (C$_4$), tert-butyl (C$_4$), sec-butyl (C$_4$), isobutyl (C$_4$), n-amyl (C$_5$), 3-amyl (C$_5$), amyl (C$_5$), neopentyl (C$_5$), 3-methyl-2-butyl (C$_5$), tertiary amyl (C$_5$), and n-hexyl (C$_6$). As used herein, a "C$_6$-C$_{30}$ (or C$_6$-C$_{18}$) alkyl" group means a radical having from 6 to 30 (or 6 to 18) carbon atoms in a straight or branched arrangement. In some embodiments, a "C$_6$-C$_{30}$ (or C$_6$-C$_{18}$) alkyl" group means a radical having from 6 to 30 (or 6 to 18) carbon atoms in a straight arrangement. In some embodiments, a "C$_6$-C$_{30}$ (or C$_6$-C$_{18}$) alkyl" group means a radical having from 6 to 30 (or 6 to 18) carbon atoms in a branched arrangement.

The term "alkenyl" is a straight or branched hydrocarbon group containing at least one double bond. Alkenyl groups include but are not limited to vinyl, prop-1-enyl, butyl 1-enyl, butyl 2-enyl, amyl 1-enyl, amyl 2-enyl, amyl 3-enyl, hex-1-enyl, hex-2-enyl, hex-3-enyl, hex-4-enyl. As used herein, a "C$_6$-C$_{30}$ (or C$_6$-C$_{18}$) alkenyl" group means a radical having from 6 to 30 (or 6 to 18) carbon atoms in a straight or branched arrangement. In some embodiments, a "C$_6$-C$_{30}$ (or C$_6$-C$_{18}$) alkenyl" group means a radical having from 6 to 30 (or 6 to 18) carbon atoms in a straight arrangement. In some embodiments, a "C$_6$-C$_{30}$ (or C$_6$-C$_{18}$) alkenyl" group means a radical having from 6 to 30 (or 6 to 18) carbon atoms in a branched arrangement.

The term "alkynyl" is a straight or branched hydrocarbon group containing at least one triple bond. Acetyl groups include but are not limited to ethynyl, propargyl, butyl 1-alkynyl, butyl 2-alkynyl, amyl 1-alkynyl, amyl 2-alkynyl, amyl 3-alkynyl, hex-1-alkynyl, hex-2-alkynyl, hex-3-alkynyl, hex-4-alkynyl. As used herein, a "$C_6$-$C_{30}$ (or $C_6$-$C_{18}$) alkynyl" group means a radical having from 6 to 30 (or 6 to 18) carbon atoms in a straight or branched arrangement. In some embodiments, a "$C_6$-$C_{30}$ (or $C_6$-$C_{18}$) alkynyl" group means a radical having from 6 to 30 (or 6 to 18) carbon atoms in a straight arrangement. In some embodiments, a "$C_6$-$C_{30}$ (or $C_6$-$C_{18}$) alkynyl" group means a radical having from 6 to 30 (or 6 to 18) carbon atoms in a branched arrangement.

Where suitable substituents are not specifically enumerated, exemplary substituents include, but are not limited to: $C_{1-5}$alkyl, $C_{1-5}$hydroxyalkyl, $C_{1-5}$haloalkyl, $C_{1-5}$alkoxy, $C_{1-5}$ haloalkoxy, halogen, hydroxyl, cyano, amino, —CN, —$NO_2$, —$OR^{c1}$, —$NR^{a1}R^{b1}$, —$S(O)_iR^{a1}$, —$NR^{a1}S(O)_iR^{b1}$, —$S(O)_iNR^{a1}R^{b1}$, —C(=O)$OR^{a1}$, —OC(=O)$OR^{a1}$, —C(=S)$OR^{a1}$, —O(C=S)$R^{a1}$, —C(=O)$NR^{a1}R^{b1}$, —$NR^{a1}$C(=O)$R^{b1}$, —C(=S)$NR^{a1}R^{b1}$, —C(=O)$R^{a1}$, —C(=S)$R^{a1}$, $NR^{a1}$C(=S)$R^{b1}$, —O(C=O)$NR^{a1}R^{b1}$, —$NR^{a1}$(C=S)$OR^{b1}$, —O(C=S)$NR^{a1}R^{b1}$, —$NR^{a1}$(C=O)$NR^{a1}R^{b1}$, —$NR^{a1}$(C=S)$NR^{a1}R^{b1}$, phenyl, or 5-6 membered heteroaryl. Each $R^{a1}$ and each $R^{b1}$ are independently selected from —H and $C_{1-5}$alkyl, optionally substituted with hydroxyl or $C_{1-3}$alkoxy; $R^{c1}$ is —H, $C_{1-5}$haloalkyl or $C_{1-5}$alkyl, wherein the $C_{1-5}$alkyl is optionally substituted with hydroxyl or $C_1$-$C_3$alkoxy.

The term "pharmaceutically acceptable" means that a carrier, excipient, salt, etc., which is usually chemically or physically compatible with the other components that make up a pharmaceutical dosage form and physiologically compatible with the receptor. The term "pharmaceutically acceptable salt" means acid and/or base salts of the compounds described in the patent in association with inorganic and/or organic acids and bases, also including amphoteric ionic salts (inner salts) and quaternary ammonium salts, such as alkyl ammonium salts. These salts can be obtained directly in the final isolation and purification of the compounds. These salts also can be obtained by mixing the above-mentioned compound with acid or base as appropriate (for example, an equivalent amount). These salts may be collected by filtration as precipitation in solution, or by recovery after evaporation of the solvent, or by freeze-drying after reaction in aqueous media. The salts described in the patent may be compounds of hydrochloride, sulfate, citrate, benzoate, hydrobromate, hydrofluorate, phosphate, acetate, propionate, succinate, oxalate, malate, succinate, fumarate, maleate, tartrate or trifluoroacetate.

The present disclosure provides a novel ionizable lipid, whose hydrophilic center is composed of four tertiary amine atoms, and hydrophobic tail is composed of four saturated or unsaturated fat chains. The novel ionizable lipid provided by the present disclosure is positively charged in an acidic environment, and almost un-charged in a neutral and physiological pH environment. Nucleic acid drugs can be transferred by using this property in an acidic buffer system. After the nucleic acid drugs are loaded, the system is adjusted to neutral, so that the lipid nanoparticles are uncharged to avoid adsorption by plasma proteins and achieve higher delivery efficiency and safety.

The scheme of the present disclosure is explained below in combination with embodiments. Those skilled in the field will understand that the following embodiments are intended only to illustrate the present disclosure and should not be regarded as limiting the scope of the present disclosure. If the specific technology or conditions are not specified in the embodiment, the technology or conditions described in the literature in the field or the product specification shall be followed. Reagents or instruments used without manufacturer are conventional products that can be purchased in the market.

EXAMPLES

Abbreviations
DCM 1,2-Dichloromethane
DIPEA N-ethyl-N-isopropylpropan-2-amine
EA Ethyl acetate
eq equivalent
EtOH Ethanol
MeOH Methanol
PE Petroleum ether
TEA Triethyl amine
TFA Trifluoroacetic acid Example 1 Synthesis of Compound II-1

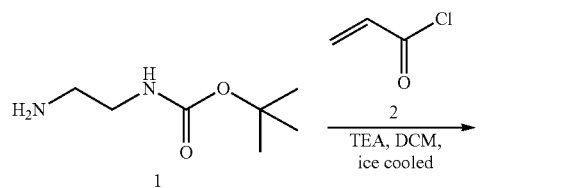

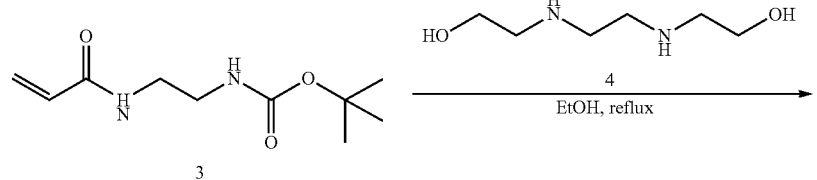

-continued

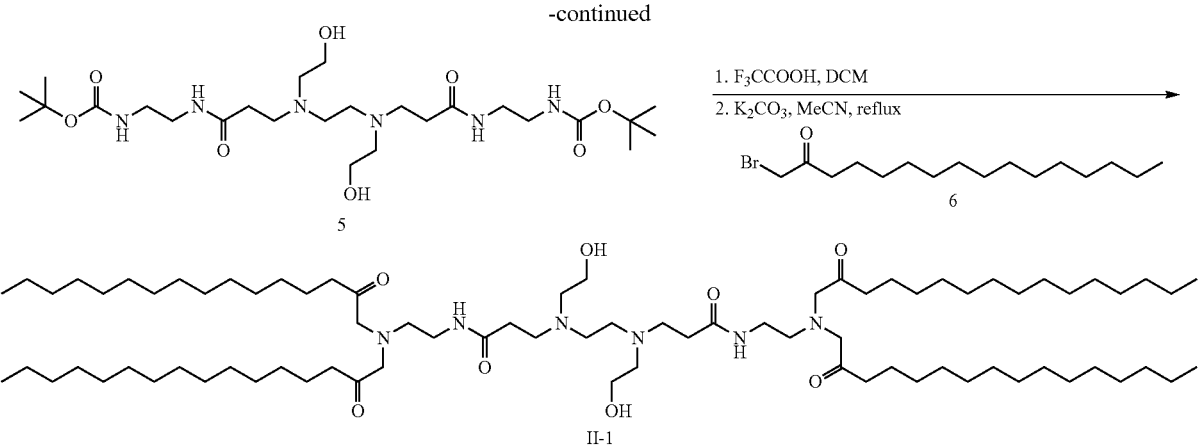

(1) Synthesis of Compound 3

N-Boc-1,2-ethylenediamine (1.0 eq) and TEA (2.0 eq) were added to a single-necked bottle, dissolved in an appropriate amount of anhydrous DCM, and stirred evenly in an ice-water bath. Separately, acryloyl chloride (1.2 eq) was dissolved in an appropriate amount of anhydrous DCM and added to a constant pressure dropping funnel, and the flow rate was controlled to make it dropwise into the above single-necked bottle and reacted in an ice-water bath for 6 h. The reaction solvent was spin-dried, and the crude product was purified by silica gel column chromatography (DCM:MeOH=50:1), concentrated and dried to obtain a white solid 3 with a yield of 90.5%.

(2) Synthesis of Compound 5

Add N,N'-bis(2-hydroxyethyl)ethylenediamine (1.0 eq) and compound 3 (2.0 eq) to a single-necked flask and dissolve in an appropriate amount of anhydrous ethanol. Add a condenser tube to the single-necked flask and place it in an oil bath at 80° C. Stir at medium reflux for 12 h. The reaction solvent was spin-dried, and the crude product was purified by silica gel column chromatography (DCM:MeOH=15:1, 0.5% ammonia water), concentrated and dried to obtain pale-yellow solid 5 with a yield of 85.3%.

(3) Synthesis of II-1

Compound 5 was dissolved in DCM, a sufficient amount of TFA was added under stirring, and the reaction was carried out at room temperature for 6 h. TFA/DCM was spun down to give a yellow oil. The above-mentioned oily substance is dissolved in an appropriate amount of acetonitrile, a sufficient amount of anhydrous potassium carbonate is added under stirring, and the mixture is stirred at room temperature until the reaction solvent is alkaline. 1-Bromo-2-hexadecanone (6.0eq) was added to the above reaction solution, a condenser was added to the single-necked flask, and the mixture was refluxed and stirred in an oil bath at 90° C. for 36 h. The reaction solvent was spin-dried, and the crude product was purified by silica gel column chromatography (DCM:MeOH=20:1, 0.5% ammonia water), concentrated and dried to obtain yellow oil II-1 with a yield of 76.8%.

Example 2 Synthesis of Compound III-1

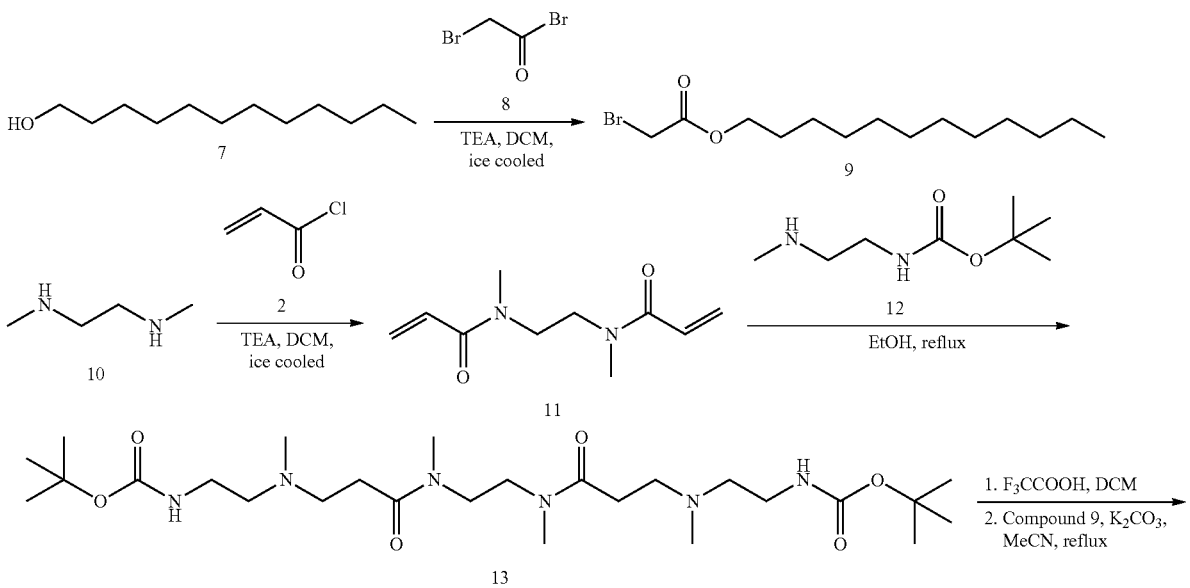

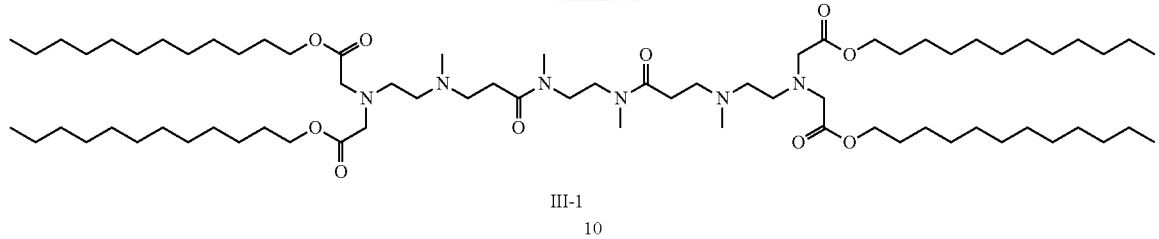

III-1

(1) Synthesis of Compound 9

Dodecanol (1.0 eq) and TEA (2.0 eq) were added to a single-necked bottle, dissolved in an appropriate amount of anhydrous DCM, and stirred evenly in an ice-water bath. In addition, bromoacetyl bromide (1.2eq) was dissolved in an appropriate amount of anhydrous DCM and added to a constant pressure dropping funnel, and the flow rate was controlled to make it dropwise into the above single-necked bottle, and reacted in an ice-water bath for 6 h. The reaction solvent was spin-dried, the crude product was purified by silica gel column chromatography (PE:DCM=1:1), concentrated and dried to obtain a colorless liquid 9 with a yield of 86.1%.

(2) Synthesis of Compound 11

Add N,N'-dimethylethylenediamine (1.0eq) and TEA (3.0eq) to a single-necked bottle, dissolve in an appropriate amount of anhydrous DCM, and stir evenly in an ice-water bath. Separately, acryloyl chloride (2.5eq) was dissolved in an appropriate amount of anhydrous DCM and added to a constant pressure dropping funnel, and the flow rate was controlled to make it dropwise into the above single-necked bottle, and reacted in an ice-water bath for 6 h. The reaction solvent was spin-dried, the crude product was purified by silica gel column chromatography (DCM:MeOH=60:1), and concentrated to dryness to obtain white solid 11 with a yield of 92.5%.

(3) Synthesis of compound 13:

Add compound 11 (1.0eq) and tert-butyl 2-(methylamino) ethylcarbamate (2.0eq) to a single-necked flask and dissolve in an appropriate amount of anhydrous ethanol, add a condenser tube to the single-necked flask and reflux in an oil bath at 80° C. Stir for 12 h. The reaction solvent was spin-dried, and the crude product was purified by silica gel column chromatography (DCM:MeOH=20:1, 0.5% ammonia water), concentrated and dried to obtain yellow semi-solid 13 with a yield of 89.1%.

(4) Synthesis of III-1

Compound 13 was dissolved in DCM, a sufficient amount of TFA was added under stirring, and the reaction was carried out at room temperature for 6 h. TFA/DCM was spun down to give a yellow oil. The above-mentioned oily substance is dissolved in an appropriate amount of acetonitrile, a sufficient amount of anhydrous potassium carbonate is added under stirring, and the mixture is stirred at room temperature until the reaction solvent is alkaline. Compound 9 (6.0eq) was added to the above reaction solution, a single-necked flask was added with a condenser tube, and the mixture was refluxed and stirred in an oil bath at 90° C. for 36 h. The reaction solvent was spin-dried, and the crude product was purified by silica gel column chromatography (DCM:MeOH=20:1, 0.5% ammonia water), concentrated and dried to obtain yellow oil III-1 with a yield of 70.8%.

Example 3 Synthesis of Compound III-2

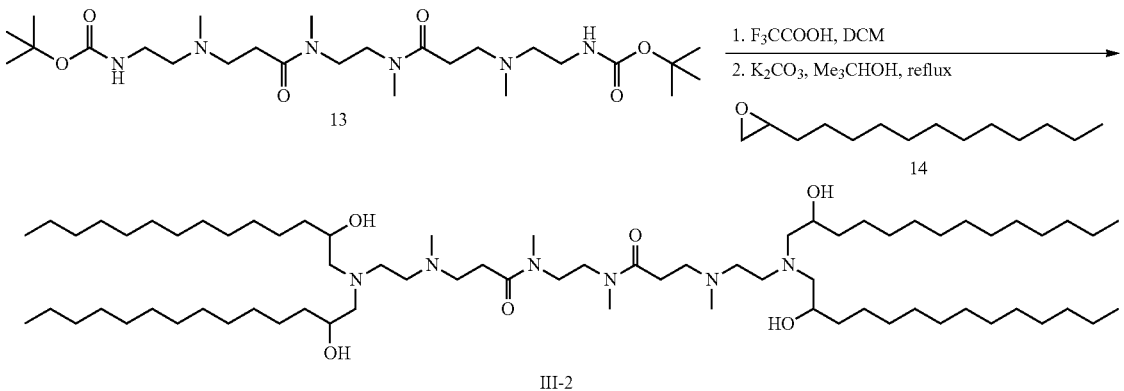

III-2

Compound 13 was dissolved in DCM, a sufficient amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. 1,2-Epoxytetradecane (6.0eq) was added to the above reaction solution, a condenser was added to the single-necked flask, and the mixture was refluxed and stirred in an oil bath at 90° C. for 36 h. The reaction solvent was spin-dried, and the crude product was purified by silica gel column chromatography (DCM:MeOH=15:1, 0.5% ammonia water), concentrated and dried to obtain yellow oil III-2 with a yield of 75.1%.

Example 4 Synthesis of Compound III-3

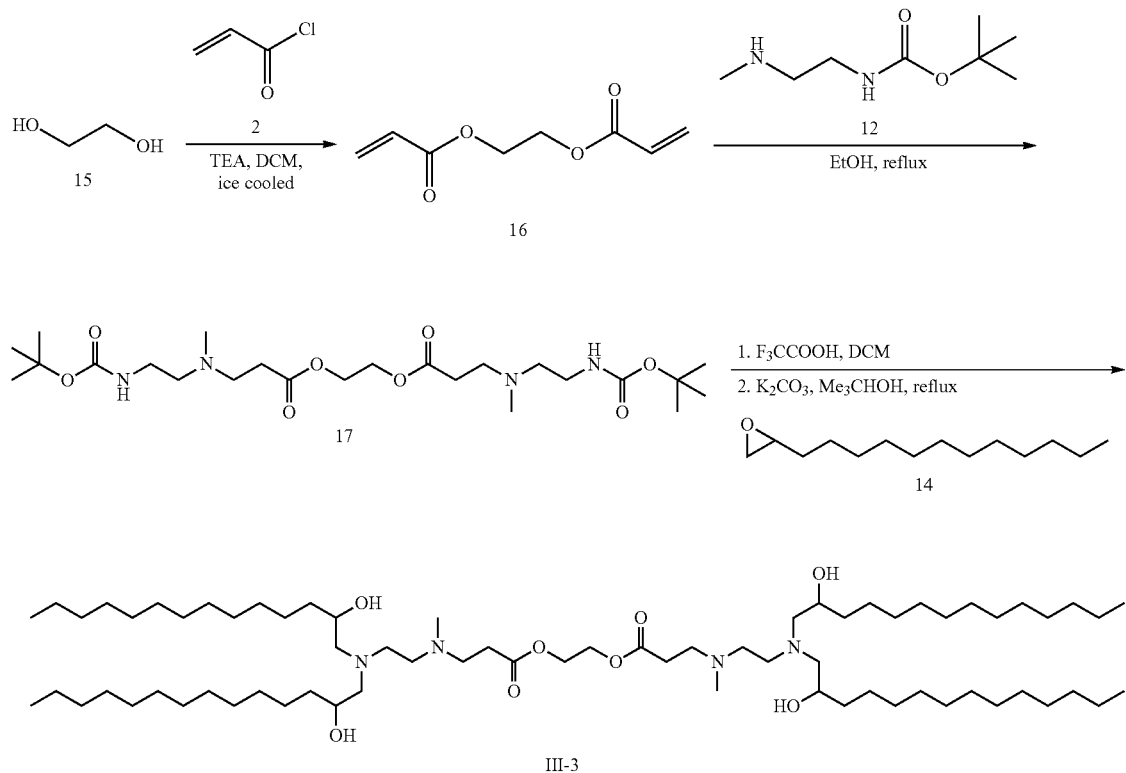

(1) Synthesis of Compound 16

Add ethylene glycol (1.0 eq) and TEA (3.0 eq) to a single-necked bottle, dissolve in an appropriate amount of anhydrous DCM, and stir evenly in an ice-water bath. Separately, acryloyl chloride (2.5eq) was dissolved in an appropriate amount of anhydrous DCM and added to a constant pressure dropping funnel, and the flow rate was controlled to make it dropwise into the above single-necked bottle, and reacted in an ice-water bath for 6 h. The reaction solvent was spin-dried, the crude product was purified by silica gel column chromatography (DCM:MeOH=80:1), concentrated and dried to obtain colorless liquid 16 with a yield of 87.5%.

(2) Synthesis of Compound 17

Add compound 16 (1.0eq) and tert-butyl 2-(methylamino) ethylcarbamate (2.0eq) to a single-necked flask and dissolve in an appropriate amount of anhydrous ethanol. Add a condenser tube to the single-necked flask and reflux in an oil bath at 80° C. Stir for 12 h. The reaction solvent was spin-dried, and the crude product was purified by silica gel column chromatography (DCM:MeOH=25:1, 0.5% ammonia water), concentrated and dried to obtain light yellow oily product 17 with a yield of 84.4%.

(3) Synthesis of III-3

Compound 17 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. 1,2-Epoxytetradecane (6.0eq) was added to the above reaction solution, a condenser was added to the single-necked flask, and the mixture was refluxed and stirred in an oil bath at 90° C. for 36 h. The reaction solvent was spin-dried, and the crude product was purified by silica gel column chromatography (DCM:MeOH=25:1, 0.5% ammonia water), concentrated and dried to obtain a pale-yellow oily product III-3 with a yield of 67.8%.

Example 5 Synthesis of Compound VI-1

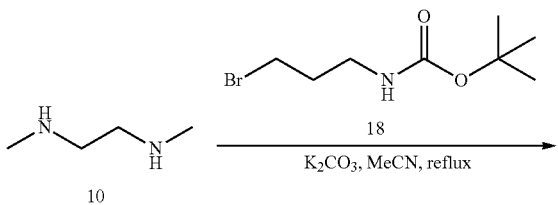

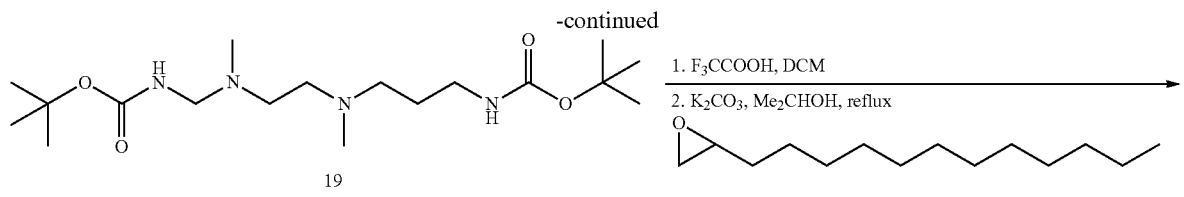

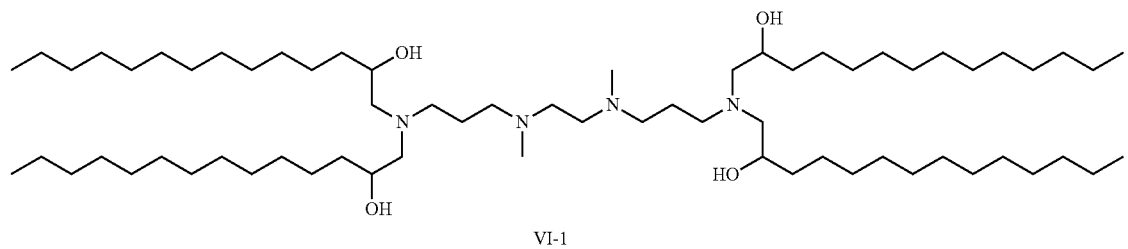

(1) Synthesis of Compound 19

Add N,N'-dimethylethylenediamine (1.0eq) and N-Boc-3-aminopropyl bromide (2.5eq) to a single-necked bottle and dissolve in appropriate amount of acetonitrile. Add a condenser tube to the single-necked bottle and heat it at 90° C. The bath was refluxed and stirred for 12 h. The reaction solvent was spin-dried, and the crude product was purified by silica gel column chromatography (DCM:MeOH=25:1, 0.5% ammonia water), concentrated and dried to obtain light yellow oily product 17 with a yield of 78.8%.

(2) Synthesis of VI-1

Compound 19 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. 1,2-Epoxytetradecane (6.0eq) was added to the above reaction solution, a condenser was added to the single-necked flask, and the mixture was refluxed and stirred in an oil bath at 90° C. for 36 h. The reaction solvent was spin-dried, the crude product was purified by silica gel column chromatography (DCM:MeOH=15:1, 0.5% ammonia water), concentrated and dried to obtain a yellow oil VI-1 with a yield of 70.8%.

Example 6 Synthesis of Compound II-7

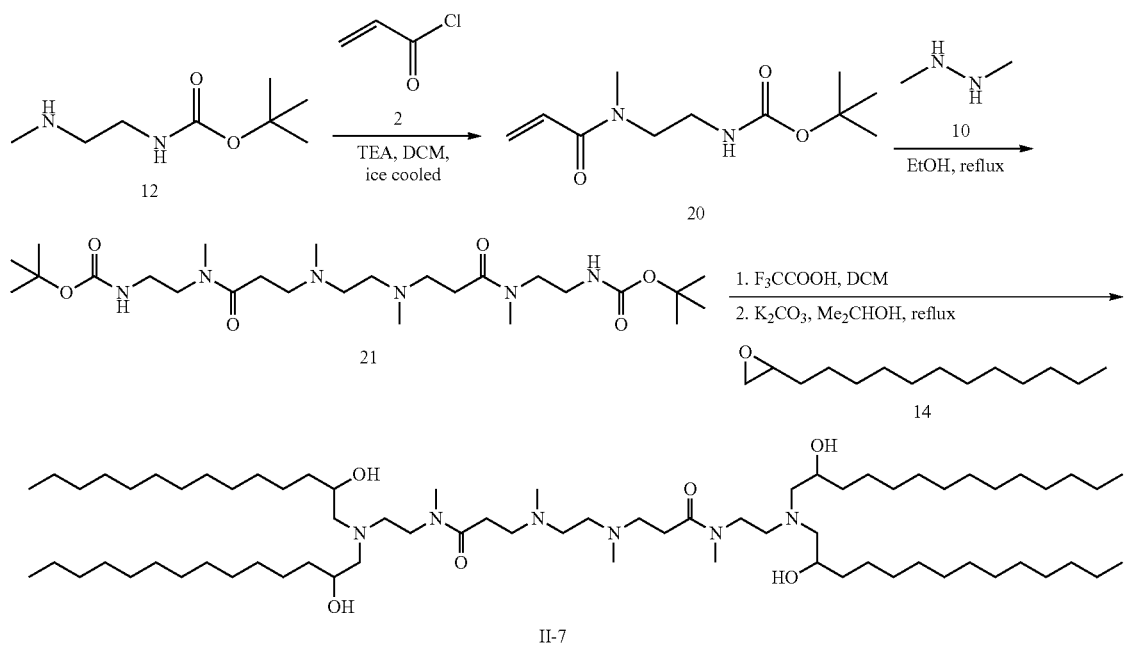

(1) Synthesis of Compound 20

In a single-neck flask, add tert-butyl 2-(methylamino)ethyl-carbamate (1.0 eq) and TEA (3.0 eq), dissolve in an appropriate amount of anhydrous DCM, and stir evenly in an ice-water bath. Separately, acryloyl chloride (1.2eq) was dissolved in an appropriate amount of anhydrous DCM and added to a constant pressure dropping funnel, and the flow rate was controlled to make it dropwise into the above single-necked bottle, and reacted in an ice-water bath for 6 h. The reaction solvent was spin-dried, and the crude product was purified by silica gel column chromatography (DCM:MeOH=60:1), concentrated and dried to obtain a white semi-solid 20 with a yield of 89.5%.

(2) Synthesis of Compound 21

Add N,N'-dimethylethylenediamine (1.0eq) and compound 20 (2.0eq) to a single-necked flask and dissolve in an appropriate amount of anhydrous ethanol. Add a condenser tube to the single-necked flask and reflux and stir in an oil bath at 80° C. for 12 h. The reaction solvent was spin-dried, and the crude product was purified by silica gel column chromatography (DCM:MeOH=20:1, 0.5% ammonia water), concentrated and dried to obtain yellow oil 21 in a yield of 84.0%.

(3) Synthesis of II-7

Compound 21 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. 1,2-Epoxytetradecane (6.0eq) was added to the above reaction solution, a condenser was added to the single-necked flask, and the mixture was refluxed and stirred in an oil bath at 90° C. for 36 h. The reaction solvent was spin-dried, and the crude product was purified by silica gel column chromatography (DCM:MeOH=20:1, 0.5% ammonia water), concentrated and dried to obtain yellow oil II-7 with a yield of 69.1%.

Example 7 Synthesis of Compound VI-2

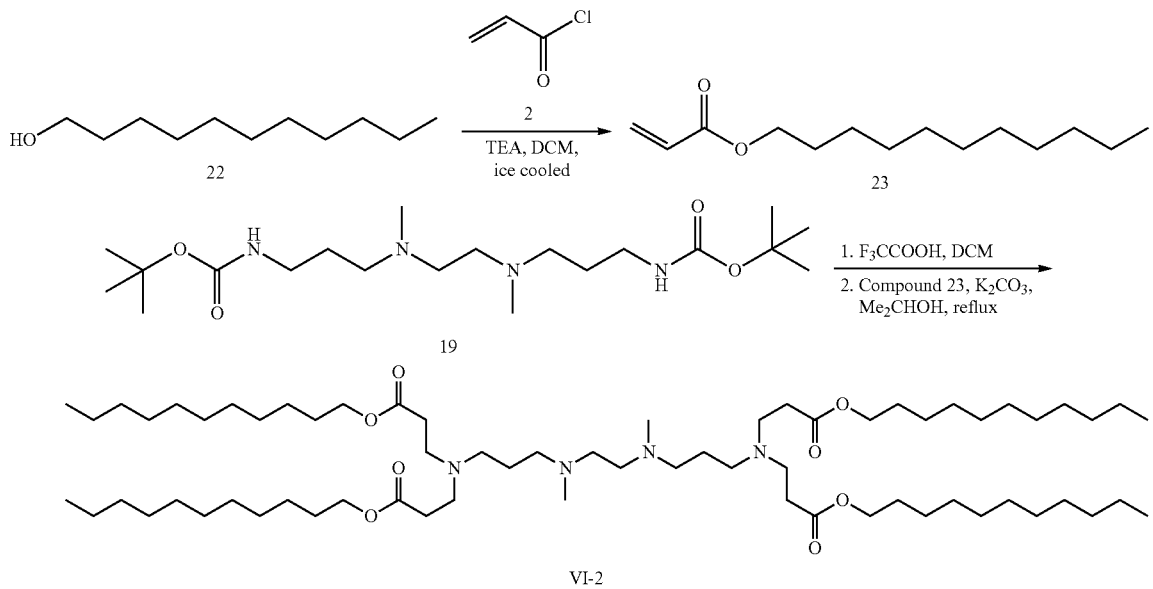

(1) Synthesis of Compound 23

Undecyl alcohol (1.0 eq) and TEA (2.0 eq) were added to a single-necked bottle, dissolved in an appropriate amount of anhydrous DCM, and stirred evenly in an ice-water bath. Separately, acryloyl chloride (1.2eq) was dissolved in an appropriate amount of anhydrous DCM and added to a constant pressure dropping funnel, and the flow rate was controlled to make it dropwise into the above single-necked bottle, and reacted in an ice-water bath for 6 h. The reaction solvent was spin-dried, and the crude product was purified by silica gel column chromatography (PE:EA=2:1), concentrated and dried to obtain a colorless liquid 23 with a yield of 90.0%.

(2) Synthesis of VI-2

Compound 19 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. Compound 23 (6.0eq) was added to the above reaction solution, a single-necked flask was added with a condenser tube, and the mixture was refluxed and stirred in an oil bath at 90° C. for 36 h. The reaction solvent was spin-dried, and the crude product was purified by silica gel column chromatography (DCM:MeOH=25:1, 0.5% ammonia water), concentrated and dried to obtain light yellow oil VI-2 with a yield of 74.1%.

Example 8 Synthesis of Compound VI-3

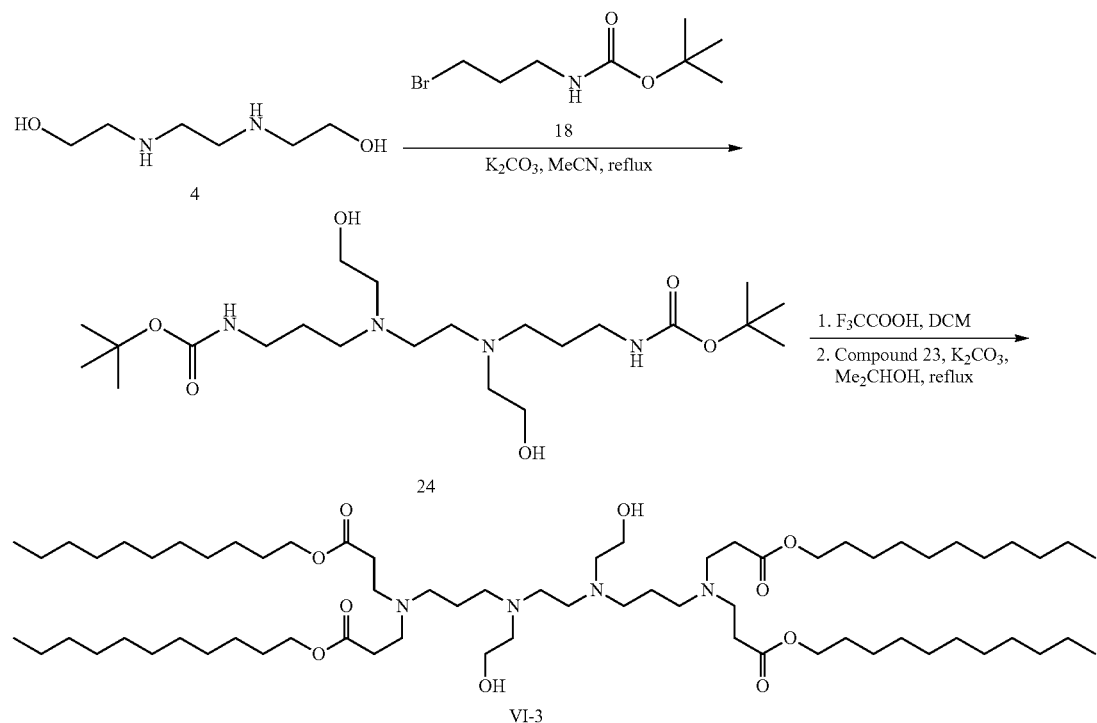

(1) Synthesis of Compound 24

Add N,N'-bis(2-hydroxyethyl)ethylenediamine (1.0eq) and N-Boc-3-aminopropyl bromide (2.5eq) to a single-necked bottle and dissolved in an appropriate amount of acetonitrile, add a condenser to the single-necked bottle, then reflux and stir in an oil bath at 90° C. for 12 h. The reaction solvent was spin-dried, and the crude product was purified by silica gel column chromatography (DCM:MeOH=20:1, 0.5% ammonia water), concentrated and dried to obtain pale-yellow oily compound 24 with a yield of 71.2%.

(2) Synthesis of VI-3

Compound 24 was dissolved in DCM, an appropriate amount of TFA was added under stirring, and the reaction was carried out at room temperature for 6 h. TFA/DCM was spin-dried, obtaining a yellow oily product. The above-mentioned oily substance is dissolved in an appropriate amount of isopropanol, a sufficient amount of anhydrous potassium carbonate is added under stirring, and the mixture is stirred at room temperature until the reaction solvent is alkaline. Compound 23 (6.0eq) was added to the above reaction solution, a single-necked flask was added with a condenser, and the mixture was refluxed and stirred in an oil bath at 90° C. for 36 h. The reaction solvent was spin-dried, the crude product was purified by silica gel column chromatography (DCM:MeOH=15:1, 0.5% ammonia water), concentrated and dried to obtain pale-yellow oil VI-3 with a yield of 69.5%.

Example 9 Synthesis of Compound II-11

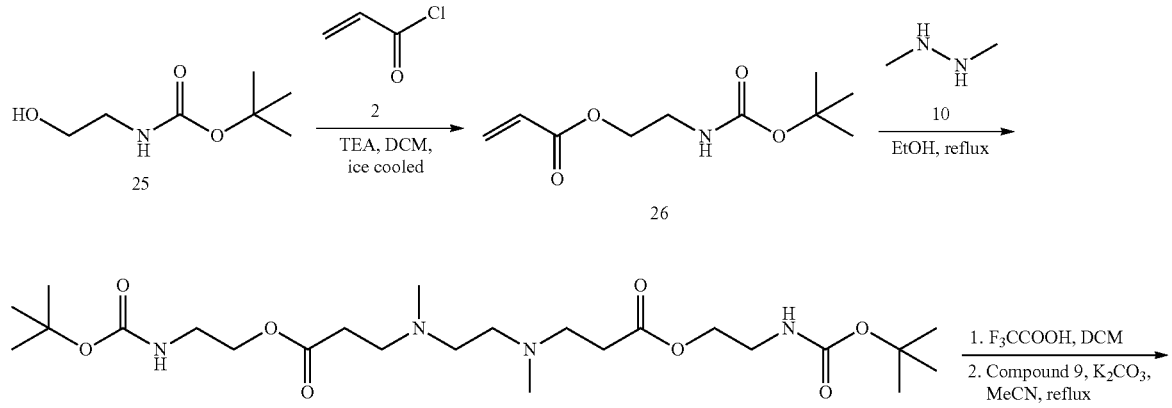

-continued

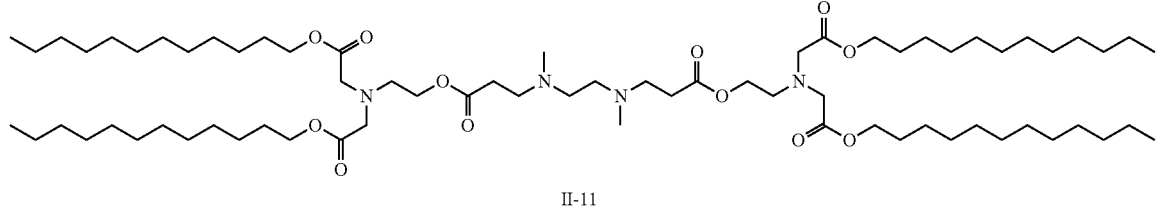

II-11

(1) Synthesis of Compound 26

N-Boc-ethanolamine (1.0eq) and TEA (2.0eq) were added to a single-necked flask, dissolved in an appropriate amount of anhydrous DCM, and stirred evenly in an ice-water bath. Separately, acryloyl chloride (1.2eq) was dissolved in an appropriate amount of anhydrous DCM and added to a constant pressure dropping funnel, and the flow rate was controlled to make it dropwise into the above single-necked bottle and reacted in an ice-water bath for 6 h. The reaction solvent was spin-dried, the crude product was purified by silica gel column chromatography (DCM:MeOH=70:1), concentrated and dried to obtain white semi-solid compound 26 with a yield of 85.4%.

(2) Synthesis of Compound 27

Add N,N'-dimethylethylenediamine (1.0eq) and compound 26 (2.0eq) to a single-necked flask and dissolve in an appropriate amount of anhydrous ethanol. Add a condenser to the single-necked flask, then reflux and stir it in an oil bath at 80° C. for 12 h. The reaction solvent was spin-dried, the crude product was purified by silica gel column chromatography (DCM: MeOH=25:1, 0.5% ammonia water), concentrated and dried to obtain pale-yellow semi-solid compound 27 with a yield of 82.4%.

(3) Synthesis of II-11

Compound 27 was dissolved in DCM, a sufficient amount of TFA was added under stirring, and the reaction was carried out at room temperature for 6 h. TFA/DCM was spun down to give a yellow oily product. The above-mentioned oily substance is dissolved in an appropriate amount of acetonitrile, a sufficient amount of anhydrous potassium carbonate is added under stirring, and the mixture is stirred at room temperature until the reaction solvent is alkaline. Compound 9 (6.0eq) was added to the above reaction solution, a single-necked flask was added with a condenser, and the mixture was refluxed and stirred in an oil bath at 90° C. for 36 h. The reaction solvent was spin-dried, and the crude product was purified by silica gel column chromatography (DCM:MeOH=30:1, 0.5% ammonia water), concentrated and dried to obtain pale-yellow oily compound II-11 with a yield of 72.1%.

Example 10 Synthesis of Compound II-13

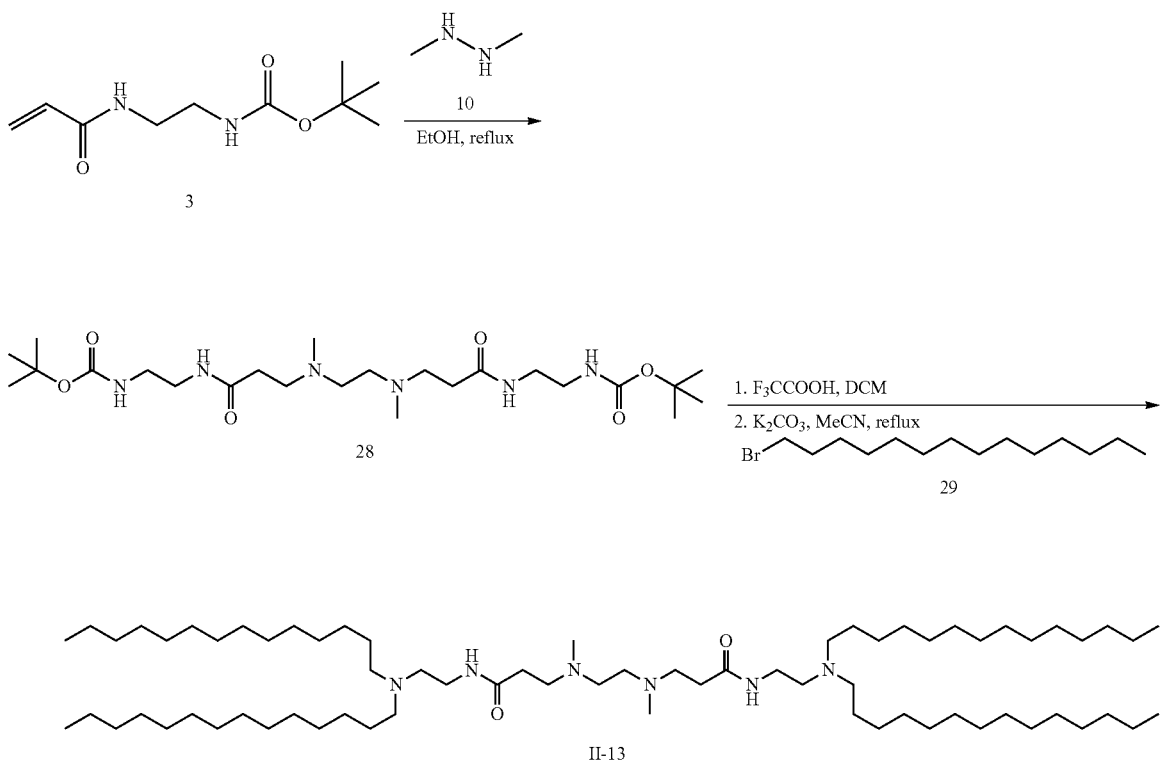

(1) Synthesis of Compound 28

Add N,N'-dimethylethylenediamine (1.0eq) and compound 3 (2.0eq) to a single-necked flask and dissolve in an appropriate amount of anhydrous ethanol. Add a condenser to the single-necked flask, then reflux and stir it in an oil bath at 80° C. for 12 h. The reaction solvent was spin-dried, the crude product was purified by silica gel column chromatography (DCM: MeOH=20:1, 0.5% ammonia water), concentrated and dried to obtain a pale-yellow solid compound 28 with a yield of 85.9%.

(2) Synthesis of II-13

Compound 28 was dissolved in DCM, a sufficient amount of TFA was added under stirring, and the reaction was carried out at room temperature for 6 h. TFA/DCM was spin-dried to give a yellow oily product. The above-mentioned oily substance is dissolved in an appropriate amount of acetonitrile, a sufficient amount of anhydrous potassium carbonate is added under stirring, and the mixture is stirred at room temperature until the reaction solvent is alkaline. Bromotetradecane (6.0eq) was added to the above reaction solution, a condenser was added to the single-neck flask, and the mixture was refluxed and stirred in an oil bath at 90° C. for 36 h. The reaction solvent was spin-dried, and the crude product was purified by silica gel column chromatography (DCM: MeOH=25:1, 0.5% ammonia water), concentrated and dried to obtain pale-yellow semi-solid compound II-13 with a yield of 75.5%.

Example 11 Synthesis of Compound II-22

(1) Synthesis of Compound 31

Add dodecanol (1.0eq), epichlorohydrin (2.0eq), sodium hydroxide (2.0eq), tetrabutylammonium bromide, water and cyclohexane to a single-necked flask to form a white emulsion, at room temperature The reaction was stirred for 4 h. After the reaction, suction filtration and wash the filter cake with dichloromethane 2-3 times, the filtrate is dried with anhydrous sodium sulfate, the solvent is spin-dried, and the crude product is purified by silica gel column chromatography (PE/EA=8:1-4:1), a colorless liquid 31 was obtained.

(2) Synthesis of II-22

Compound 28 was dissolved in DCM, a sufficient amount of TFA was added under stirring, and the reaction was carried out at room temperature for 6 h. TFA/DCM was spin-dried to give a yellow oily product. The above-mentioned oily substance is dissolved in an appropriate amount of isopropanol, a sufficient amount of anhydrous potassium carbonate is added under stirring, and the mixture is stirred at room temperature until the reaction solvent is alkaline. Compound 31 (6.0eq) was added to the above reaction solution, a single-neck flask was added with a condenser tube, and the mixture was refluxed and stirred in an oil bath at 90° C. for 36 h. The reaction solvent was spin-dried, and the crude product was purified by silica gel column chromatography (DCM:MeOH=25:1, 0.5% ammonia water), concentrated and dried to obtain a pale-yellow oily compound II-22 with a yield of 69.5%.

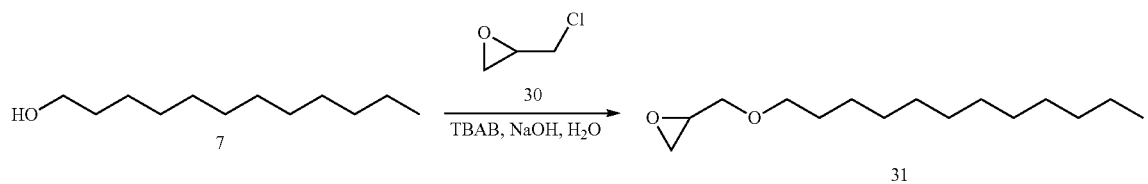

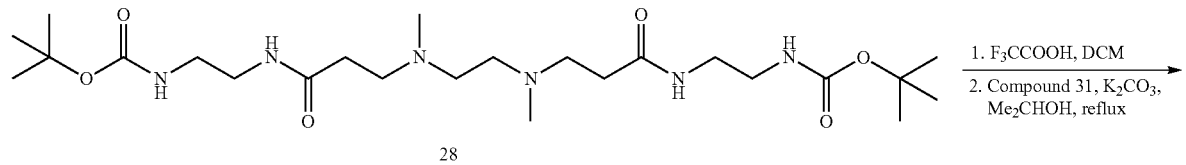

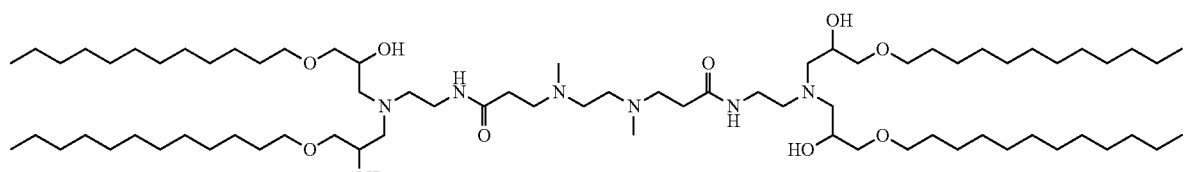

Example 12 Synthesis of Compound II-5

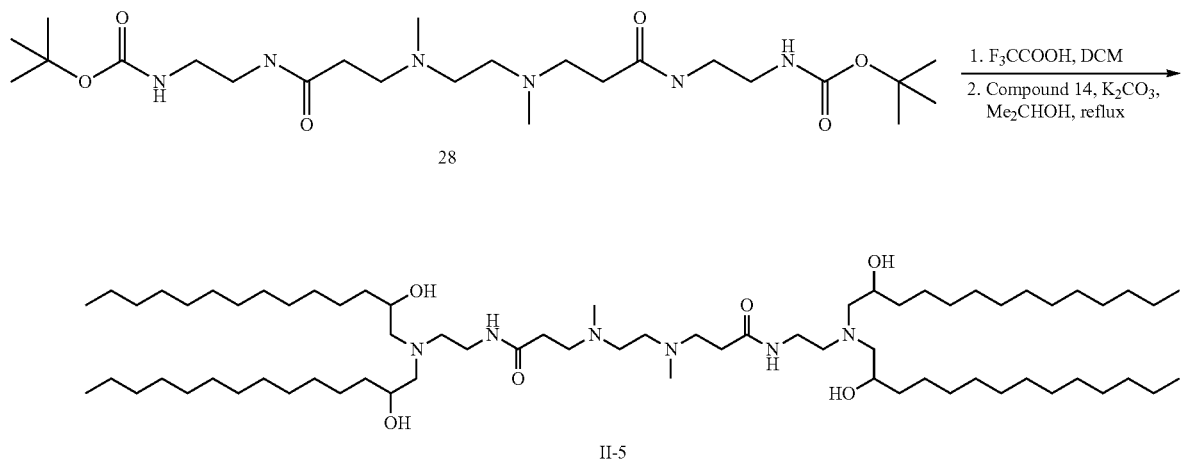

Synthesis of II-5

Compound 28 was dissolved in DCM, a sufficient amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. Compound 14 (6.0eq) was added to the above reaction solution, a single-neck flask was added with a condenser tube, and the mixture was refluxed and stirred in an oil bath at 90° C. for 36 h. The reaction solvent was spin-dried, and the crude product was purified by silica gel column chromatography (DCM:MeOH=15:1, 0.5% ammonia water), concentrated and dried to obtain light yellow oil II-5 with a yield of 52.0%.

Example 13 Synthesis of Compound II-18

Synthesis of II-18

Compound 27 was dissolved in DCM, a sufficient amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. Compound 32 (6.0eq) was added to the above reaction solution, a condenser was added to the single-neck flask, and the mixture was refluxed and stirred in an oil bath at 90° C. for 36 h. The reaction solvent was spin-dried, and the crude product was purified by silica gel column chromatography (DCM:MeOH=15:1, 0.5% ammonia water), concentrated and dried to obtain light yellow oil II-18 with a yield of 61.7%.

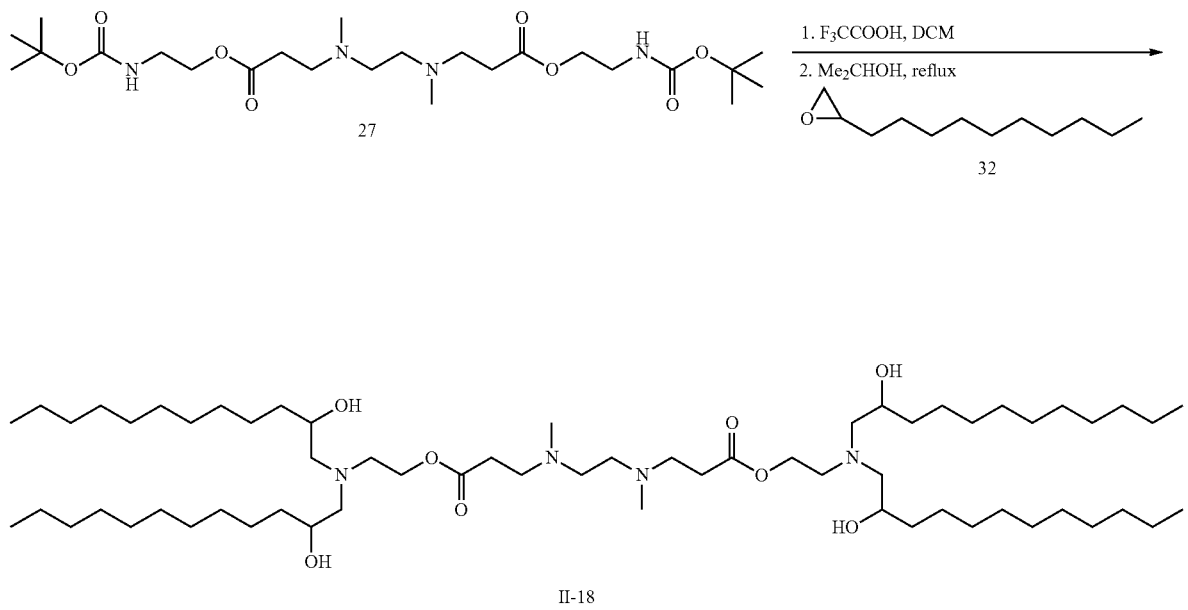

Example 14 Synthesis of Compound II-24

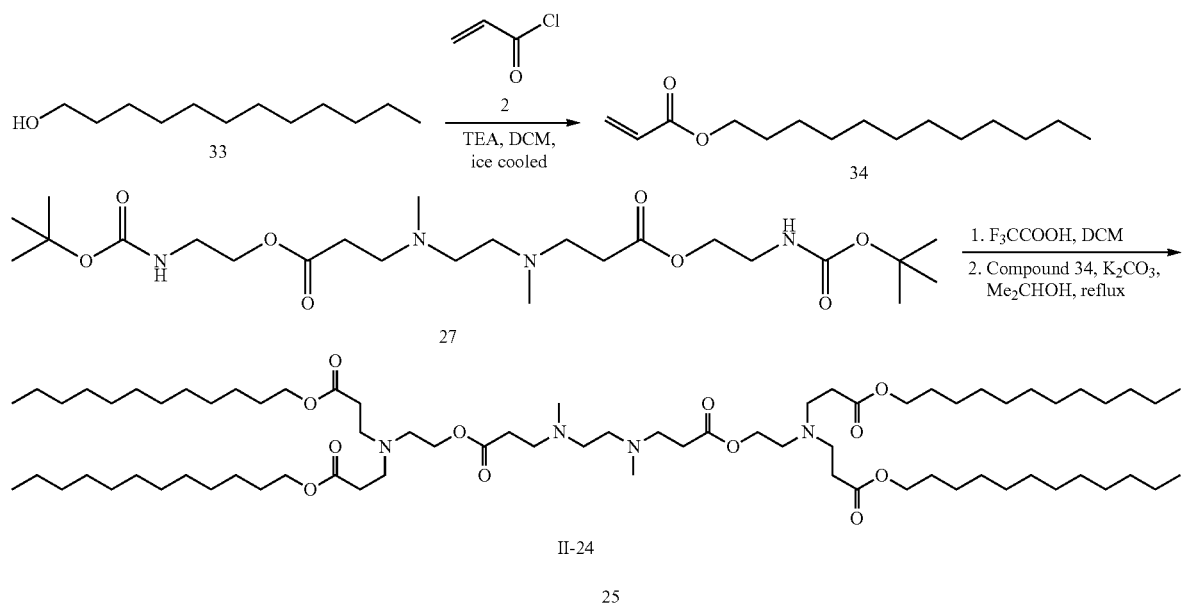

(1) Synthesis of Compound 34

Dodecanol (1.0 eq) and TEA (2.0 eq) were added to a single-necked bottle, dissolved in an appropriate amount of anhydrous DCM, and stirred evenly in an ice-water bath. Separately, acryloyl chloride (1.2eq) was dissolved in an appropriate amount of anhydrous DCM and added to a constant pressure dropping funnel, and the flow rate was controlled to make it dropwise into the above single-necked bottle and reacted in an ice-water bath for 6 h. The reaction solvent was spin-dried, the crude product was purified by silica gel column chromatography (PE:EA=2:1), concentrated and dried to obtain a colorless liquid 34 with a yield of 91.0%.

(2) Synthesis of II-24

Compound 27 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of isopropanol, a sufficient amount of anhydrous potassium carbonate is added under stirring, and the mixture is stirred at room temperature until the reaction solvent is alkaline. Compound 34 (6.0eq) was added to the above reaction solution, a single-necked flask was added with a condenser tube, and the mixture was refluxed and stirred in an oil bath at 90° C. for 36 h. The reaction solvent was spin-dried, and the crude product was purified by silica gel column chromatography (DCM:MeOH=25:1, 0.5% ammonia water), concentrated and dried to obtain pale-yellow oil II-24 with a yield of 70.2%.

Example 15 Synthesis of Compound II-25

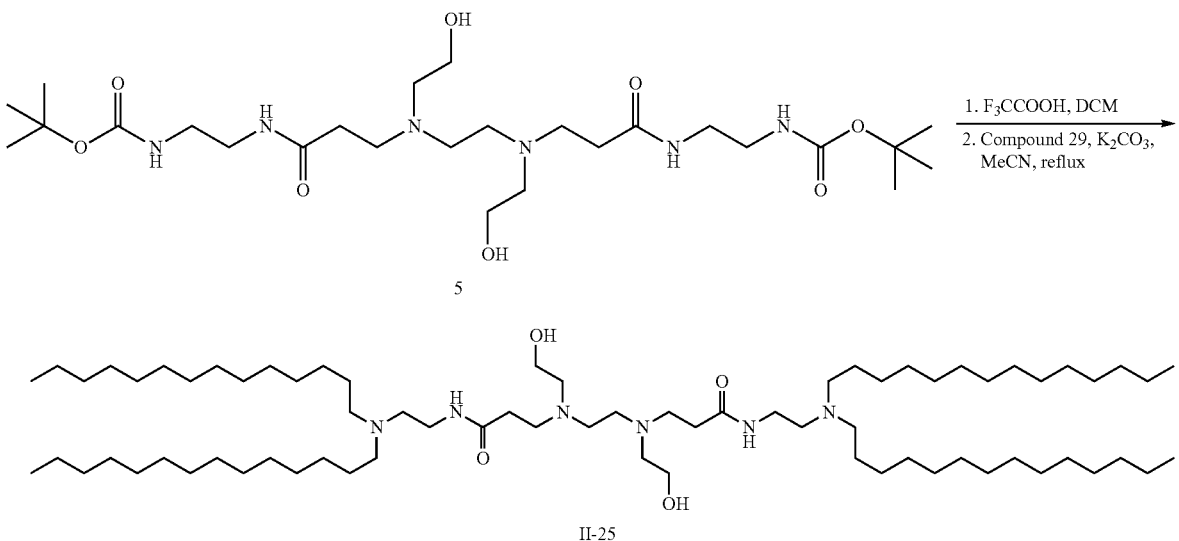

Synthesis of II-25

Compound 5 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of acetonitrile, a sufficient amount of anhydrous potassium carbonate is added under stirring, and the mixture is stirred at room temperature until the reaction solvent is alkaline. Compound 29 (6.0eq) was added to the above reaction solution, a condenser was added to the single-necked flask, and the mixture was refluxed and stirred in an oil bath at 90° C. for 36 h. The reaction solvent was spin-dried, the crude product was purified by silica gel column chromatography (DCM:MeOH=20:1, 0.5% ammonia water), concentrated and dried to obtain light yellow oil II-25 with a yield of 65.3%.

Example 16 Synthesis of Compound III-11 column chromatography (DCM:MeOH=80:1), concentrated and dried to obtain a white solid 36 with a yield of 89.6%.

(2) Synthesis of Compound 37

Compound 36 (1.0eq) and Boc-ethylenediamine (2.5eq) were added to the single-necked flask and dissolved in an appropriate amount of absolute ethanol. A condenser was added to the single-necked flask, and the mixture was refluxed and stirred in an oil bath at 80° C. for 12 h. The reaction solvent was spin-dried, and the crude product was purified by silica gel column chromatography (DCM:MeOH=15:1, 0.5% ammonia water), concentrated and dried to obtain light yellow oily product 17 with a yield of 80.4%.

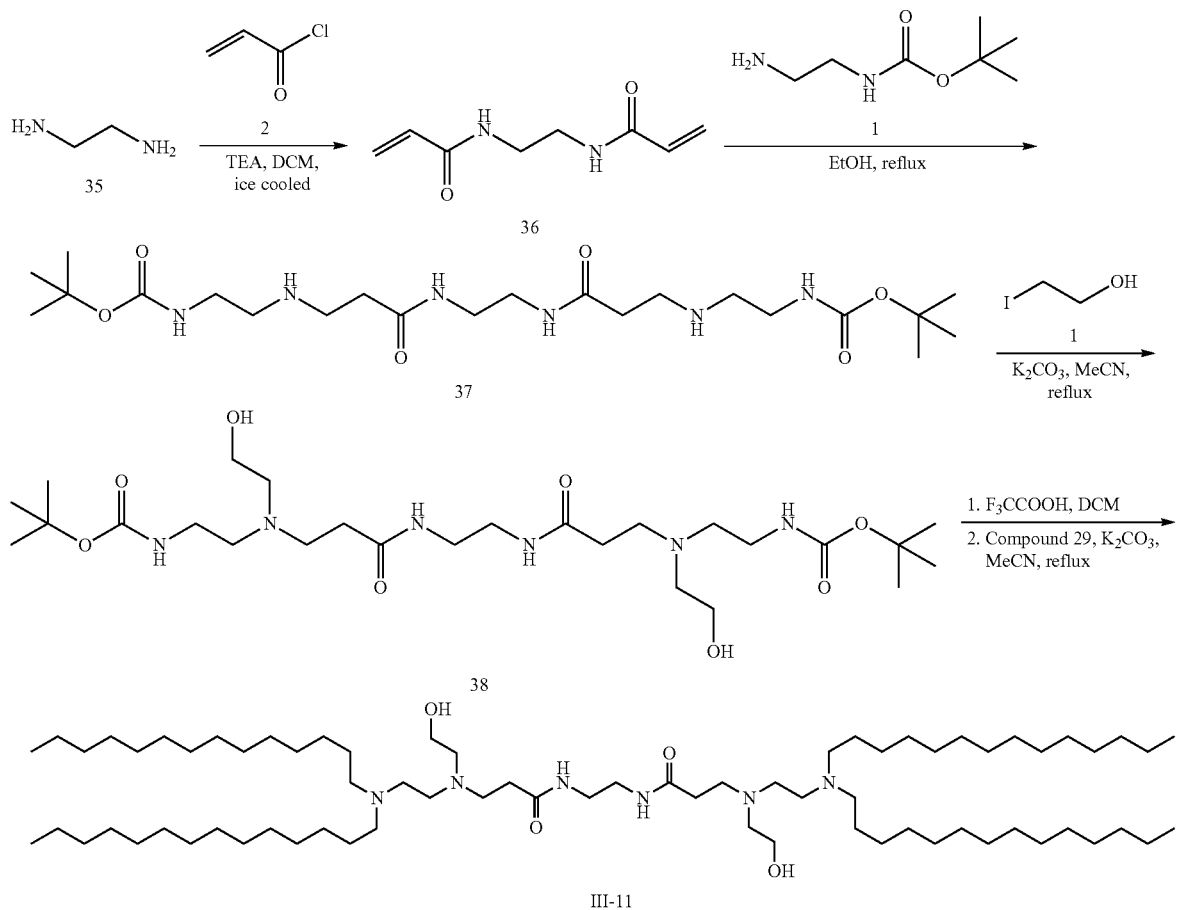

(1) Synthesis of Compound 36

Add ethylenediamine (1.0 eq) and TEA (3.0 eq) to a single-necked bottle, dissolve in an appropriate amount of anhydrous DCM, and stir evenly in an ice-water bath. Separately, acryloyl chloride (2.5eq) was dissolved in an appropriate amount of anhydrous DCM and added to a constant pressure dropping funnel, and the flow rate was controlled to make it dropwise into the above single-necked bottle, and reacted in an ice-water bath for 6 h. The reaction solvent was spin-dried, and the crude product was purified by silica gel

(3) Synthesis of Compound 38

Compound 37 (1.0eq) and iodoethanol (2.5eq) were added to a single-neck flask, dissolved in an appropriate amount of anhydrous acetonitrile, an appropriate amount of potassium carbonate was added, and the mixture was stirred at room temperature overnight. The reaction solvent was spin-dried, and the crude product was purified by silica gel column chromatography (DCM:MeOH=10:1, 1% ammonia water), concentrated and dried to obtain pale-yellow oil 38 in a yield of 65.4%.

(4) Synthesis of III-11

Compound 38 was dissolved in DCM, an appropriate amount of TFA was added under stirring, and the reaction was carried out at room temperature for 6 h. TFA/DCM was spun down to give a yellow oil. The above-mentioned oily substance is dissolved in an appropriate amount of acetonitrile, a sufficient amount of anhydrous potassium carbonate is added under stirring, and the mixture is stirred at room temperature until the reaction solvent is alkaline. Compound 29 (6.0eq) was added to the above reaction solution, a condenser was added to the single-necked flask, and the mixture was refluxed and stirred in an oil bath at 90° C. for 36 h. The reaction solvent was spin-dried, and the crude product was purified by silica gel column chromatography (DCM:MeOH=15:1, 1% ammonia water), concentrated and dried to obtain a pale-yellow oily product III-11 with a yield of 57.2%.

Example 17 Syntheses of Other Exemplified Compounds

The other exemplified compounds disclosed herein were prepared by the similar procedures described in Examples 1-16 with different starting materials.

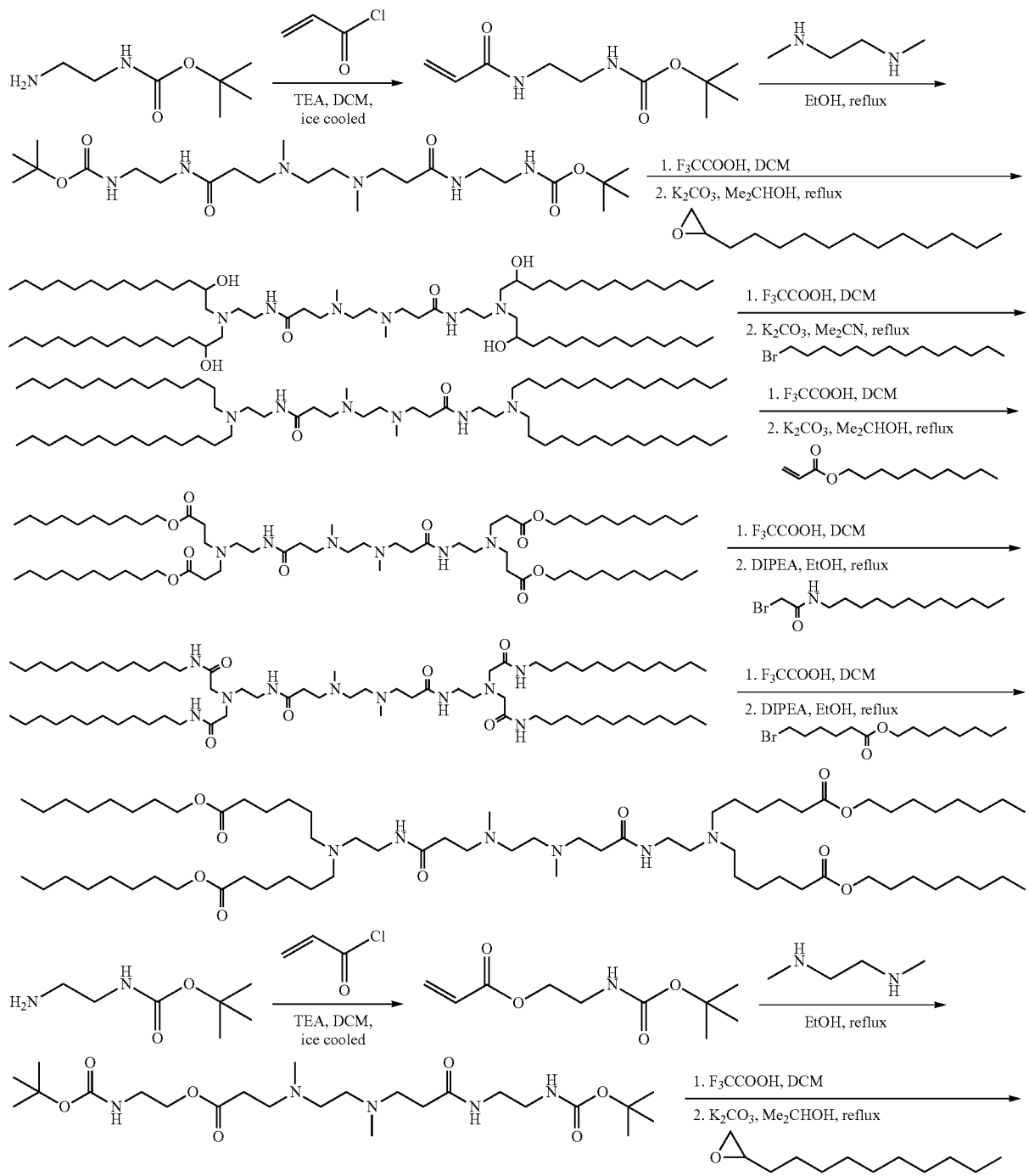

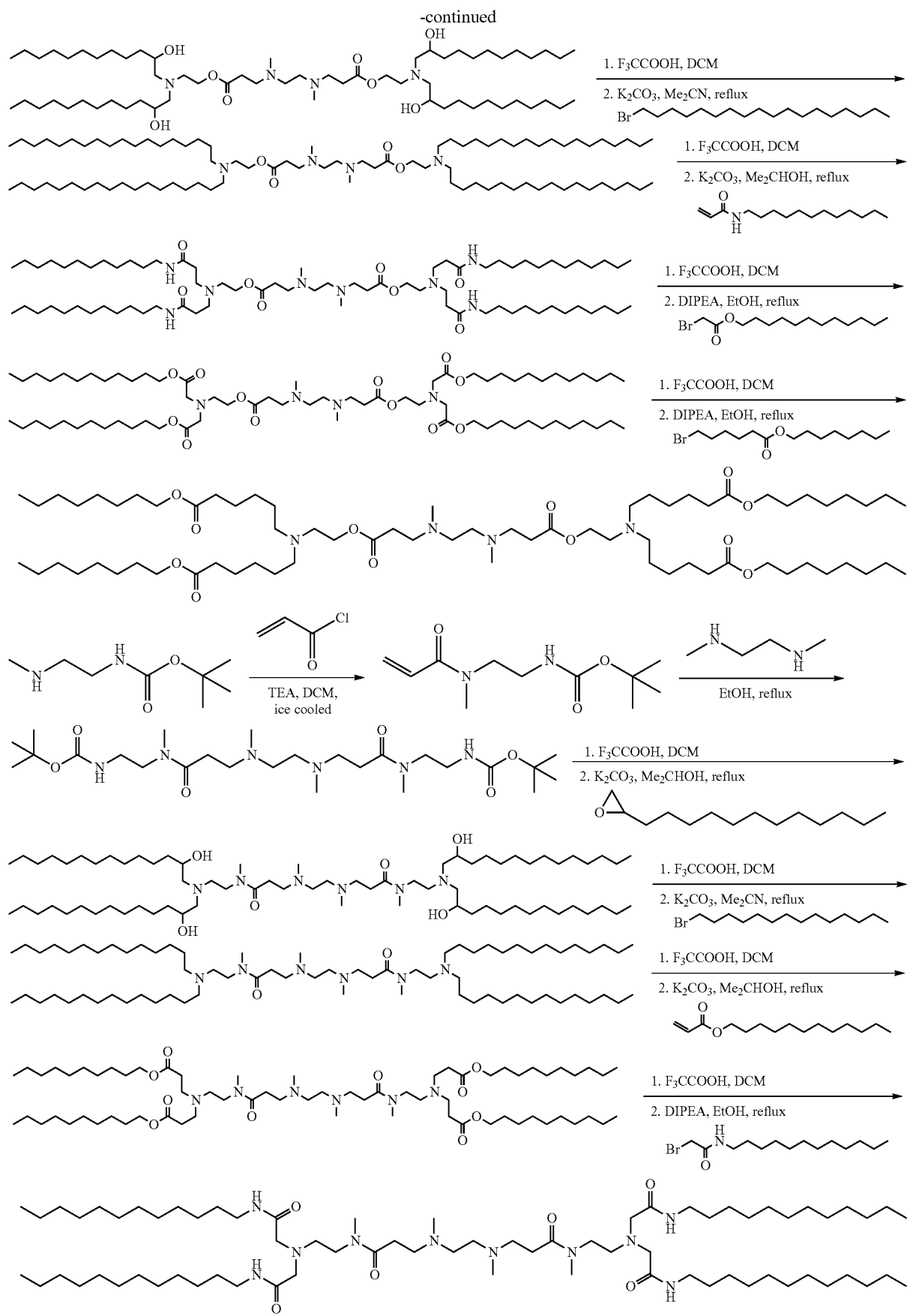

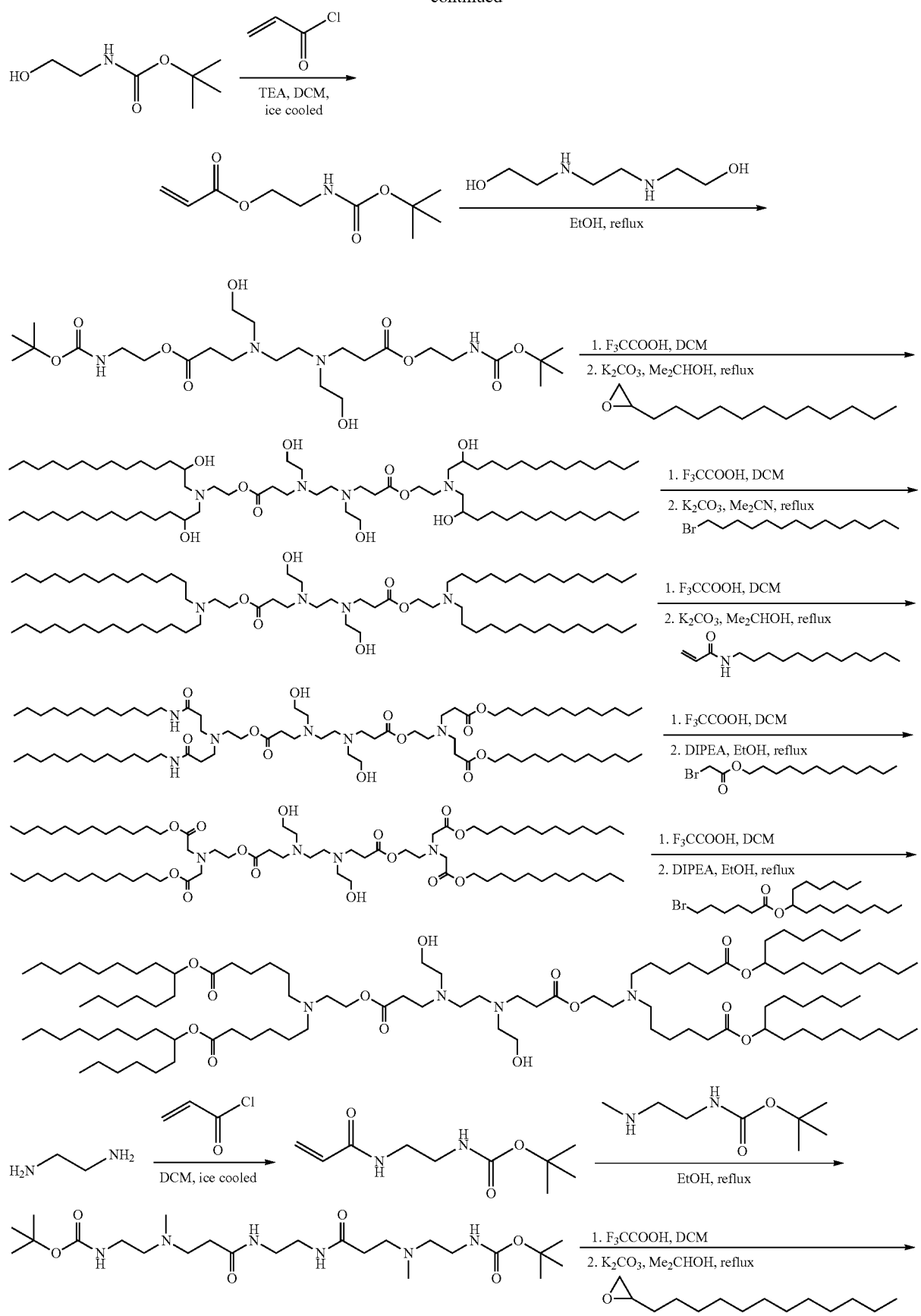

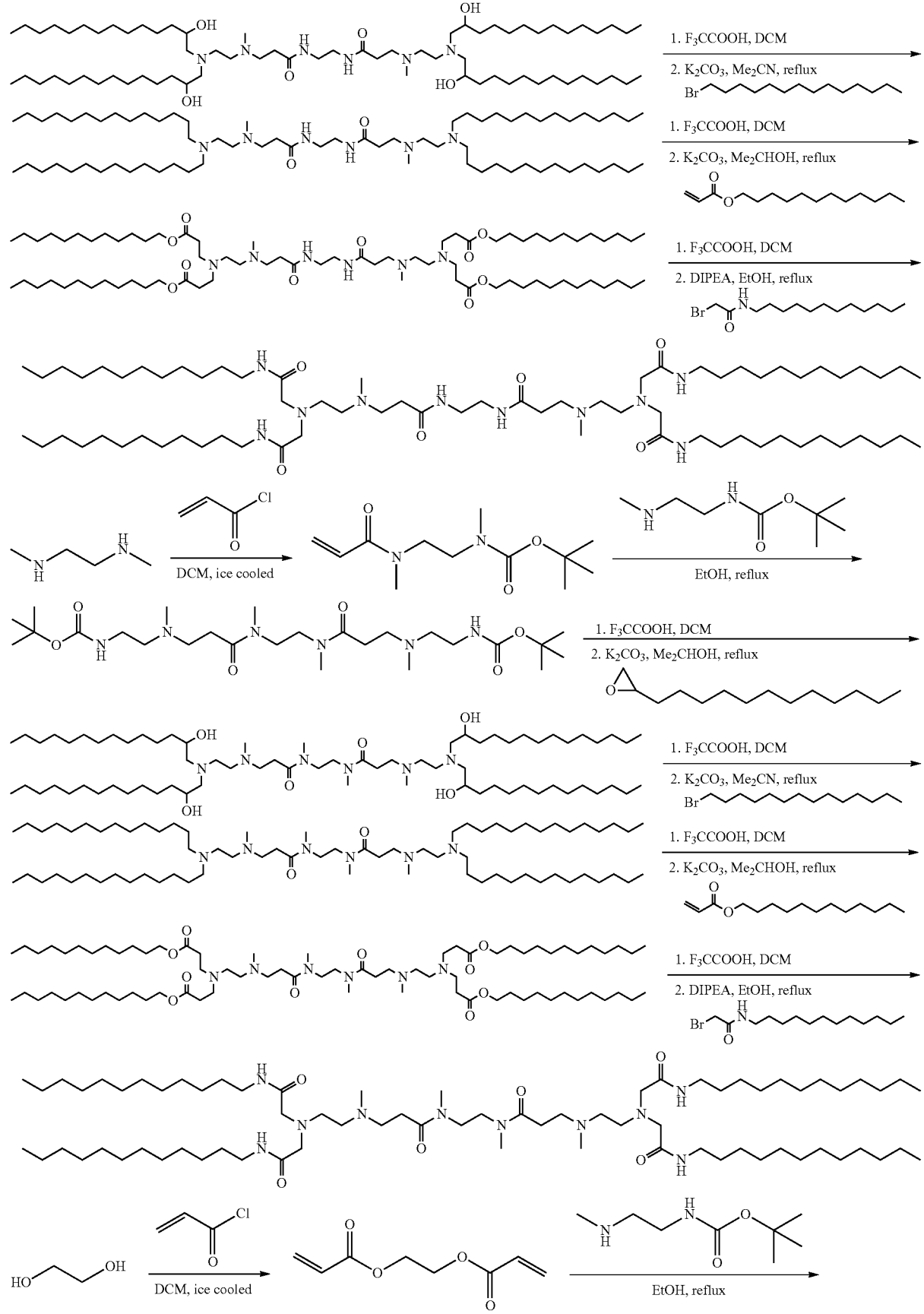

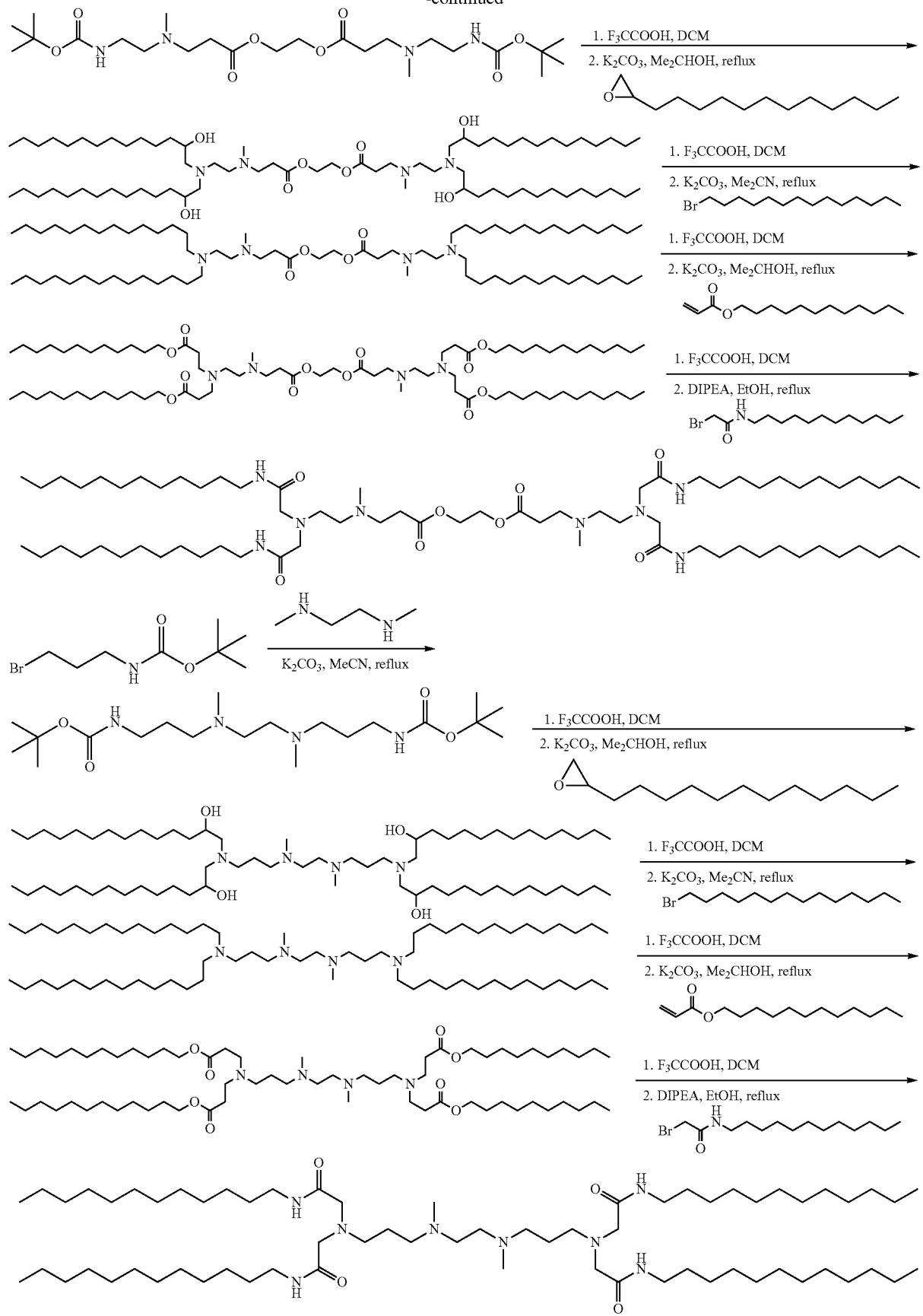

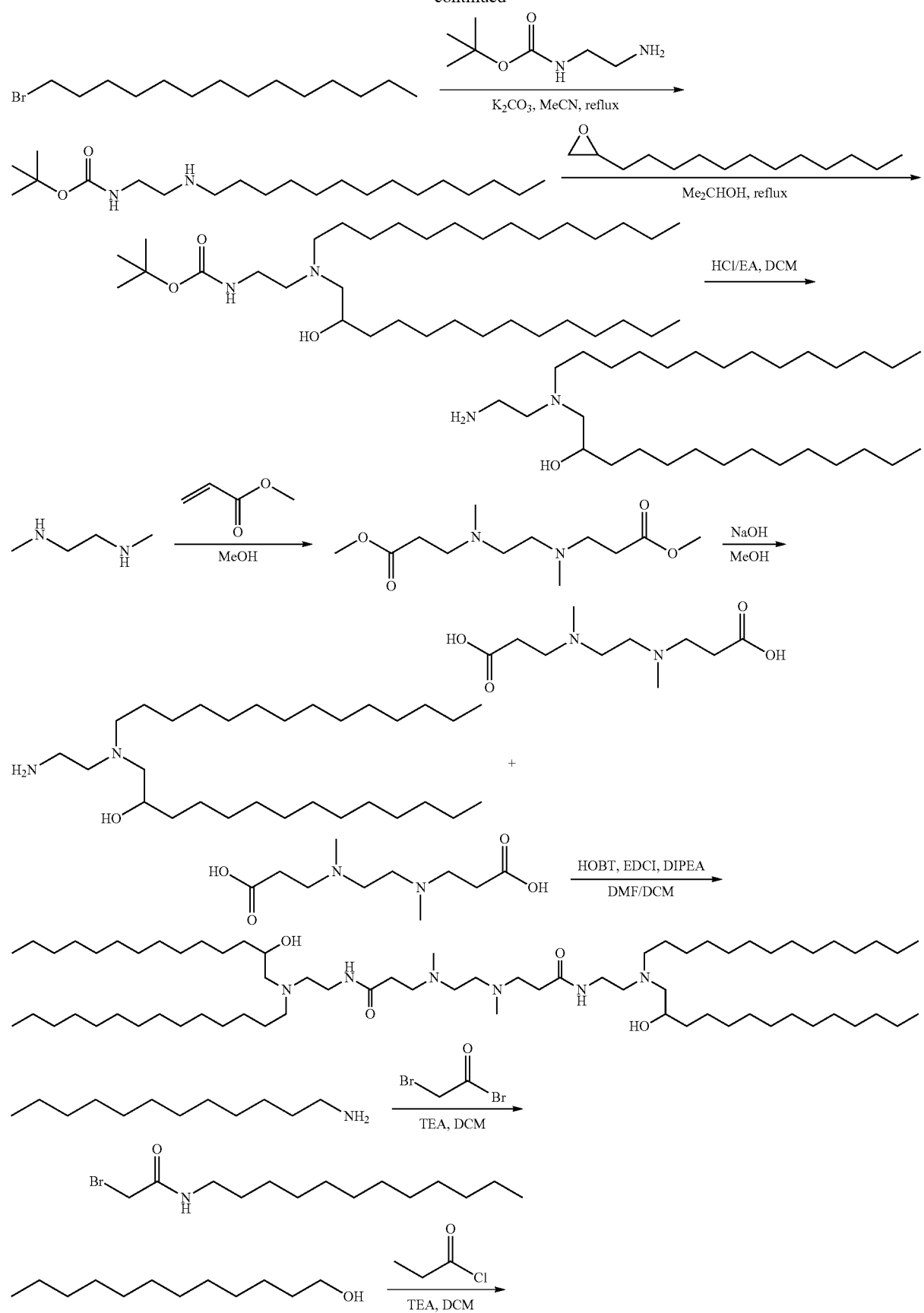

-continued
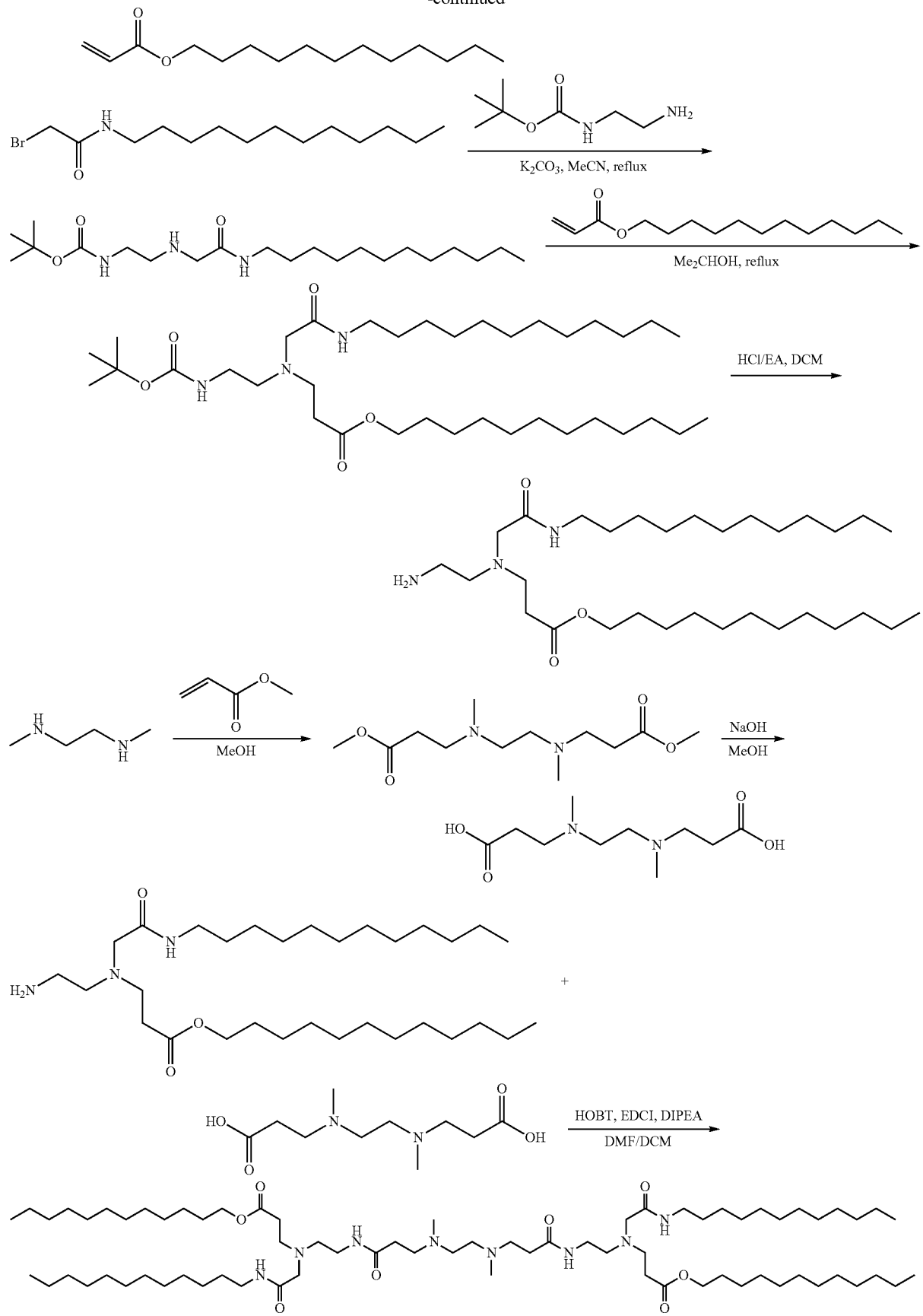

-continued
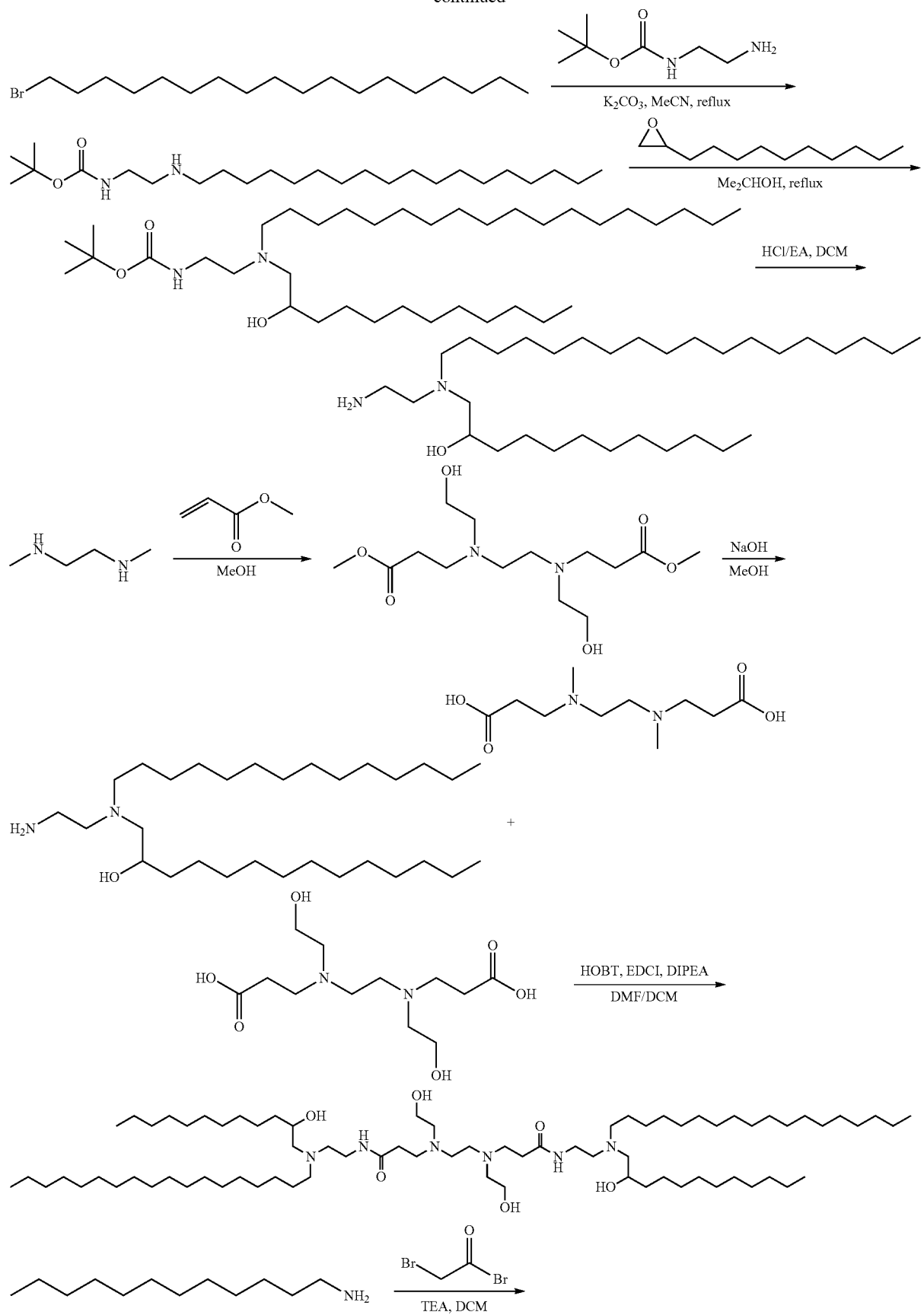

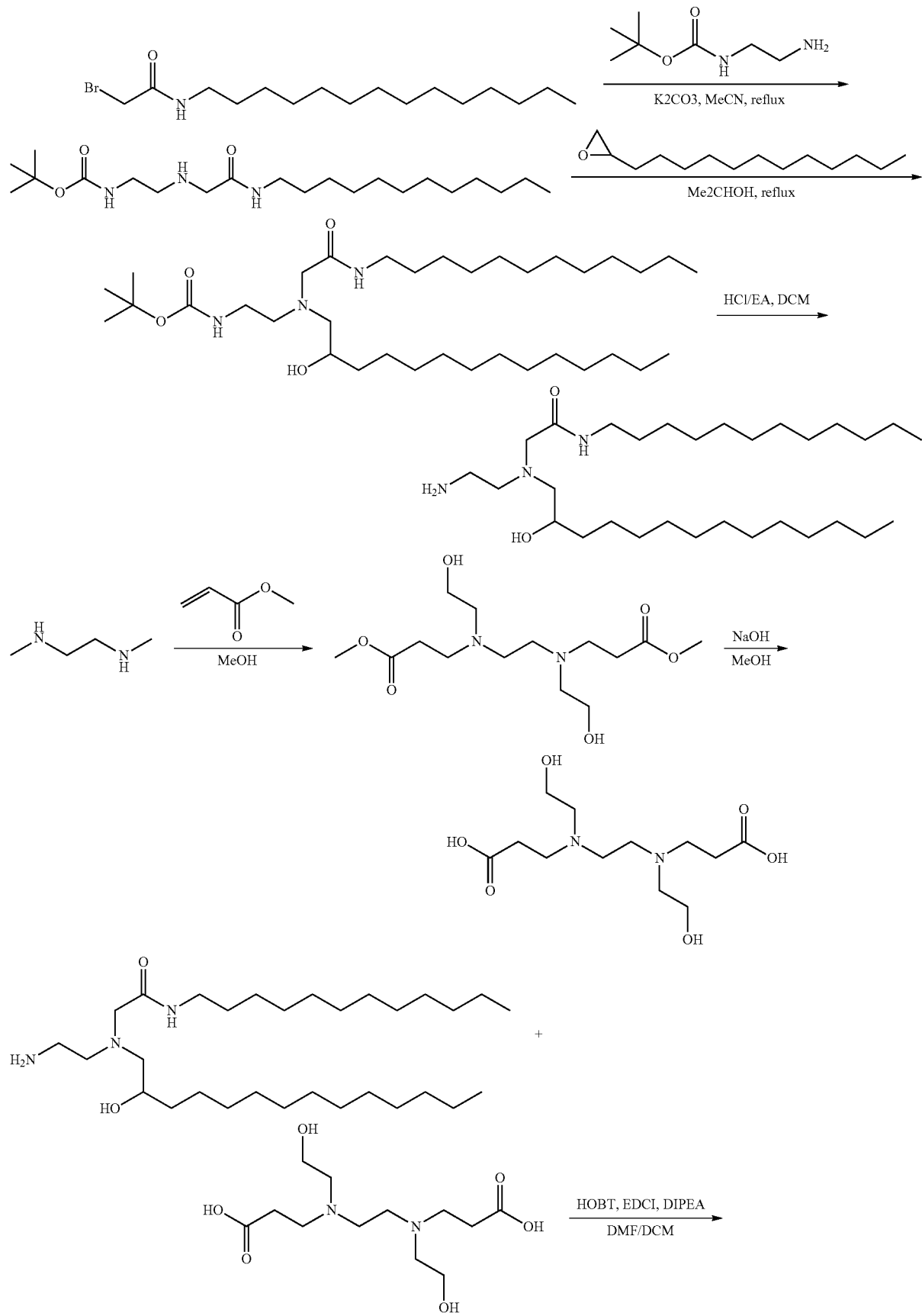
-continued

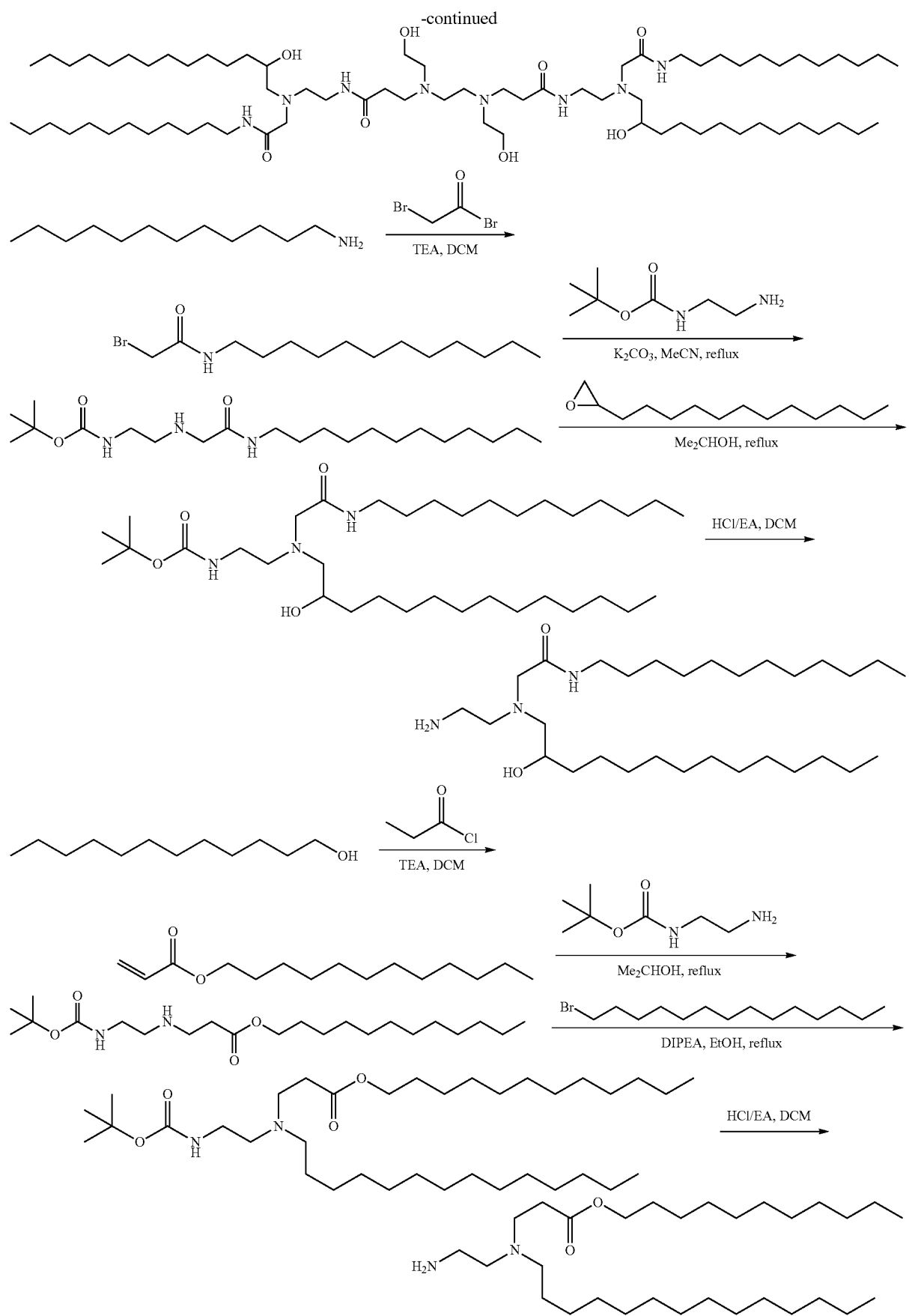

-continued

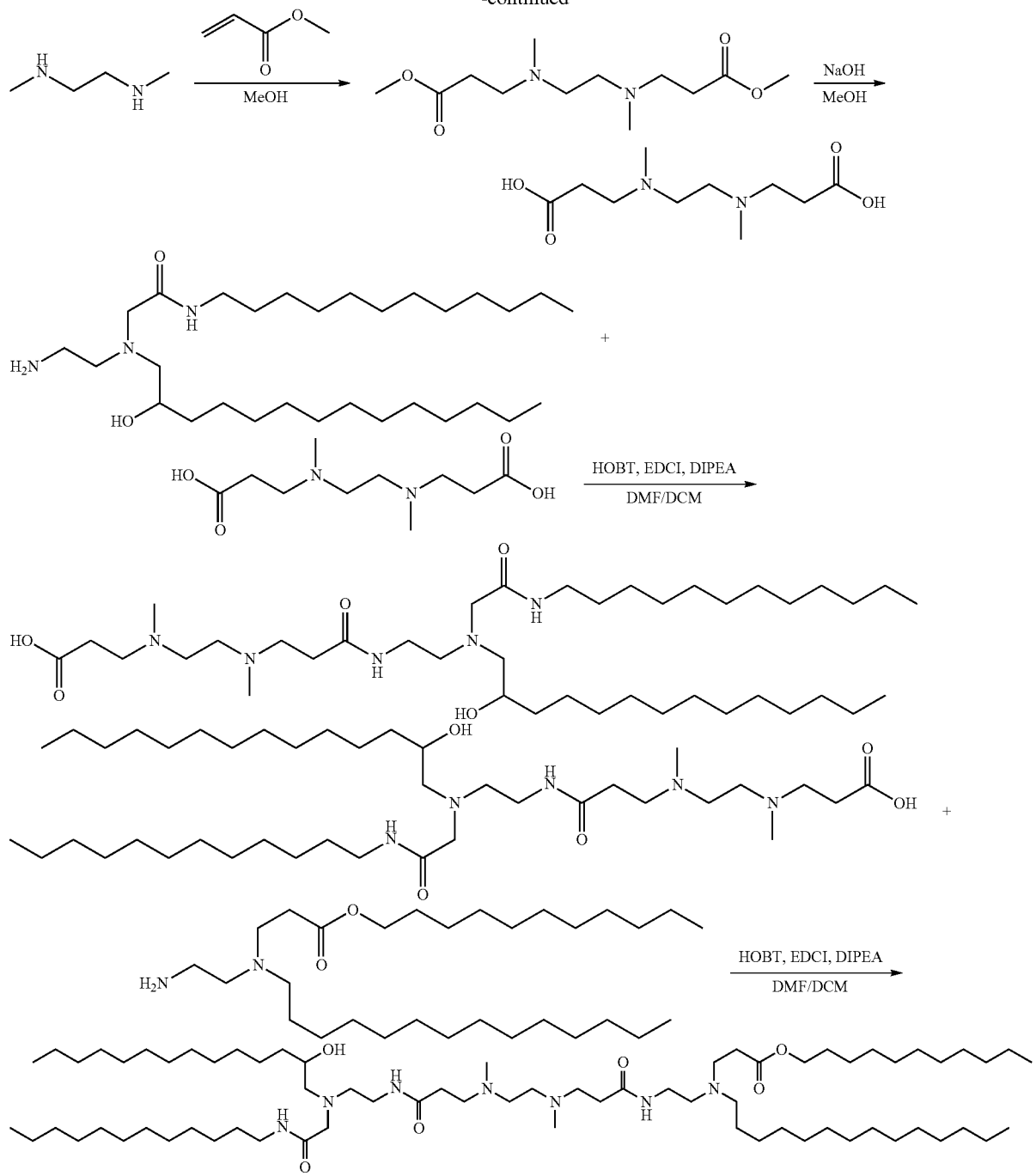

Example 18 Preparation of a Compound II-1 Lipid Nanoparticles Solution by Thin-Film Hydration Film formation: The lipid compound II-1 obtained in Example 1, DOPE, cholesterol, and DMG-PEG2000 were dissolved with absolute ethanol to form stock solutions with concentrations of 20 mg/mL, 10 mg/mL, 20 mg/mL, and 10 mg/mL, respectively. The stock solutions were refrigerated for later use. With the above-mentioned stock solutions, the four reagents were mixed to form about 3 mL of a solution by the ratio of 40:10:47.5:2.5 (mol/mol), in which the concentration of lipid compound II-1 was about 5 mg/mL. The solution was transferred into a suitable sized eggplant-shaped bottle. Finally, the solvent was removed by rotary evaporation at 37° C. on an evaporator to form a film.

Hydration: a 3 mL of 10 mM citrate buffer solution was added to the above-mentioned eggplant-shaped flask with the film formed, and the film was hydrated by rotating at 60° C. on a rotary evaporator. The above-mentioned hydration solution was transferred to a suitable container and sonicated with a probe sonicator to make it uniform. A uniform and clear lipid nanoparticle (LNP) solution was obtained, wherein the concentration of lipid compound II-1 was 3 mg/mL.

Example 19 Preparation of II-1 LNP@mRNA

The basic structural units of nucleic acid molecules such as DNA, siRNA, and mRNA are deoxynucleotides or ribonucleotides. The phosphate groups in the nucleotides dissociate into phosphate ions, which make the nucleic acid molecules negatively charged. In Example 18, in the citrate buffer system of the LNP solution, the ionizable lipid II-1 in the lipid nanoparticles was ionized into cations in an acidic environment, so that the nanoparticles were positively charged to absorb negatively charged nucleic acid drugs.

II-1 LNP and Luciferase mRNA were used as examples to prepare LNP@mRNA. The specific method is as follows: II-1 LNP obtained in Example 18 (the concentration of II-1 is 3 mg/mL) was used in an incubation method to prepare II-1 LNP@ mRNA. To prepare LNP@mRNA with a mass ratio of ionizable lipid to mRNA of 10:1, 33 μL of II-1 LNP was labelled as phase A (the mass of II-1 is 100 μg); 10 μg of Luc mRNA was added to RNase Free water and mixed well to obtain phase B (total volume is 67 μL); B was added to A, mixed by pipetting up and down with the tip of the gun, and incubated for 10 min at room temperature to obtain a LNP@mRNA solution with a mass ratio of ionizable lipid to mRNA of 10:1, in which the concentration of mRNA is 0.1 mg/mL. Similarly, to prepare II-1 LNP@mRNA with a mass ratio of 15:1, the volume of phase A was 50 μL (the mass of II-1 was 100 μg), and the volume of phase B was 50 μL. The same method was used for other LNP@mRNAs with different mass ratios.

The above experimental method can be scaled up in the same proportion to prepare a larger volume of LNP@mRNA solution.

Example 20 Investigation II-1 LNP Nucleic Acid Loading Capacity

In Example 19, II-1 LNP@mRNA was prepared. Further, it was necessary to investigate the loading capacity of different ionizable lipid nanoparticles disclosed herein for nucleic acid molecules, to investigate the ratio of ionizable lipids to nucleic acid molecules. II-1 LNP and mRNA were used as examples, the loading capacity of ionizable lipid nanoparticles for nucleic acid molecules was investigated.

(1) Preparation of Denaturing Agarose Gel 36 mL of RNase-free water and 0.4 g of agarose were placed in a conical flask, heated in a microwave oven for 2 min, cooled to about 60° C., added with 4 mL of 10× MOPS (4-morpholinepropanesulfonic acid) and mixed, and then added with 7.5 mL of 37% formaldehyde and mixed evenly. The mixture was poured into a gel tank, the thickness of the gel was controlled to be about 0.5 cm. A comb was inserted into the gel tank and was taken out after solidification. The gel was placed into an electrophoresis tank, and the newly prepared 1×MOPS electrophoresis buffer was added to the electrophoresis tank to cover the gel.

(2) Preparation of Electrophoresis Sample

To 0.5 μL mRNA (0.5 μg) mixed with 4.5 μL RNase-free water, or 5.0 μL (0.5 μg mRNA) of II-1 LNP@mRNA prepared in Example 19 with different mass ratios, was added 5 μL of formaldehyde loading buffer with ethidium bromide, heated at 70° C. for 5 min, and then centrifuged at 4° C. for a short period of time.

(3) Gel Electrophoresis

The samples were added to the gel wells with a loading volume of 10 μL and the electrophoresis conditions were set to 200 V (current at 300 mA, power at 60 W). When the indicator front reached ⅔ of the gel (about 25 minutes), electrophoresis was stopped, the gel was taken out, and placed in a gel imager for observation. The results are shown in FIG. 1.

As shown in FIG. 1, in the II-1 LNP@mRNA solution, with a mass ratio of ionizable lipid II-1 to Luc mRNA being 10:1, the complete encapsulation of mRNA was achieved.

Example 21 Formulation Characterization of II-1 LNP@mRNA

An appropriate amount of the LNP solution prepared in Example 19 was diluted 100 times with purified water, and the particle size (Size), particle size distribution (PDI) and point (Zeta potential) of the LNP solution were measured in a laser particle size analyzer. The results showed that the particle size of II-1 LNP@mRNA was 102.3 nm, the PDI was 0.195, the potential was 31.2 mV, and the preparation properties were stable.

Figure 2:
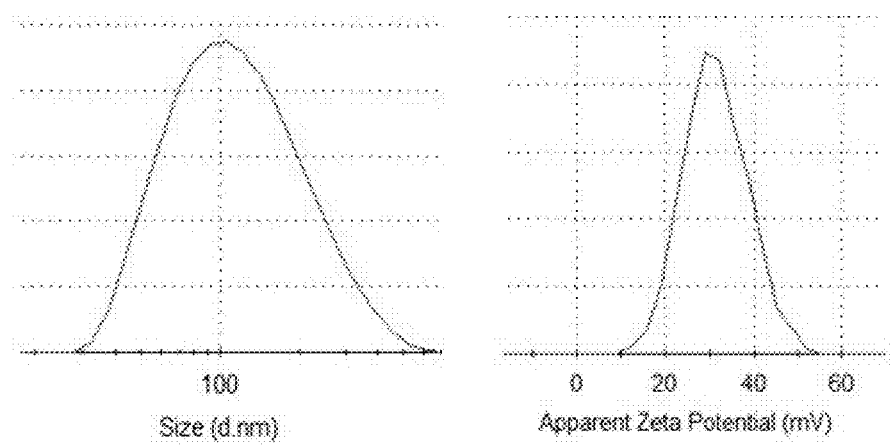
FIG. 2 shows Particle size, PDI and potential of II-1 LNP@mRNA.

The particle size and point (Zeta potential) test results are shown in FIG. 2.

Example 22 Morphological Characterization of II-1 LNP@mRNA

Sample preparation: the LNP solution prepared in Example 19 was diluted with purified water to a total lipid material concentration of about 1 mg/mL. The diluted LNP solution was dropped onto a special copper mesh, let it stand for 3 minutes, and the excess LNP solution was removed with filter paper. The diluted LNP solution was negatively stained by adding a 2% phosphotungstic acid dye solution dropwise for 5 min, and then the excess dye solution was removed with filter paper and left to dry.

Photograph: After air-drying, the morphology of II-1 LNPs was observed under a transmission electron microscope and photographed.

Figure 3:
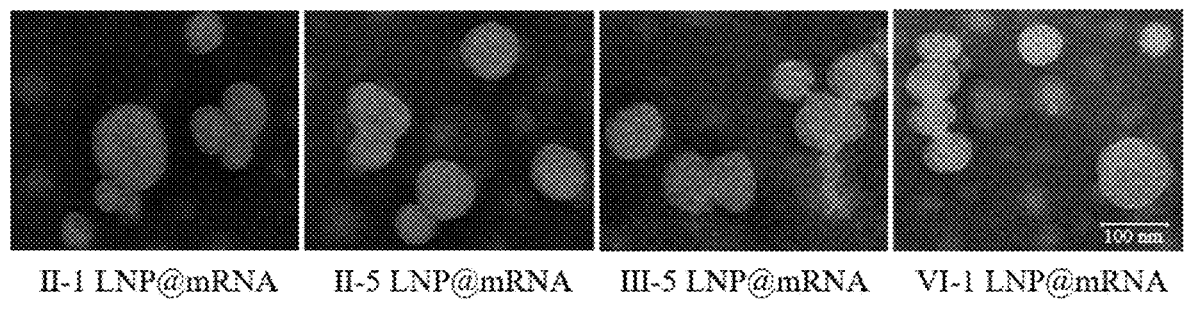
FIG. 3 shows photographs of microstructures of II-1, II-5, II-5, VI-1 LNP@Luc mRNA.

II-5 LNP@mRNA, III-5 LNP@mRNA, VI-1 LNP@mRNA were prepared according to the methods described in Examples 18 and 19, and the mass ratios of ionizable lipid to mRNA were all 10:1. The samples were prepared and photographed according to the above method. The microscopic morphology of II-1 LNP@mRNA, II-5 LNP@mRNA, III-5 LNP@mRNA and VI-1 LNP@mRNA is shown in FIG. 3.

Example 23 One-Step Microfluidic Preparation of mRNA-Loaded Ionizable Lipid Nanoparticles Solution II-7 LNP@mRNA was used as an example. It was prepared by microfluidic technology. The formulation was composed of II-7, DOPE, cholesterol, DMG-PEG2000 and mRNA, and the mass ratio of II-7 and mRNA was set to 10:1 to prepare an organic phase and an aqueous phase. II-7, DOPE, cholesterol and DMG-PEG2000 were dissolved in absolute ethanol to prepare a certain volume of an organic phase with a molar ratio of 40:10:47.5:2.5. In the meantime, Luc mRNA was diluted with RNase-Free water to obtain a certain volume of an aqueous phase. The volume ratio of the aqueous phase to the organic phase was 3:1. II-7 LNP loaded with mRNA was prepared by an one-step microfluidic devices. The instrument parameters were set as follows: ratio of aqueous phase to organic phase was fixed at 3:1 and the flow rate was fixed at 9 mL/min. The initial microfluidic preparation was ultrafiltered with phosphate buffered saline (PBS) to remove ethanol, and the mRNA concentration of the final preparation was controlled to be 0.1 mg/mL, to obtain II-7 LNP@mRNA.

Example 24 Quant-iT™ RiboGreen™ Kit for Detection of Encapsulation Efficiency The encapsulation of mRNA by the LNP preparations obtained in Examples 22 and 23 was measured by a Quant-iT™ RiboGreen™ RNA detection kit using a method described in Heyes et al., Journal of Controlled Release, 107:276-287 (2005). It was found that encapsulation rates of mRNA in II-1 LNP@mRNA, II-5 LNP@mRNA, III-5 LNP@mRNA, VI-1 LNP@mRNA and II-7 LNP@mRNA preparations were 86.1%, 82.8%, 85.0%, 78.6% and 90.5%, respectively. These results demonstrate that the ionizable lipids disclosed herein, which were obtained by various preparation methods, have good encapsulation efficiency for mRNA.

Example 25 Preparation of MC3 LNP@mRNA

DLin-MC3-DMA (MC3) is a cationic lipid used in the marketed siRNA drug Patisiran (Onpattro) and is often used as a positive control for nucleic acid loading materials. According to the method of example 23, MC3 LNP@mRNA was prepared with MC3 as the load material of nucleic acid, wherein includes: MC3: DSPC: Cholesterol: DMG-PEG2000=50: 10: 37.5: 2.5; the mass ratio of MC3 to mRNA was 10:1, and the concentration of preparation mRNA was 0.1 mg/mL. MC3 LNP@mRNA was used as a positive control for ionizable lipid nanoparticles loaded with nucleic acids of the present disclosure.

Example 26 LNP@GFP mRNA Transfect into DC2.4 Cells

Figure 4:
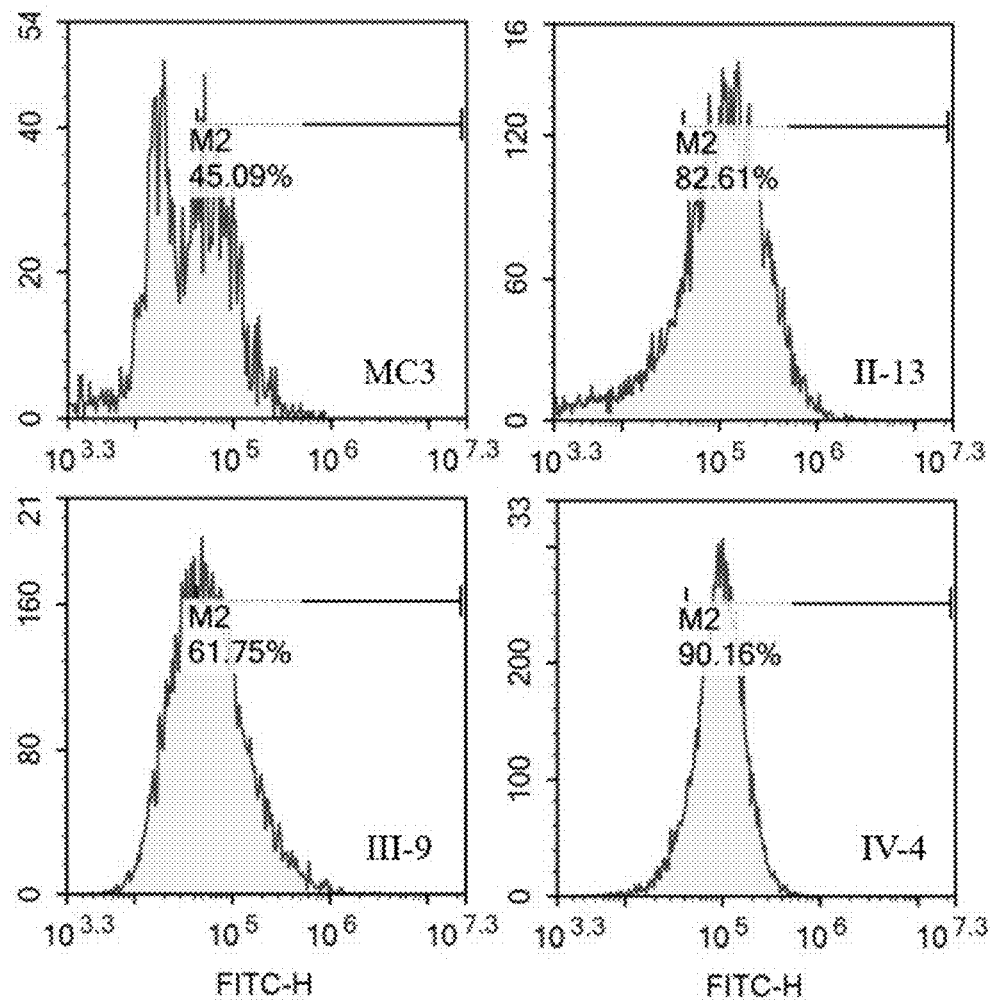
FIG. 4 illustrates transfection rate of MC3, II-13, III-9, IV-4 LNP@GFP mRNA on DC2.4 cells.

The foregoing examples demonstrate the pharmaceutical properties of ionizable lipid nanoparticles of the present disclosure. The in vitro effects of LNP@ mRNA of the present disclosure was demonstrated as follows.
II-13 LNP@GFP mRNA, III-9 LNP@GFP mRNA and IV-4 LNP@GFP mRNA were prepared according to the method described in Example 23, in which the mass ratios of ionizable lipids to GFP mRNA were all 10:1, and the mRNA concentrations in the preparation were all 0.1 mg/mL. MC3 LNP@GFP mRNA was prepared according to Example 25. DC2.4 cells were collected in logarithmic growth phase, and following medium suspending, the cell density was adjusted to $20 \times 10^4$ cells/mL. 0.5 mL complete culture medium and 0.5 mL cell suspensions were added to each well and were mixed in the 6-well plate to make the cell density $10 \times 10^4$/mL/well.
After 18-24 h incubation, the medium in the 6-well plate was changed with 1 mL liquid complete culture medium. MC3 LNP-GFP mRNA, II-13 LNP@GFP mRNA, III-9 LNP@GFP mRNA and IV-4 LNP@GFP mRNA, which loaded 1 μg GFP mRNA, were added into each well of the six-well plate with 3 wells repetitions.
The transfection effects of different preparations were observed and detected by inverted fluorescence microscope and flow cytometry after 24 h of administration. The results were shown in FIG. 4.

The average GFP positive rate of DC2.4 cells transfected by MC3 LNP@GFP mRNA, II-13 LNP@GFP mRNA, III-9 LNP@GFP mRNA, IV-4 LNP@GFP mRNA, were 45.09%, 82.61%, 61.75% and 90.16%, respectively.
The results showed that the ionizable lipids and nanoparticles of the present disclosure have stronger transfection ability in vitro than MC3.

Example 27 the Expression and Distribution of LNP@Luc mRNA In Vivo

Figure 5:
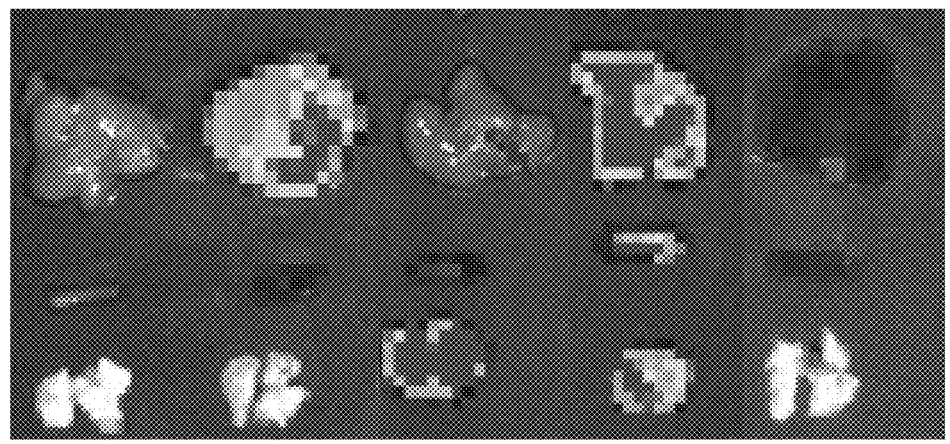
FIG. 5 shows expression and distribution of II-11, III-6, V-2 and MC3 LNP@Luc mRNA in vivo.

The effects of ionizable lipid compounds of the present disclosure and the corresponding nanoparticles to deliver mRNA were further verified in vivo.
II-11 LNP@Luc mRNA, III-6 LNP@Luc mRNA and V-2 LNP@Luc mRNA were prepared according to the method described in Example 23, in which the mass ratio of ionizable lipids to Luc mRNA was 10:1, and the mRNA concentration in the preparation was 0.1 mg/mL. MC3 LNP@Luc mRNA was prepared according to Example 25.
The mRNA expression and distribution were studied in Balb/C male mice.
The above-mentioned four preparations were injected intravenously through the mouse tail vein with a dose of 10 μg/100 μL/mouse (normal saline group was injected with 100 μL normal saline), 3 mice/group. After the injection, the mice were free to eat and drink. After 6 hours of administration, 200 μL luciferin substrate was injected to mice intraperitoneally. The mice were euthanized after 15 min of luciferin substrate injection, the liver, the spleen and the lung were separated, and the expression and in vivo distribution of Luc mRNA were observed using a small animal imaging system, as shown in FIG. 5. The results show that the ionizable lipid nanoparticles of the present disclosure have stronger total fluorescence, i.e., stronger effects of in vivo mRNA expression than MC3.

Example 28 Immune Antitumor Effect of LNP@OVA mRNA Vaccine

Based on the applications of Examples 26 and 27, the ionizable lipid compounds and their nanoparticles of the present disclosure can be used as mRNA vaccine delivery systems. Further, the ionizable lipid nanoparticle loaded OVA mRNA of the present disclosure was tested in an immune anti-tumor therapy with E.G7 model mice.
II-9 LNP@OVA mRNA, III-8 LNP@OVA mRNA, II-22 LNP@OVA mRNA and VI-4 LNP@OVA mRNA were prepared according to the method described in Example 23, in which the mass ratio of ionizable lipids to OVA mRNA was 10:1. The mRNA concentration in the preparation was 0.1 mg/mL. MC3 LNP@OVA mRNA was prepared according to Example 25.
Newly purchased female C57BL/6 mice were labeled and randomly assigned. Each group had 10 mice, and groups including normal saline group, MC3 LNP@OVA mRNA group, II-9 LNP@OVA mRNA group, III-8 LNP@OVA mRNA group, II-22 LNP@OVA mRNA group, VI-4 LNP@OVA mRNA group. The mice were injected with tumors after one week of adaptation. The induction process was as following description: the cells were collected at the logarithmic growth stage and were washed with sterile PBS. The supernatant was discarded after centrifugation, and the cell density was adjusted to $10 \times 10^6$/mL by adding sterile PBS. Each 6-week-old female C57BL/6 mouse was subcutaneously injected with 100 μL E.G7 cells at the right rib. The growth status and size of subcutaneous tumors were observed. Compared with normal mice, there were no significant differences of spirit, activity, appetite, urine or feces reaction in tumor-bearing mice.

Figure 6:
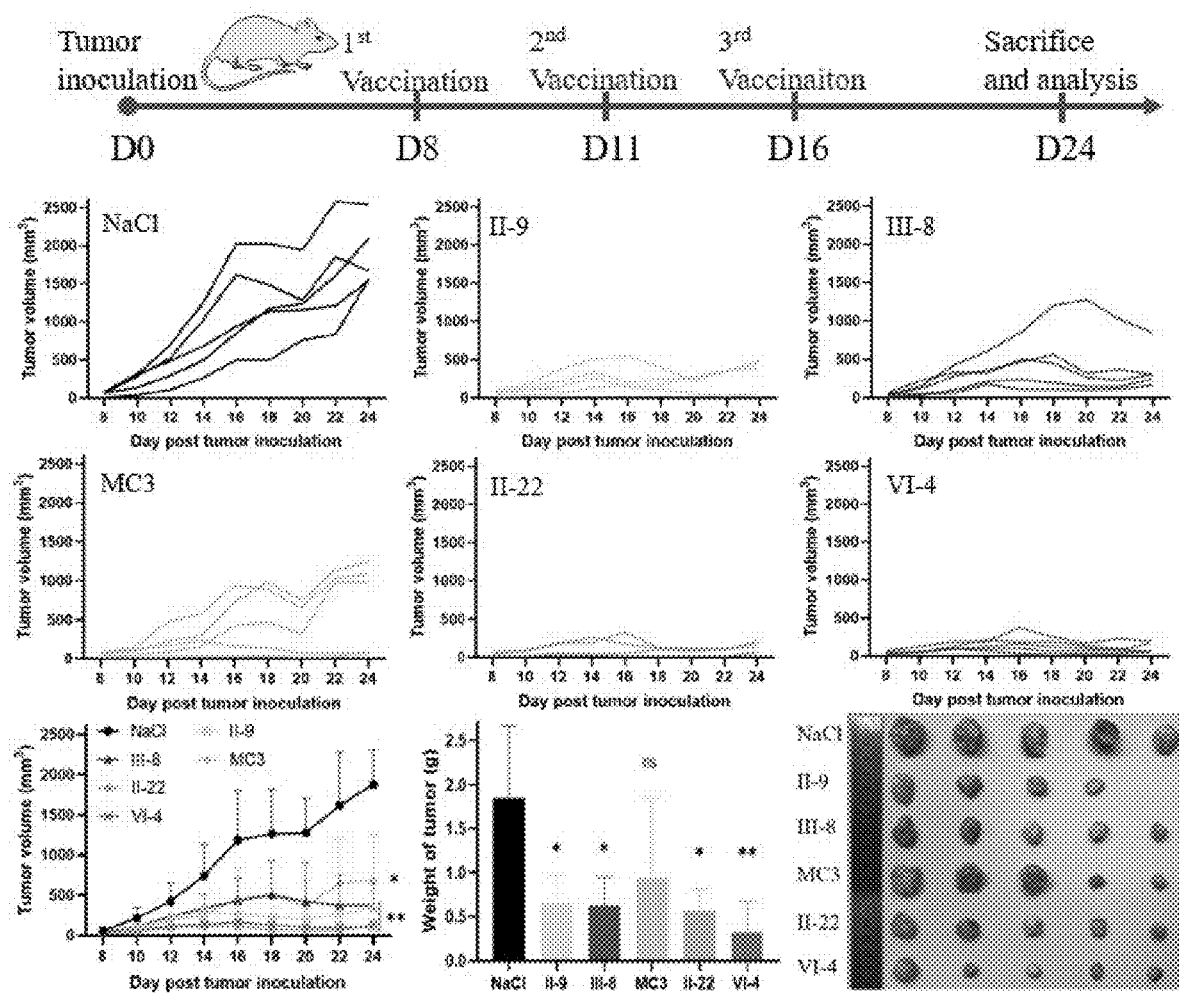
FIG. 6 shows immunological anti-tumor effects of II-9, III-8, II-22, VI-4 LNP@OVA mRNA.

The Day of tumor grafting was marked as Day 0, and the appearance of tumor mass indicates successful modeling. At Day 8, mRNA vaccine was injected into caudal vein (10 μg/100 μL/time/mouse, normal saline group was injected with 100 μL normal saline), and mice were vaccinated every week for 3 times. From Day 8, tumor volume was measured every 2 days. The maximum diameter (a) of the tumor was firstly measured, and then the longest diameter perpendicular to the maximum diameter line (b) was measured, in mm. Tumor volume was calculated according to the following formula $V(mm^3)=ab^2/2$ and tumor volume growth curve of each mouse and average tumor volume growth curve of each group were recorded. On Day 24, the mice were euthanized, the tumor and organs were weighed after separation and were recorded. The result was shown in FIG. 6.
The results show that the ionizable lipids and nanoparticles of the present disclosure have stronger immune anti-tumor effects than MC3, and are promising in the field of mRNA vaccine delivery.

Example 29 Safety Evaluation of Intramuscularly Injected LNP@OVA mRNA Vaccines Furthermore, the injection site reaction of ionizable lipids and their nanoparticles in intramuscular administration was investigated.
III-3 LNP@OVA mRNA and VI-2 LNP@OVA mRNA were prepared according to the method described in Example 23, in which the mass ratio of ionizable lipids to OVA mRNA was 10:1, and the mRNA concentration in the preparation was 0.5 mg/mL. MC3 LNP@OVA mRNA was prepared, according to Example 25.

Figure 7:
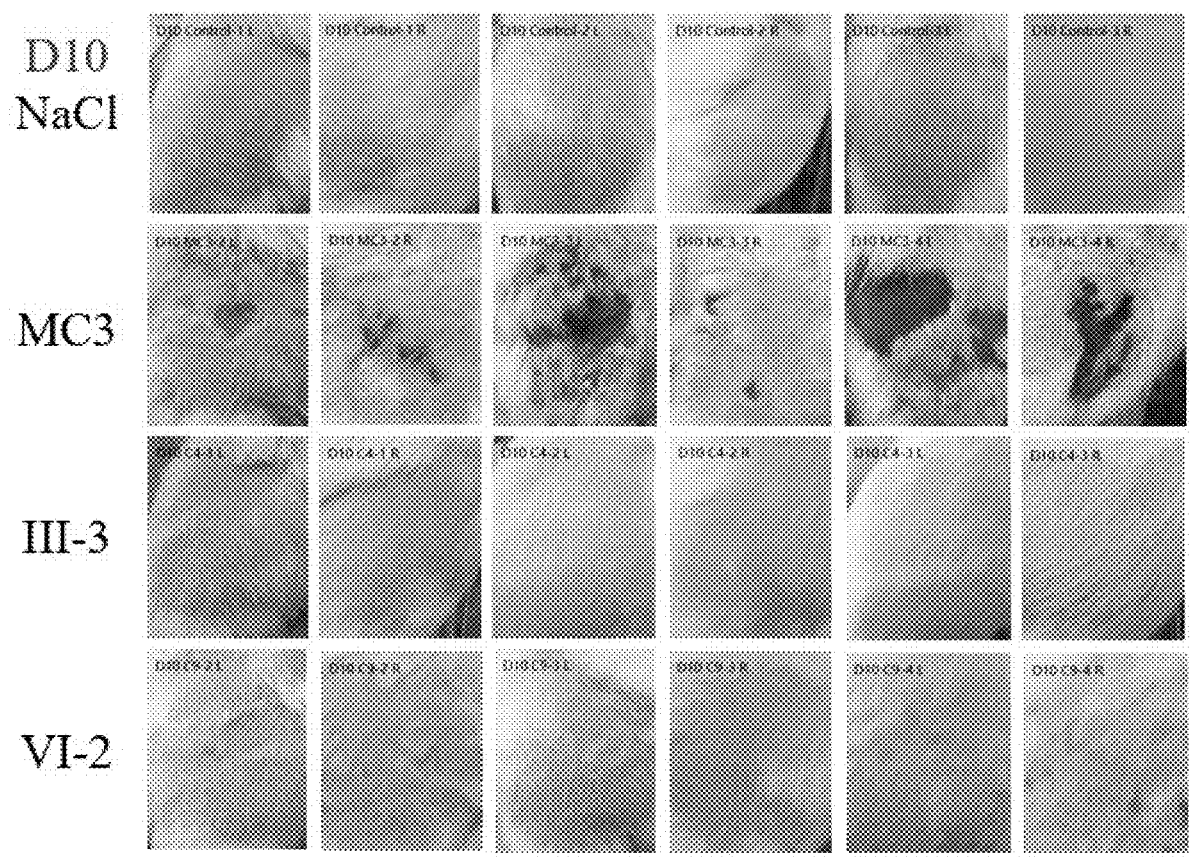
FIG. 7 shows intramuscular injection safety effects of MC3, III-3, and VI-2 LNP@OVA mRNA.

Newly purchased SD rats were randomly divided to 4 groups with 3 rats in each group, including normal saline group, III-3 LNP@OVA mRNA group, VI-2 LNP@OVA mRNA group and MC3 LNP@OVA mRNA group, respectively. After one week of adaptive culture, the lateral hairs of the hind legs of the rats were removed, and 500 μL mRNA preparation (0.5 mg/mL) was intramuscular injected into each side of the rats, i.e., the dose was 0.5 mg/mouse. In the saline group, 500 μL normal saline was intramuscular injected into both sides, which was recorded as D0 on the day of administration. Mice were secondly injected in D8 with the same dose as D0. The changes of injection site were observed and recorded every other day after the first injection. The result is shown in FIG. 7.

The results showed that the injection site inflammation of MC3 group was severe, and III-3 and VI-2 groups had similar results with the normal saline group with basically no inflammation. The safety of ionizable lipids and nanoparticles of the present disclosure is higher than MC3 and has good clinical transformation prospect.

Example 30 Preparation of LNP Loaded with Luc mRNA by Microfluidics

II-5 LNP@Luc mRNA was used as an example. LNP@mRNA was prepared by microfluidic technology. The formulation was composed of II-5, DSPC, Cholesterol, DMG-PEG2000 and mRNA, and the mass ratio of II-5 and mRNA was set to 10:1 to prepare the organic phase and the aqueous phase. Dissolve II-5, DSPC, Cholesterol and DMG-PEG2000 in absolute ethanol and prepare a certain volume of organic phase in a molar ratio of 50:10:38.5:1.5, and simultaneously prepare Luc mRNA with RNase-Free water. A certain volume of aqueous phase, in which the volume ratio of aqueous phase to organic phase is 3:1, was used to prepare II-5 LNP preparation loaded with mRNA in one step by a microfluidic nano-preparation apparatus. The instrument parameters are set as follows: volume ratio of aqueous phase to organic phase was fixed at 3:1 and the flow rate was fixed at 9 mL/min. The initial microfluidic preparation was ultrafiltered with phosphate buffered saline (PBS) to remove ethanol, and the mRNA concentration of the final preparation was controlled to be 0.1 mg/mL to obtain II-5 LNP@mRNA.

Figure 8:
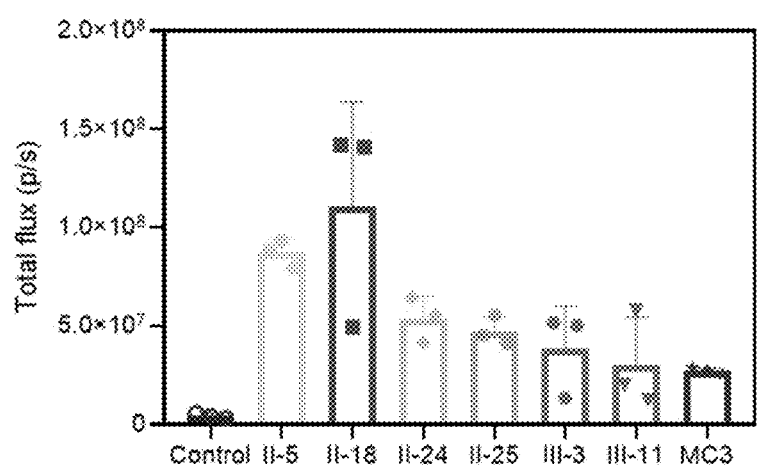
FIG. 8 shows in vivo expression of representative LNP@Luc mRNA via intramuscular injection.

Example 31 Luciferase Expression of LNP@Luc mRNA Via Intramuscular Injection Further, the ability of the ionizable lipid compounds and nanoparticles of the present disclosure to deliver mRNA was verified in vivo.
II-5 LNP@Luc mRNA, II-18 LNP@Luc mRNA, II-24 LNP@Luc mRNA, II-25 LNP@Luc mRNA, III-3 LNP@Luc mRNA, III-11 LNP@Luc mRNA were prepared according to the method described in Example 30, wherein the mass ratio of ionizable lipid to Luc mRNA was 15:1, and the concentration of mRNA in the preparation was 0.1 mg/mL. According to Example 25, MC3 LNP@Luc mRNA was prepared. BALB/C male mice were used to conduct mRNA expression and distribution experiments. The above four preparations were intramuscularly injected, 20 μg/100 μL/mice (100 μL normal saline was injected in the normal saline group), 3 rats/group, and the mice were free to eat and drink after injection. 8 h after administration, intraperitoneal injection of luciferin substrate 3 mg. After 15 min of Luciferin substrate injection, the in vivo expression of Luc mRNA was observed using a small animal in vivo imaging system, as shown in FIG. 8. The results show that the ionizable lipid nanoparticles of the present disclosure have stronger total fluorescence than MC3, that is, the ability to express mRNA in vivo is stronger than that of MC3.

Example 32 Encapsulation Efficiency Detected by Quant-iT™ RiboGreen™ Kit

Quant-iT™ RiboGreen™ RNA detection kit was used to determine the encapsulation efficiency of mRNA by LNP preparations in Example 31. The results showed that II-5 LNP@Luc mRNA, II-18 LNP@Luc mRNA, II-24 LNP@Luc mRNA, II-25 LNP@Luc mRNA, III-3 LNP@Luc mRNA, III-11 LNP@Luc mRNA The encapsulation rates of mRNA in the preparations were 88.5%, 89.4%, 85.7%, 90.5%, 88.0% and 87.9%, respectively. It shows that the LNP prepared by the ionizable lipid provided in the present disclosure has a good encapsulation efficiency for mRNA.

Example 33 Preparation of LNP@S mRNA by Microfluidic Method

Further, the ionizable lipid of the present disclosure is applied to the novel coronavirus mRNA vaccine, and the mRNA encoding the S protein is designed for SARS-CoV-2. II-5 LNP@S mRNA, II-18 LNP@S mRNA, II-24 LNP@S mRNA, II-25 LNP@S mRNA, III-3 LNP@S mRNA, III-11 LNP@S mRNA were prepared according to the method described in Example 30, wherein the mass ratio of ionizable lipid to Luc mRNA was 15:1, and the concentration of mRNA in the preparation was 0.1 mg/mL.

Example 34 Immunization Protocol of SARS-CoV-2 mRNA Vaccines (1) Grouping and administration of mice: BALB/c male mice were randomly divided into groups according to the preparation. In each immunization, 100 μL of mice were injected into the tail vein, that is, 10 μg of S mRNA per mouse. PBS was used as negative Control. Formulations are grouped as: II-5 LNP@S mRNA, II-18 LNP@S mRNA, II-24 LNP@S mRNA, II-25 LNP@S mRNA, III-3 LNP@S mRNA, and III-11 LNP@S mRNA.
(2) Second immunization and sample collection: The first immunization was recorded as Day 0, and blood was collected after two weeks before the second immunization, and blood was collected every two weeks thereafter.

Figure 9:
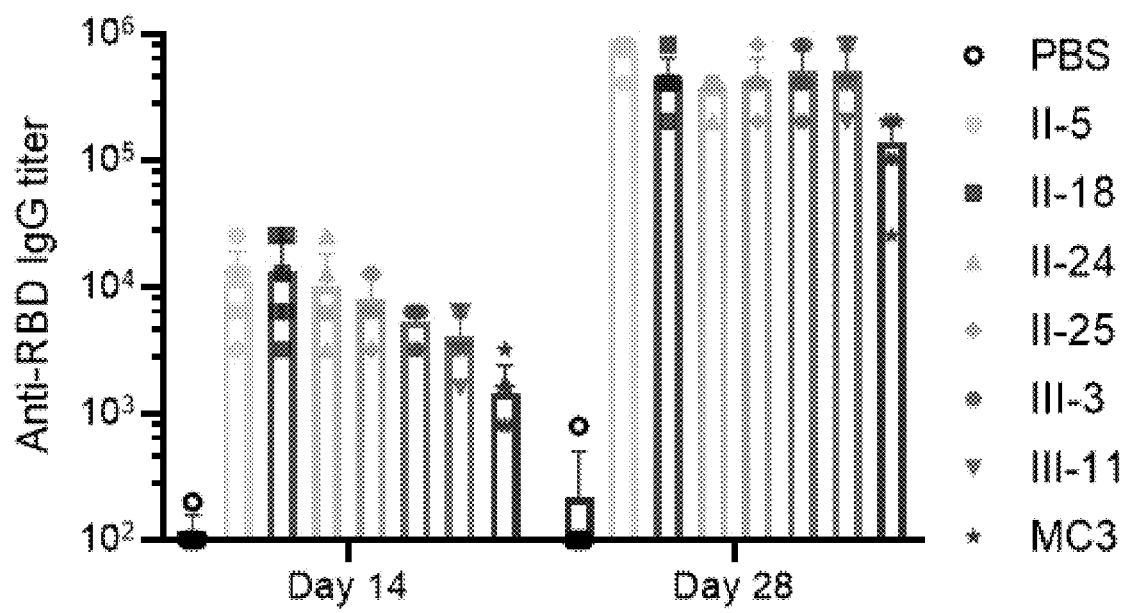
FIG. 9 shows Titers of RBD-specific IgG in the sera of immunized mice.

Example 35 Detection of Specific Antibody Titers by Enzyme-Linked Immunosorbent Assay (1) Antigen coating: RBD protein (Delta, WT or Omicron) was prepared into antigen protein solution with 1× coating working solution, and 100 μL was added to each well. To avoid the existence of air bubbles, the mixture was placed in the refrigerator at 4° C. overnight.
(2) BSA blocking: After the antigen was coated overnight, discard the liquid in the coated ELISA plate, add 300 μL of 1× washing working solution to each well, discard the liquid in the ELISA plate, and repeat the plate washing 4 times. BSA was made up as blocking solution with 1× wash solution. After washing the plate, add 100 μL of blocking solution to each well and incubate at 25° C. for 4 h.
(3) Serum dilution and sample loading: centrifuge the orbital blood of the immunized mice, aspirate the serum, and inactivate at 60° C. for 30 min. Using the antibody diluent, take 100-fold as the initial dilution, and carry out 2-fold serial dilution. After the closure, the plate was washed 4 times. Add 100 μL of serum sample diluent to each well of the washed ELISA plate. Incubate overnight in a 4° C. refrigerator.
(4) Antibody incubation: After the serum was incubated overnight, the plate was washed 4 times. The HRP-labeled antibody was diluted to the corresponding multiples with antibody diluent, 100 μL of antibody diluent was added to each well and incubated at 25° C. for 2 h.
(5) Color development and detection: After the antibody incubation, wash the plate 4 times. Add 100 μL of chromogenic solution to each well and incubate at 25° C. for 30 min in the dark. Add 100 μL of sulfuric acid stop solution to each well. Immediately after adding the stop solution, read the absorbance values at 450 nm and 630 nm with a microplate reader. Analyze the data, and determine the dilution end point according to the difference between the absorbance values of the Control group, so as to determine the dilution factor of the end point in the immunization group, which is the titer. RBD of each group of II-5 LNP@S mRNA, II-18 LNP@S mRNA, II-24 LNP@S mRNA, II-25 LNP@S mRNA, III-3 LNP@S mRNA and III-11 LNP@S mRNA The specific IgG titer is shown in FIG. 9, and the results show that the ionizable lipids of the present disclosure can induce strong humoral immune responses when used in SARS-CoV-2 mRNA vaccines.

Figure 10:
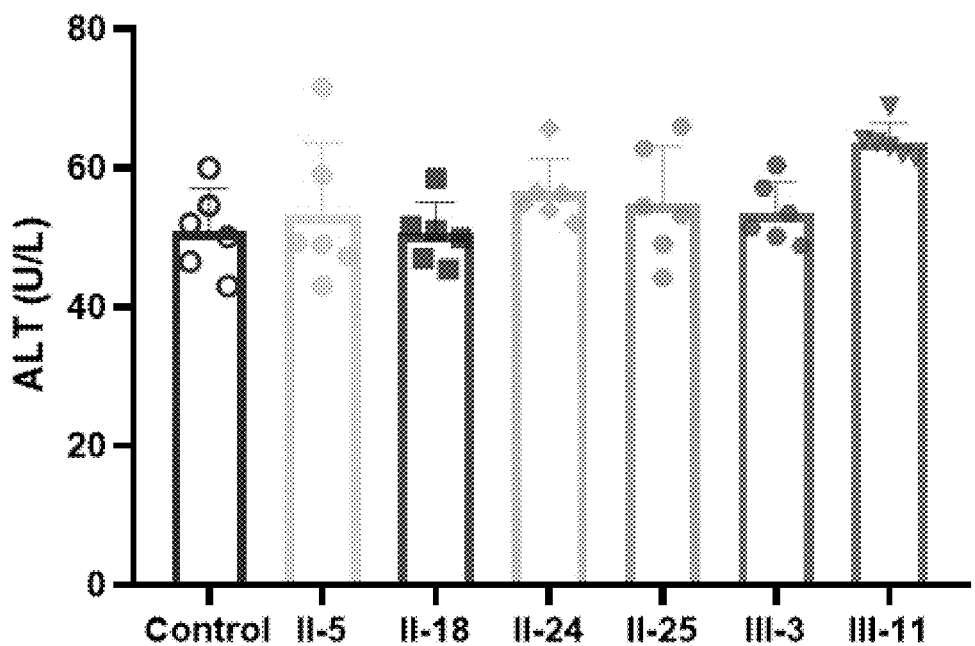
FIG. 10 shows alanine transaminase (ALT) level of the immunized mice.
Figure 11:
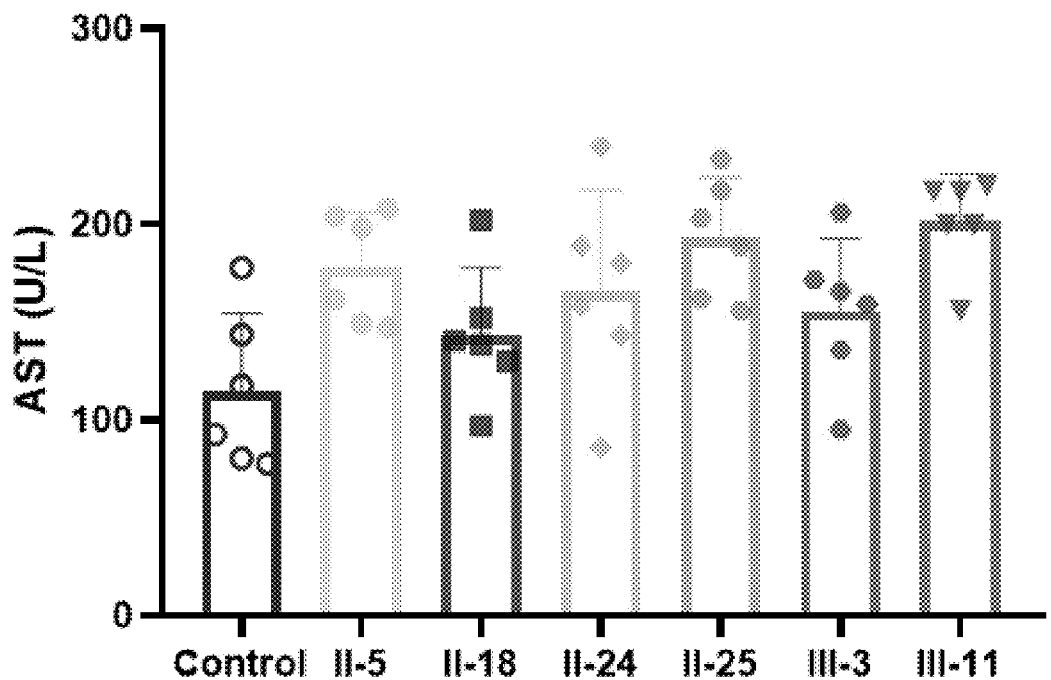
FIG. 11 shows aspartate aminotransferase (AST) level of the immunized mice.
Figure 12:
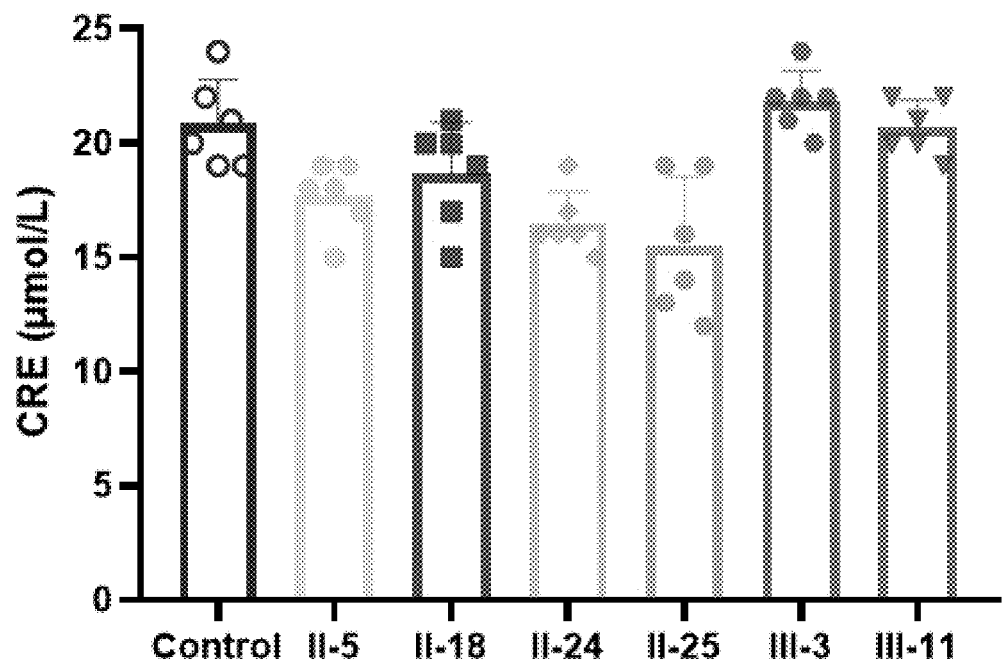
FIG. 12 shows creatinine (CRE) level of the immunized mice.

Example 36 Safety Evaluation of LNP@S mRNA Vaccines (1) Preparation and administration of preparations: II-5 LNP@S mRNA, II-18 LNP@S mRNA, II-24 LNP@S mRNA, II-25 LNP@S mRNA, III-3 LNP @S mRNA and III-11 LNP@S mRNA preparations were prepared according to Example 33. The mRNA concentration of the adjusted preparation was 0.1 mg/mL, and the blank BALB/c mice were intramuscularly injected with 200 μL, that is, 20 μg S mRNA/mice, and an equal volume of PBS was used as a control.
(2) Blood collection and detection: 24 hours after administration, the orbital blood of mice was collected, centrifuged, and the serum was drawn to use a biochemical analyzer to detect major biochemical indicators, as shown in FIGS. 10-12. The results show that the ionizable lipids of the present disclosure are safe when used in SARS-CoV-2 mRNA vaccines.

Notably, the specific features, structures, materials or features described in this specification may be combined in an appropriate manner in any one or more examples. In addition, technicians in the field may combine the different examples described in this specification and the characteristics of different embodiments under non-contradictory condition.

The invention claimed is:
1. A compound of Formula (I):

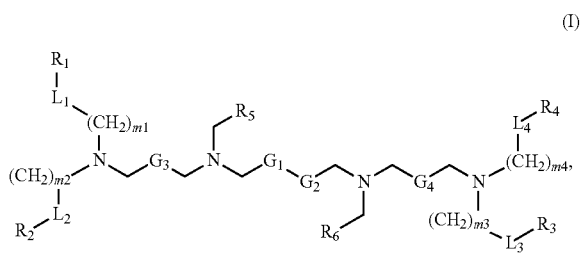

or a pharmaceutically acceptable salt thereof, wherein
m1, m2, m3, and m4 are each independently selected from 1, 2, 3, 4, or 5;
$L_1$, $L_2$, $L_3$, and $L_4$ are each independently selected from —CH(OH)—, —C(=O)—, —C(=O)O—, —OC(=O)—, —C(=O)S—, —SC(=O)—, —C(=O)NR$_a$—, —NR$_a$C(=O)—, —NR$_a$C(=O)O—, —OC(=O)NR$_a$—, —O—, —O—O—, —S—, —S—S—, —S—S—S—, —CH(OH)CH$_2$O—, —CH(OH)CH$_2$S—, or absent, wherein
each $R_a$ is independently —H or optionally substituted $C_1$-$C_6$ alkyl;
$R_1$, $R_2$, $R_3$, and $R_4$ are each independently selected from optionally substituted $C_6$-$C_{30}$ alkyl, optionally substituted $C_6$-$C_{30}$ alkenyl, or optionally substituted $C_6$-$C_{30}$ alkynyl;
$G_1$, $G_2$, $G_3$ and $G_4$ are each independently selected from —R$_c$—, —R$_c$CH(OH)R$_d$—, —R$_c$C(=O)R$_d$—, —R$_c$C(=O)OR$_d$—, —R$_c$OC(=O)R$_d$—, —R$_c$C(=O)SR$_d$—, —R$_c$SC(=O)R$_d$—, —R$_c$C(=O)N(R$_b$)R$_d$—, —R$_c$N(R$_b$)C(=O)R$_d$—, —R$_c$N(R$_b$)C(=O)OR$_d$—, —R$_c$OC (=O)N($R_b$)$R_d$—, —$R_c$O$R_d$—, —$R_c$—O—O—$R_d$—, —$R_c$S$R_d$—, —$R_c$—S—S—$R_d$—, —$R_c$—S—S—S—$R_d$—, or absent; wherein
- each $R_b$ is independently —H or optionally substituted $C_1$-$C_6$ alkyl;
- each $R_c$ and $R_d$ are independently —(CH$_2$)$_n$—, and n is 0, 1, 2, 3, or 4;

$R_5$ and $R_6$ are each independently selected from —H, —OH, or optionally substituted $C_1$-$C_6$ alkyl.

2. The compound of claim 1 or a pharmaceutically acceptable salt thereof, wherein
- i) $G_1$ and $G_2$ are each independently —$R_c$—, $G_3$ and $G_4$ are each independently selected from —$R_c$—, —$R_c$C(=O)$R_d$—, —$R_c$C(=O)O$R_d$—, —$R_c$OC(=O)$R_d$—, —$R_c$C(=O)N($R_b$)$R_d$—, —$R_c$N($R_b$)C(=O)$R_d$—, —$R_c$N($R_b$)C(=O)O$R_d$—, —$R_c$OC(=O)N($R_b$)$R_d$—, or absent;
    - each $R_b$ is independently —H or $C_1$-$C_6$ alkyl;
    - each $R_c$ and $R_d$ are independently —(CH$_2$)$_n$—, and n is 0, 1, 2, 3, or 4; or
- ii) $G_1$ and $G_2$ are each independently —$R_c$—, $G_3$ and $G_4$ are each independently selected from —$R_c$—, —$R_c$C(=O)O$R_d$—, —$R_c$OC(=O)$R_d$—, —$R_c$C(=O)N($R_b$)$R_d$—, —$R_c$N($R_b$)C(=O)$R_d$—, or absent;
    - each $R_b$ is independently —H or $C_1$-$C_2$ alkyl;
    - each $R_c$ and $R_d$ are independently —(CH$_2$)$_n$— or absent, and n is 0, 1 or 2.

3. The compound of claim 2 or a pharmaceutically acceptable salt thereof, wherein
$G_1$ and $G_2$ are absent, $G_3$ and $G_4$ are each independently selected from —CH$_2$—, —CH$_2$C(=O)OCH$_2$—, —CH$_2$OC(=O)CH$_2$—, —CH$_2$C(=O)NHCH$_2$—, —CH$_2$NHC(=O)CH$_2$—, or absent.

4. The compound of claim 1 or a pharmaceutically acceptable salt thereof, wherein
- i) $G_3$ and $G_4$ are each independently —$R_c$—, $G_1$ and $G_2$ are each independently selected from —$R_c$—, —$R_c$C(=O)$R_d$—, —$R_c$C(=O)O$R_d$—, —$R_c$OC(=O)$R_d$—, —$R_c$C(=O)N($R_b$)$R_d$—, —$R_c$N($R_b$)C(=O)$R_d$—, —$R_c$N($R_b$)C(=O)O$R_d$—, —$R_c$OC(=O)N($R_b$)$R_d$—, or absent;
    - each $R_b$ is independently —H or $C_1$-$C_6$ alkyl;
    - each $R_c$ and $R_d$ are independently —(CH$_2$)$_n$—, and n is 0, 1, 2, 3, or 4; or
- ii) $G_3$ and $G_4$ are each independently —$R_c$—, $G_1$ and $G_2$ are each independently selected from —$R_c$—, —$R_c$C(=O)O$R_d$—, —$R_c$OC(=O)$R_d$—, —$R_c$C(=O)N($R_b$)$R_d$—, —$R_c$N($R_b$)C(=O)$R_d$—, or absent;
    - each $R_b$ is independently —H or $C_1$-$C_2$ alkyl;
    - each $R_c$ and $R_d$ are independently —(CH$_2$)$_n$— or absent, and n is 0, 1 or 2; or
- iii) $G_3$ and $G_4$ are absent, $G_1$ and $G_2$ are each independently selected from —CH$_2$—, —CH$_2$C(=O)O(CH$_2$)$_{1\ or\ 2}$—, —(CH$_2$)$_{1\ or\ 2}$OC(=O)CH$_2$—, —CH$_2$C(=O)N($R_b$)CH$_2$—, —CH$_2$N($R_b$)C(=O)CH$_2$—, or absent;
    - each $R_b$ is independently —H or $C_1$-$C_2$ alkyl.

5. The compound of claim 1 or a pharmaceutically acceptable salt thereof, wherein
- i) $L_1$, $L_2$, $L_3$, and $L_4$ are each independently selected from —CH(OH)—, —C(=O)—, —C(=O)O—, —OC(=O)—, —C(=O)N$R_a$—, —N$R_a$C(=O)—, —N$R_a$C(=O)O—, —OC(=O)N$R_a$—, —O—, —S—, —CH(OH)CH$_2$O—, —CH(OH)CH$_2$S—, or absent; or
- ii) $L_1$, $L_2$, $L_3$, and $L_4$ are each independently selected from —CH(OH)—, —C(=O)—, —C(=O)O—, —OC(=O)—, —C(=O)N$R_a$—, —N$R_a$C(=O)—, —O—, —S—, or absent; each $R_a$ is independently —H or $C_1$-$C_2$ alkyl.

6. The compound of claim 1 or a pharmaceutically acceptable salt thereof, wherein m1, m2, m3, and m4 are each independently selected from 1 or 2.

7. The compound of claim 1 or a pharmaceutically acceptable salt thereof, wherein
- i) $R_1$, $R_2$, $R_3$, and $R_4$ are each independently selected from $C_6$-$C_{18}$ alkyl, $C_6$-$C_{18}$ alkenyl, or $C_6$-$C_{18}$ alkynyl, wherein said $C_6$-$C_{18}$ alkyl, $C_6$-$C_{18}$ alkenyl, or $C_6$-$C_{18}$ alkynyl is optionally substituted one to three groups selected from halogen, OH, or =O; or
- ii) $R_1$, $R_2$, $R_3$, and $R_4$ are each independently selected from $C_6$-$C_{18}$ alkyl.

8. The compound of claim 1 or a pharmaceutically acceptable salt thereof, wherein $R_5$ and $R_6$ are each independently selected from —H, —OH, or $C_1$-$C_4$ alkyl optionally substituted with —OH.

9. A compound of Formula (I-1):

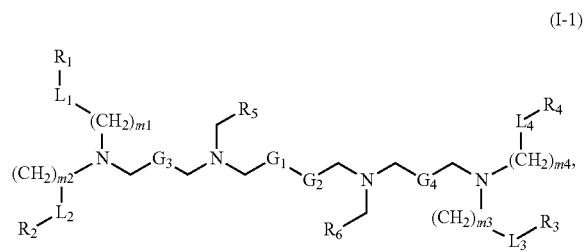

or a pharmaceutically acceptable salt thereof, wherein
- m1, m2, m3, and m4 are the same, all of which are 1, 2, 3, 4, or 5;
- $L_1$, $L_2$, $L_3$, and $L_4$ are the same, all of which are selected from —CH(OH)—, —C(=O)—, ^—C(=O)O—^, ^—OC(=O)—, ^—C(=O)S—^, ^—SC(=O)—^, ^—C(=O)N$R_a$-^, ^—N$R_a$C(=O)—^, ^—N$R_a$C(=O)O—^, ^—OC(=O)N$R_a$-^, —O—, —O—O—, —S—, —S—S—, —S—S—S—, ^—CH(OH)CH$_2$O—^, ^—CH(OH)CH$_2$S—^ or absent, wherein
  - ^- represents the point which attaches to $R_{1-4}$;
  - -^ represents the point which attaches to —(CH$_2$)$_{m1-m4}$—; and
- each $R_a$ is independently —H or optionally substituted $C_1$-$C_6$ alkyl;
- $R_1$, $R_2$, $R_3$, and $R_4$ are the same, all of which are selected from optionally substituted $C_6$-$C_{30}$ alkyl, optionally substituted $C_6$-$C_{30}$ alkenyl, or optionally substituted $C_6$-$C_{30}$ alkynyl;
- $G_1$ and $G_2$ are the same, and $G_3$ and $G_4$ are the same, when $G_1$ and $G_2$ are —$R_c$—, $G_3$ and $G_4$ are selected from —$R_c$—, *—$R_c$CH(OH)$R_d$—**, *—$R_c$C(=O)$R_d$—**, *—$R_c$C(=O)O$R_d$—**, *—$R_c$OC(=O)$R_d$—**, *—$R_c$C(=O)S$R_d$—**, *—$R_c$SC(=O)$R_d$—**, *—$R_c$C(=O)N($R_b$)$R_d$—**, *—$R_c$N($R_b$)C(=O)$R_d$—**, *—$R_c$N($R_b$)C(=O)O$R_d$—**, *—$R_c$OC(=O)N($R_b$)$R_d$—**, *—$R_c$O$R_d$—**, *—$R_c$—O—O—$R_d$—**, *—$R_c$S$R_d$—, —$R_c$—S—S—$R_d$—**, *—$R_c$—S—S—S—$R_d$—**, or absent; wherein
  - *- represents the point which attaches to the —CH$_2$— group next to the terminal tertiary amine atom as shown in Formula (I); -** represents the point which attaches to the —CH$_2$— group next to the middle tertiary amine atom as shown in Formula (I);

when $G_3$ and $G_4$ are —$R_c$—, $G_1$ and $G_2$ are selected from —$R_c$—, #—$R_c$CH(OH)$R_d$—##, #—$R_c$C(=O)$R_d$—##, #—$R_c$C(=O)O$R_d$—##, #—$R_c$OC(=O)$R_d$—##, #—$R_c$C(=O)S$R_d$—##, #—$R_c$SC(=O)$R_d$—##, #—$R_c$C(=O)N($R_b$)$R_d$—##, #—$R_c$N($R_b$)C(=O)$R_d$—##, #—$R_c$N($R_b$)C(=O)O$R_d$—##, #—$R_c$OC(=O)N($R_b$)$R_d$—##, #—$R_c$O$R_d$—##, #—$R_c$—O—O—$R_d$—##, #—$R_c$S$R_d$—##, #—$R_c$—S—S—$R_d$—##, #—$R_c$—S—S—S—$R_d$—##, or absent;

wherein

- represents the point which attaches to the —$CH_2$— group next to the middle tertiary amine atom as shown in Formula (I); -## represents the point connecting $G_1$ and $G_2$; and each $R_b$ is independently —H or optionally substituted $C_1$-$C_6$ alkyl;

each $R_c$ and $R_d$ are independently —$(CH_2)_n$—, and n is 0, 1, 2, 3, or 4;

$R_5$ and $R_6$ are the same, both of which are selected from —H, —OH, or optionally substituted $C_1$-$C_6$ alkyl.

10. The compound of claim 9 or a pharmaceutically acceptable salt thereof, wherein i) $G_1$ and $G_2$ are —$R_c$—, $G_3$ and $G_4$ are selected from —$R_c$—, *—$R_c$C(=O)$R_d$—**, *—$R_c$C(=O)O$R_d$—**, *—$R_c$OC(=O)$R_d$—**, *—$R_c$C(=O)N($R_b$)$R_d$—**, *—$R_c$N($R_b$)C(=O)$R_d$—**, *—$R_c$N($R_b$)C(=O)O$R_d$—**, *—$R_c$OC(=O)N($R_b$)$R_d$—**, or absent;

each $R_b$ is independently —H or $C_1$-$C_6$ alkyl;

each $R_c$ and $R_d$ are independently —$(CH_2)_n$—, and n is 0, 1, 2, 3, or 4;

ii) $G_1$ and $G_2$ are —$R_c$—, $G_3$ and $G_4$ are selected from *—$R_c$C(=O)O$R_d$—**, *—$R_c$OC(=O)$R_d$—**, *—$R_c$C(=O)N($R_b$)$R_d$—**, *—$R_c$N($R_b$)C(=O)$R_d$—**, or absent;

each $R_b$ is independently —H or $C_1$-$C_2$ alkyl;

each $R_c$ and $R_d$ are independently —$(CH_2)_n$— or absent, and n is 0, 1 or 2;

iii) $G_1$ and $G_2$ are absent, $G_3$ and $G_4$ are selected from —$CH_2$—, *—$CH_2$C(=O)O$CH_2$—**, *—$CH_2$OC(=O)$CH_2$—**, *—$CH_2$C(=O)NH$CH_2$—**, *—$CH_2$NHC(=O)$CH_2$—**, or absent;

iv) $G_3$ and $G_4$ are —$R_c$—, $G_1$ and $G_2$ are selected from —$R_c$—, #—$R_c$C(=O)$R_d$—##, #—$R_c$C(=O)O$R_d$—##, #—$R_c$OC(=O)$R_d$—##, #—$R_c$C(=O)N($R_b$)$R_d$—##, #—$R_c$N($R_b$)C(=O)$R_d$—##, #—$R_c$N($R_b$)C(=O)O$R_d$—##, #—$R_c$OC(=O)N($R_b$)$R_d$—##, or absent;

each $R_b$ is independently —H or $C_1$-$C_6$ alkyl;

each $R_c$ and $R_d$ are independently —$(CH_2)_n$—, and n is 0, 1, 2, 3, or 4;

v) $G_3$ and $G_4$ are —$R_c$—, $G_1$ and $G_2$ are selected from —$R_c$—, #—$R_c$C(=O)O$R_d$—##, #—$R_c$OC(=O)$R_d$—##, #—$R_c$C(=O)N($R_b$)$R_d$—##, #—$R_c$N($R_b$)C(=O)$R_d$—##, or absent;

each $R_b$ is independently —H or $C_1$-$C_2$ alkyl;

each $R_c$ and $R_d$ are independently —$(CH_2)_n$— or absent, and n is 0, 1 or 2; or vi) $G_3$ and $G_4$ are absent, $G_1$ and $G_2$ are selected from —$CH_2$—, #—$CH_2$C(=O)O$(CH_2)_{1\ or\ 2}$—##, #—$(CH_2)_{1\ or\ 2}$OC(=O)$CH_2$—##, #—$CH_2$C(=O)N($R_b$)$CH_2$—##, #—$CH_2$N($R_b$)C(=O)$CH_2$—##, or absent;

each $R_b$ is independently —H or $C_1$-$C_2$ alkyl.

11. The compound of claim 9 or a pharmaceutically acceptable salt thereof, wherein i) $L_1$, $L_2$, $L_3$, and $L_4$ are the same, all of which are selected from —CH(OH)—, —C(=O)—, ^—C(=O)O—^^, ^—OC(=O)—^^, ^—C(=O)N$R_a$—^^, ^—N$R_a$C(=O)—^^, ^—N$R_a$C(=O)O—^^, ^—OC(=O)N$R_a$-^^, —O—, —S—, ^—CH(OH)$CH_2$O—^^, ^—CH(OH)$CH_2$S—^^, or absent; or ii) $L_1$, $L_2$, $L_3$, and $L_4$ are the same, all of which are selected from —CH(OH)—, —C(=O)—, ^—C(=O)O—^^, ^—OC(=O)—^^, ^—C(=O)N$R_a$-^^, ^N$R_a$C(=O)—^^, —O—, —S—, or absent; each $R_a$ is independently —H or $C_1$-$C_2$ alkyl.

12. The compound of claim 9 or a pharmaceutically acceptable salt thereof, wherein m1, m2, m3, and m4 are the same, all of which are 1 or 2.

13. The compound of claim 9 or a pharmaceutically acceptable salt thereof, wherein i) $R_1$, $R_2$, $R_3$, and $R_4$ are the same, all of which are selected from $C_6$-$C_{18}$ alkyl, $C_6$-$C_{18}$ alkenyl, or $C_6$-$C_{18}$ alkynyl, wherein said $C_6$-$C_{18}$ alkyl, $C_6$-$C_{18}$ alkenyl, or $C_6$-$C_{18}$ alkynyl is optionally substituted one to three groups selected from halogen, OH, or =O; or ii) $R_1$, $R_2$, $R_3$, and $R_4$ are the same, all of which are selected from $C_6$-$C_{18}$ alkyl.

14. The compound of claim 9 or a pharmaceutically acceptable salt thereof, wherein $R_5$ and $R_6$ are the same, both of which are selected from —H, —OH, or $C_1$-$C_4$ alkyl optionally substituted with —OH.

15. The compound of claim 9, or a pharmaceutically acceptable salt thereof, selected from the compounds below,

| Number | Code | Chemical formula |
|---|---|---|
| 1 | II-1 | |
| 2 | III-1 | |

| Number | Code | Chemical formula |
|---|---|---|
| 3 | II-2 | |
| 4 | II-3 | |
| 5 | II-4 | |
| 6 | III-2 | |
| 7 | V-1 | |
| 8 | II-5 | |
| 9 | III-3 | |
| 10 | IV-1 | |
| 11 | VI-1 | |

-continued

| Number | Code | Chemical formula |
|---|---|---|
| 12 | II-6 | |
| 13 | IV-2 | |
| 14 | II-7 | |
| 15 | VI-2 | |
| 16 | II-8 | |
| 17 | II-9 | |
| 18 | II-10 | |
| 19 | III-4 | |
| 20 | VI-3 | |

| Number | Code | Chemical formula |
|---|---|---|
| 21 | III-5 | |
| 22 | II-11 | |
| 23 | II-12 | |
| 24 | III-6 | |
| 25 | II-13 | |
| 26 | IV-3 | |
| 27 | II-14 | |
| 28 | II-15 | |
| 29 | II-16 | |

-continued

| Number | Code | Chemical formula |
|---|---|---|
| 30 | II-17 | |
| 31 | II-18 | |
| 32 | II-19 | |
| 33 | V-2 | |
| 34 | III-7 | |
| 35 | II-20 | |
| 36 | III-8 | |
| 37 | II-21 | |
| 38 | V-3 | |

| Number | Code | Chemical formula |
|---|---|---|
| 39 | IV-4 | |
| 40 | II-22 | |
| 41 | III-9 | |
| 42 | II-23 | |
| 43 | III-10 | |
| 44 | V-4 | |
| 45 | VI-4 | |
| 46 | II-24 | |
| 47 | II-25 | |

-continued

| Number | Code | Chemical formula |
|---|---|---|
| 48 | II-26 | |
| 49 | III-11 | |
| 50 | III-12 | |
| 51 | II-27 | |
| 52 | II-28 | |
| 53 | III-13 | |
| 54 | III-14 | |
| 55 | II-29 | |
| 56 | II-30 | |
| 57 | II-31 | |

-continued

| Number | Code | Chemical formula |
|---|---|---|
| 58 | II-32 | |
| 59 | II-15 | |
| 60 | II-33 | |
| 61 | II-34 | |
| 62 | II-35 | |
| 63 | II-36 | |
| 64 | III-16 | |
| 65 | II-37 | |
| 66 | II-38 | |

16. The compound of claim 1, wherein the compound is in the form of a pharmaceutically acceptable salt.

17. A pharmaceutical composition comprising the compound of claim 9, or a pharmaceutically acceptable salt thereof, and a nucleic acid drug.

18. The pharmaceutical composition of claim 17, wherein the composition further comprises at least one excipient selected from a neutral phospholipid, a steroid, and a polyethylene glycol lipid.

19. The pharmaceutical composition of claim 18, wherein i) the neutral phospholipid is selected from DOPE, DSPC, DOPC, DSPE, DMPC, DMPE, DPPC, DPPE, DEPC, HSPC, POPC or a combination thereof, or ii) the neutral phospholipid is DOPE.

20. The pharmaceutical composition of claim 18, wherein i) the mole ratio of the compound: the neutral phospholipid is 1:1~5:1; or ii) the mole ratio of the compound: the steroid is 1:2~2:1.

21. The pharmaceutical composition of claim 18, wherein i) the steroid is selected from cholesterol, sitosterol, soybean sterol, wool sterol, ergosterol or a combination thereof; or ii) the steroid is cholesterol.

22. The pharmaceutical composition of claim 18, wherein i) the polyethylene glycol lipid is selected from DMG-PEG, DSPE-PEG or a combination thereof, or the polyethylene glycol lipid is DMG-PEG2000.

23. The pharmaceutical composition of claim 18, wherein i) the mole ratio of the compound: the polyethylene glycol lipid is 5:1~100:1; or ii) the mole ratio of the compound: the polyethylene glycol lipid is 10:1~20:1.

24. The pharmaceutical composition of claim 18, wherein i) the nucleic acid drug is selected from DNA, ASO, siRNA, miRNA, mRNA, ribozyme, aptamer or a combination thereof, or ii) the pharmaceutical composition is prepared into lipid nanoparticles (LNP).

* * * * *